United States Patent
Honda et al.

(10) Patent No.: US 11,826,424 B2
(45) Date of Patent: *Nov. 28, 2023

(54) COMPOSITIONS AND METHODS FOR INDUCTION OF TH17 CELLS

(71) Applicants: RIKEN, Wako (JP); The University of Tokyo, Tokyo (JP); School Corporation, Azabu Veterinary Medicine Educational Institution, Sagamihara (JP)

(72) Inventors: Kenya Honda, Wako (JP); Koji Atarashi, Wako (JP); Masahira Hattori, Tokyo (JP); Hidetoshi Morita, Sagamihara (JP)

(73) Assignees: RIKEN, Wako (JP); The University of Tokyo, Tokyo (JP); School Corporation, Azabu Veterinary Medicine Educational Institution, Sagamihara (JP)

( * ) Notice: Subject to any disclaimer, the term of this patent is extended or adjusted under 35 U.S.C. 154(b) by 174 days.

This patent is subject to a terminal disclaimer.

(21) Appl. No.: 17/321,131

(22) Filed: May 14, 2021

(65) Prior Publication Data

US 2022/0072125 A1  Mar. 10, 2022

Related U.S. Application Data

(63) Continuation of application No. 16/375,935, filed on Apr. 5, 2019, now abandoned, which is a continuation of application No. 15/302,755, filed as application No. PCT/JP2015/061771 on Apr. 10, 2015, now Pat. No. 10,300,137.

(60) Provisional application No. 61/978,182, filed on Apr. 10, 2014.

(51) Int. Cl.
| | |
|---|---|
| *A01N 63/00* | (2020.01) |
| *A61K 39/39* | (2006.01) |
| *A61K 35/74* | (2015.01) |
| *A61K 35/741* | (2015.01) |
| *A61K 35/742* | (2015.01) |
| *A61K 35/745* | (2015.01) |
| *A61K 39/00* | (2006.01) |

(52) U.S. Cl.
CPC ............. *A61K 39/39* (2013.01); *A61K 35/74* (2013.01); *A61K 35/741* (2013.01); *A61K 35/742* (2013.01); *A61K 35/745* (2013.01); *A61K 2039/52* (2013.01); *A61K 2039/542* (2013.01); *A61K 2039/57* (2013.01)

(58) Field of Classification Search
CPC .................................................... A61K 39/39
See application file for complete search history.

(56) References Cited

U.S. PATENT DOCUMENTS

| | | | |
|---|---|---|---|
| 5,951,977 | A | 9/1999 | Nisbet et al. |
| 6,319,958 | B1 | 11/2001 | Johnson et al. |
| 10,300,137 | B2 | 5/2019 | Honda et al. |
| 2003/0092754 | A1 | 5/2003 | Nishimuta et al. |
| 2008/0131556 | A1 | 6/2008 | De Simone |
| 2011/0149339 | A1 | 6/2011 | Chae |
| 2011/0311617 | A1 | 12/2011 | Shirakawa et al. |
| 2013/0149339 | A1 | 6/2013 | Honda et al. |
| 2013/0266539 | A1 | 10/2013 | Borody |
| 2014/0357499 | A1 | 12/2014 | Gordon |
| 2017/0028061 | A1 | 2/2017 | Honda et al. |
| 2019/0290753 | A1 | 9/2019 | Honda et al. |

FOREIGN PATENT DOCUMENTS

| | | |
|---|---|---|
| EP | 0640349 A1 | 3/1995 |
| JP | 59128333 A | 7/1984 |
| JP | 2010-155801 A | 7/2010 |
| JP | 201132170 A | 2/2011 |
| KR | 10-2011-0026528 A | 3/2011 |
| WO | WO 99/019459 A1 | 4/1999 |
| WO | WO 2004/017962 A2 | 3/2004 |
| WO | WO 2011/079282 A1 | 6/2011 |
| WO | WO 2011/135194 A2 | 11/2011 |
| WO | WO 2013/080561 A1 | 6/2013 |

OTHER PUBLICATIONS

EP 15776630.4, dated Feb. 26, 2018, Extended European Search Report.
EP 15776630.4, dated Nov. 20, 2017, Partial Supplementary European Search Report.
PCT/JP2015/061771, dated Jul. 14, 2015, International Search Report and Written Opinion.
Asahara, Preventive Effect of Probiotic Bifidobacteria against Shiga Toxin-Producing *Escherichia coli* and *Salmonella* Infections. Bioscience Micro. 2010;29: 11-21.
Atarashi et al., ATP drives lamina propria T(H)17 cell differentiation. Nature. Oct. 9, 2008;455(7214): 808-12. doi: 10.1038/nature07240.
Atarashi et al., Regulation of Th17 cell differentiation by intestinal commensal bacteria. Benef Microbes. Nov. 2010;1(4): 327-34. doi: 10.3920/BM2010.0026.

(Continued)

*Primary Examiner* — Albert M Navarro

(74) *Attorney, Agent, or Firm* — Wolf, Greenfield & Sacks, P.C.

(57) ABSTRACT

Strains of human-derived bacteria have been obtained from complex fecal samples and shown to induce accumulation of Th17 cells in the intestine and promote immune functions. Pharmaceutical compositions containing these bacteria can be used as anti-infectives and as adjuvants in mucosal vaccines.

18 Claims, 5 Drawing Sheets

Specification includes a Sequence Listing.

(56) References Cited

OTHER PUBLICATIONS

Atarashi et al., Th17 cell induction by adhesion of microbes to intestinal epithelial cells. Cell. Oct. 8, 2015;163(2): 367-80. doi: 10.1016/j.cell.2015.08.058. Epub Sep. 24, 2015.

Barnes et al., Regulatory T cells reinforce intestinal homeostasis. Immunity. Sep. 18, 2009;31(3): 401-11. doi: 10.1016/j.immuni.2009.08.011.

Bouskra et al., Lymphoid tissue genesis induced by commensals through NOD1 regulates intestinal homeostasis. Nature. Nov. 27, 2008;456(7221): 507-10. doi: 10.1038/nature07450.

Cebra, Influences of microbiota on intestinal immune system development. Am J Clin Nutr. May 1999;69(5): 1046S-1051S.

Curotto De Lafaille et al., Natural and adaptive Foxp3+ regulatory T cells: more of the same or a division of labor? Immunity. May 2009;30(5): 626-35. doi: 10.1016/j.immuni.2009.05.002.

Eun et al., Induction of bacterial antigen-specific colitis by a simplified human microbiota consortium in gnotobiotic interleukin-10.sup.-/-mice. Infect Immun. Jun. 2014;82(6): 2239-46. doi: 10.1128/IAI.01513-13.

Fonty et al Applied and Environmental Microbiology. 73(20): 6391-6403 (Year: 2007).

Gaboriau-Routhiau et al., The key role of segmented filamentous bacteria in the coordinated maturation of gut helper T cell responses. Immunity. Oct. 16, 2009;31(4): 677-89. doi: 10.1016/j.immuni.2009.08.020.

Garrett et al., Communicable ulcerative colitis induced by T-bet deficiency in the innate immune system. Cell. Oct. 5, 2007;131(1): 33-45.

Ivanov et al., Induction of intestinal Th17 cells by segmented filamentous bacteria. Cell. Oct. 30, 2009;139(3):485-98. doi: 10.1016/j.cell.2009.09.033.

Ivanov et al., Specific microbiota direct the differentiation of IL-17-producing T-helper cells in the mucosa of the small intestine. Cell Host Microbe. Oct. 16, 2008;4(4): 337-49. doi: 10.1016/j.chom.2008.09.009.

Ivanov et al., The orphan nuclear receptor ROR gammat directs the differentiation program of proinflammatory IL-17.sup.+ T helper cells. Cell. Sep. 22, 2006;126(6): 1121-33.

Korn et al., IL-17 and Th17 Cells. Annu Rev Immunol. 2009;27: 485-517. doi: 10.1146/annurev.immunol.021908.132710.

Lycke, Recent progress in mucosal vaccine development: potential and limitations. Nat Rev Immunol. Jul. 25, 2012;12(8): 592-605. doi: 10.1038/nri3251.

MacPherson et al., Interactions between commensal intestinal bacteria and the immune system. Nat Rev Immunol. Jun. 2004;4(6): 478-85.

Miossec et al., Interleukin-17 and type 17 helper T cells. N Engl J Med. Aug. 27, 2009;361(9): 888-98. doi: 10.1056/NEJMra0707449.

Narushima et al., Characterization of the 17 strains of regulatory T cell-inducing human-derived Clostridia. Gut Microbes. May-Jun. 2014;5(3): 333-9. doi: 10.4161/gmic.28572. Epub Mar. 18, 2014.

Qin et al., A human gut microbial gene catalogue established by metagenomic sequencing. Nature. Mar. 4, 2010;464(7285): 59-65. doi: 10.1038/nature08821.

Round et al., The gut microbiota shapes intestinal immune responses during health and disease. Nat Rev Immunol. May 2009;9(5):313-23. doi:10.1038/nri2515. Review. Erratum in: Nat Rev Immunol. Aug. 2009;9(8): 600.

Salzman et al., Enteric defensins are essential regulators of intestinal microbial ecology. Nat Immunol. Jan. 2010;11(1): 76-83. doi: 10.1038/ni.1825.

Sanos et al., RORgammat and commensal microflora are required for the differentiation of mucosal interleukin 22-producing NKp46.sup.+ cells. Nat Immunol. Jan. 2009;10(1): 83-91. doi: 10.1038/ni.1684.

Yokote et al., NKT cell-dependent amelioration of a mouse model of multiple sclerosis by altering gut flora. Am J Pathol. Dec. 2008;173(6): 1714-23. doi: 10.2353/ajpath.2008.080622.

Bagge et al., Diversity of spore-forming bacteria in cattle manure, slaughterhouse waste and samples from biogas plants. J Appl Microbiol. Nov. 2010;109(5):1549-65. doi: 10.1111/j.1365-2672.2010.04790.x. Epub Jul. 13, 2010.

Atarashi et al., Treg induction by a rationally selected mixture of Clostridia strains from the human microbiota. Nature. Aug. 8, 2013;500(7461):232-6. doi: 10.1038/nature12331. Epub Jul. 10, 2013.

COMPOSITIONS AND METHODS FOR INDUCTION OF TH17 CELLS

RELATED APPLICATIONS

This application is a continuation of Ser. No. 16/375,935, filed Apr. 5, 2019, which is a continuation of U.S. application Ser. No. 15/302,755, filed Oct. 7, 2016, which is a national stage filing under 35 U.S.C. § 371 of international application number PCT/JP2015/061771, filed Apr. 10, 2015, which claims the benefit under 35 U.S.C. § 119(e) of U.S. provisional application Ser. No. 61/978,182, filed Apr. 10, 2014, each of which is incorporated by reference herein in its entirety.

TECHNICAL FIELD

The subject matter described herein relates to a composition of human-derived bacteria that induces proliferation of T helper 17 (Th17) cells and which comprises, as an active component, human-derived bacteria, preferably (a) one or more bacteria isolated and cultured from the ampicillin-resistant bacterial fraction of a fecal sample or, (b) a culture supernatant of one or more bacteria of (a). It also relates to a method for inducing proliferation of Th17 cells. The composition, which comprises any of (a)-(b) above, is referred to as a bacterial composition. Moreover, the subject matter relates to a method for treating or preventing at least one disease or condition that is responsive to induction of Th17 cells, such as infectious diseases, by oral administration of the bacterial composition alone or in combination with an antigen to an individual in need thereof.

BACKGROUND

Hundreds of species of commensal microorganisms are harbored in the gastrointestinal tracts of mammals, where they interact with the host immune system. Research using germ-free (GF) animals has shown that the commensal microorganisms influence the development of the mucosal immune system, such as histogenesis of Peyer's patches (PPs) and isolated lymphoid follicles (ILFs), secretion of antimicrobial peptides from the epithelium, and accumulation of unique lymphocytes in mucosal tissues, including immunoglobulin A-producing plasma cells, intraepithelial lymphocytes, IL-17-producing CD4-positive T cells (Th 17), and IL-22-producing NK-like cells (Non-Patent Literature (NPL) 1 to 7). Consequently, the presence of intestinal bacteria enhances protective functions of the mucous membranes, enabling the host to mount robust immune responses against pathogenic microbes invading the body. On the other hand, the mucosal immune system maintains unresponsiveness to dietary antigens and harmless microbes (NPL Document 3). Abnormality in the regulation of cross-talk between commensal bacteria and the immune system (intestinal dysbiosis) may lead to overly robust or insufficiently robust immune responses to environmental antigens and to commensal and pathogenic microbes, resulting in disease (NPL 8 to 10). Better approaches to enabling the body to mount an effective immune response to invading pathogenic microbes are needed.

PRIOR ART DOCUMENTS

Non Patent Literature

[NPL 1] J. J. Cebra, "Am J Clin Nutr", May, 1999, 69, 1046S
[NPL 2] A. J. Macpherson, N. L. Harris, "Nat Rev Immunol", June 2004, 4, 478
[NPL 3] J. L. Round, S. K. Mazmanian, "Nat Rev Immunol", May 2009, 9, 313
[NPL 4] D. Bouskra et al., "Nature", Nov. 27, 2008, 456, 507
[NPL 5] K. Atarashi et al., "Nature", Oct. 9, 2008, 455, 808
[NPL 6] I. I. Ivanov et al., "Cell Host Microbe", Oct. 16, 2008, 4, 337
[NPL 7] S. L. Sanos et al., "Nat Immunol", January 2009, 10, 83
[NPL 8] M. A. Curotto de Lafaille, J. J. Lafaille, "Immunity", May 2009, 30, 626
[NPL 9] M. J. Barnes, F. Powrie, "Immunity", Sep. 18, 2009, 31, 401
[NPL 10] W. S. Garrett et al., "Cell", Oct. 5, 2007, 131, 33
[NPL 11] I. I. Ivanov, et al., "Cell", Oct. 30, 2009, 139, 485
[NPL 12] V. Gaboriau-Routhiau et al., "Immunity", Oct. 16, 2009, 31, 677
[NPL 13] N. H. Salzman et al., "Nat Immunol", January 2010, 11, 76.
[NPL 14] J. Quin et al., "Nature", Mar. 4, 2010, 464, 59
[NPL 15] T. Korn et al., "Annu Rev Immunol", April 2009, 27, 485
[NPL 16] P. Miossec et al., "N Engl N Med", Aug. 27, 2009, 361, 888
[NPL 17] I. I. Ivanov et al., "Cell", Sep. 22, 2006, 126, 1121
[NPL 18] Lycke N, "Nature Reviews Immunology", August 2012, 12, 605

SUMMARY OF INVENTION

The present compositions and methods have been made in view of the above-described problems in the art. As described herein, although most bacterial species among the more than a thousand species present in the human microbiota do not have the ability to stimulate Th17 cells, the inventors have obtained, from humans, a few bacterial species that have the ability to cause a robust induction of Th17 cells, by modifying fecal samples derived from humans with various antibiotic treatments, applying methods to isolate pure strains in vitro, and developing culturing methods to manufacture bacterial compositions containing the strains that are suitable for use as pharmaceuticals and as food ingredients. Moreover, the inventors have shown that inoculating animals with the in vitro cultured species also leads to a robust accumulation of Th17 cells.

Described herein are methods of obtaining and culturing intestinal commensal bacteria, isolated from humans, which induce, preferably strongly induce, the proliferation, accumulation, or proliferation and accumulation of Th17 cells. Described are compositions, also referred to as bacterial compositions, that comprise, as an active component, (a) one or more of (at least one, a) certain species of bacteria provided herein (Table 1) or bacteria that contain DNA comprising a nucleotide sequence having at least 97% homology (e.g., 97% homology, 98% homology, 99% homology or 100% homology) with sequences provided herein; (b) a culture supernatant of one or more (at least one, a) such bacteria; or (c) a combination of (a) and (b) and induce the proliferation and/or accumulation of T helper 17 cells (Th17 cells).

More specifically:
One embodiment is a composition (referred to as a bacterial composition) that induces proliferation, accumulation or both proliferation and accumulation of Th17 cells, the composition comprising, as an active component, (a) at least one (a, one or more) organism selected from the group consisting of: *Clostridium symbiosum, Clostridium hathewayi, Clostridium citroniae, Clostridium bolteae,*

*Ruminococcus* sp. M-1, *Ruminococcus gnavus*, *Blautia* sp. canine oral taxon 143, *Anaerostipes caccae*, *Clostridium lactatifermentans*, *Coprobacillus cateniformis*, *Clostridium ramosum*, cf. *Clostridium* sp. MLG055, *Clostridium innocuum*, *Eubacterium desmolans*, *Clostridium orbiscindens*, *Ruminococcus* sp. 16442, *Anaerotruncus colihominis*, *Bacteroides dorei*, *Bifidobacterium pseudolongum* subsp. *Pseudolongum*, and *Bifidobacterium breve*; (b) a culture supernatant of at least one (a, one or more) bacteria of (a); or (c) a combination of at least one (a, one or more) bacteria of (a) and a culture surpernatant of at least one (a, one or more) bacteria of (a).

One embodiment is a composition that induces proliferation and/or accumulation of Th17 cells, the composition comprising, as an active component, (a) the ampicillin-resistant bacterial fraction of a fecal sample; (b) a culture supernatant of one or more bacteria of (a); or a combination of (a) and (b).

In some embodiments, the active component is one or more of *Clostridium symbiosum*, *Clostridium hathewayi*, *Clostridium citroniae*, *Clostridium bolteae*, *Ruminococcus* sp. M-1, *Ruminococcus gnavus*, *Blautia* sp. canine oral taxon 143, *Anaerostipes caccae*, *Clostridium lactatifermentans*, *Coprobacillus cateniformis*, *Clostridium ramosum*, cf. *Clostridium* sp. MLG055, *Clostridium innocuum*, *Eubacterium desmolans*, *Clostridium orbiscindens*, *Ruminococcus* sp. 16442, *Anaerotruncus colihominis*, *Bacteroides dorei*, *Bifidobacterium pseudolongum* subsp. *Pseudolongum*, and *Bifidobacterium breve*; and a culture supernatant of one or more bacteria described/listed herein. In some embodiments, the active component is a culture supernatant of one or more of the bacteria described/listed herein. In some embodiments, the one or more bacteria or one or more culture supernatant derived from the bacteria is three or more. In some embodiments, the one or more bacteria or one or more culture supernatant derived from the bacteria is five or more. In some embodiments, the one or more bacteria or one or more culture supernatant derived from the bacteria is 10 or more. In some embodiments, the one or more bacteria or one or more culture supernatant derived from the bacteria is 15 or more. In some embodiments, the one or more bacteria or one or more culture supernatant derived from the bacteria is 20.

A bacterial composition as described herein comprises at least one of the following: one bacteria as described herein; at least one culture supernatant obtained from culture in which one (or more) of the bacteria was present (grown or maintained) or a fraction of such a supernatant. It can comprise a combination of any of the foregoing. The term composition/bacterial composition refers to all such combinations.

The bacteria in the composition that induces proliferation and/or accumulation of Th17 cells can be, for example, *Clostridium symbiosum*, *Clostridium hathewayi*, *Clostridium citroniae*, *Clostridium bolteae*, *Ruminococcus* sp. M-1, *Ruminococcus gnavus*, *Blautia* sp. canine oral taxon 143, *Anaerostipes caccae*, *Clostridium lactatifermentans*, *Coprobacillus cateniformis*, *Clostridium ramosum*, cf. *Clostridium* sp. MLG055, *Clostridium innocuum*, *Eubacterium desmolans*, *Clostridium orbiscindens*, *Ruminococcus* sp. 16442, *Anaerotruncus colihominis*, *Bacteroides dorei*, *Bifidobacterium pseudolongum* subsp. *Pseudolongum*, and *Bifidobacterium breve* or any bacteria (such as human-derived bacteria) that contain DNA comprising at least 97% homology (e.g., 97%, 98%, 99% or 100% homology) with sequences provided herein, such as, but not limited to, the nucleotide sequences designated with SEQ ID Nos. 1-20, which are listed at the pages following the last Example and in the Sequence Listing. In specific embodiments, the bacteria contain DNA comprising a nucleotide sequence that has at least 97%, at least 98% or at least 99% homology with one or more DNA sequence designated with SEQ ID Nos. 1-20. Alternatively, the bacteria contain DNA comprising a nucleotide sequence that has at least 97% (97%, 98%, 99%, 100%) homology with DNA of one or more of the following: *Clostridium symbiosum*, *Clostridium hathewayi*, *Clostridium citroniae*, *Clostridium bolteae*, *Ruminococcus* sp. M-1, *Ruminococcus gnavus*, *Blautia* sp. canine oral taxon 143, *Anaerostipes caccae*, *Clostridium lactatifermentans*, *Coprobacillus cateniformis*, *Clostridium ramosum*, cf. *Clostridium* sp. MLG055, *Clostridium innocuum*, *Eubacterium desmolans*, *Clostridium orbiscindens*, *Ruminococcus* sp. 16442, *Anaerotruncus colihominis*, *Bacteroides dorei*, *Bifidobacterium pseudolongum* subsp. *Pseudolongum*, and *Bifidobacterium breve*.

In one embodiment, the composition induces Th17 cells that are transcription factor RORgt-positive T cells or IL-17-producing Th17 cells. In another embodiment, the composition promotes a protective immune response at a mucosal surface.

One embodiment is a pharmaceutical composition that induces proliferation, accumulation or both proliferation and/or accumulation of Th17 cells and promotes immune function. The pharmaceutical composition comprises a bacterial composition described herein and a pharmaceutically acceptable component, such as a carrier, a solvent or a diluent. In specific embodiments, such a pharmaceutical composition comprises (a) (1) at least one (a, one or more) species of bacteria listed in Table 1 or as described herein, (2) a culture supernatant of at least one (a, one or more) such bacteria, or (3) a combination of at least one (a, one or more) species of bacteria listed in Table 1 or as described herein and at least one (a, one or more) culture supernatant of at least one (a, one or more) such bacteria and (b) a pharmaceutically acceptable component, such as carrier, a solvent or a diluent. In specific embodiments, (a) above is at least one organism or substance selected from the group consisting of: *Clostridium symbiosum*, *Clostridium hathewayi*, *Clostridium citroniae*, *Clostridium bolteae*, *Ruminococcus* sp. M-1, *Ruminococcus gnavus*, *Blautia* sp. canine oral taxon 143, *Anaerostipes caccae*, *Clostridium lactatifermentans*, *Coprobacillus cateniformis*, *Clostridium ramosum*, cf. *Clostridium* sp. MLG055, *Clostridium innocuum*, *Eubacterium desmolans*, *Clostridium orbiscindens*, *Ruminococcus* sp. 16442, *Anaerotruncus colihominis*, *Bacteroides dorei*, *Bifidobacterium pseudolongum* subsp. *Pseudolongum*, and *Bifidobacterium breve*, and a culture supernatant of one or more of the bacteria. In some embodiments, (a)(2) above is a culture supernatant of at least one (a, one or more) of the bacteria. In some embodiments, the at least one organism or substances is two or more or three or more. In some embodiments, the at least one organism or substances is four or more or five or more. In some embodiments, the at least one organism or substances is 10 or more. In some embodiments, the at least one organism or substances is 15 or more. In some embodiments, the at least one organism or substances is 20. In further embodiments, (a)(1) above is bacteria (such as human-derived bacteria) that contain DNA comprising at least 97% homology (e.g., 97%, 98%, 99% or 100% homology) with sequences provided herein, such as, but not limited to, the nucleotide sequences designated with SEQ ID Nos. 1-20 herein and listed, for example, at the pages following the last Example and in the Sequence Listing. In specific embodiments of the pharmaceutical composition, the bacteria contain DNA comprising a nucleotide sequence that has at least 97%, at least 98%, at least 99% or at least 100% homology with one or more DNA sequence designated with SEQ ID Nos. 1-20.

The pharmaceutical composition induces the proliferation and/or accumulation of T helper cells (Th17 cells) and promotes immune function.

Also provided is a method of inducing proliferation, accumulation or both proliferation and accumulation of Th17 cells in an individual (e.g., an individual in need thereof, such as an individual in need of induction of proliferation and/or accumulation of Th17 cells). The method comprises administering to the individual a bacterial composition described herein or a pharmaceutical composition comprising a bacterial composition described herein. In the method at least one organism or substance selected from the group consisting of: *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum,* cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum,* and *Bifidobacterium breve*; a culture supernatant of one or more of the bacteria or one or more component of the culture supernatant; or a combination of any number of the foregoing is administered to an individual (also referred to as an individual in need thereof) who can be a healthy individual or an individual in need of prevention, reduction or treatment of a condition or disease. For example, the bacterial compositions described may be administered to an individual in need of treatment, reduction in the severity of or prevention of a disease or condition such as an infectious disease.

Optionally, administration of the bacterial composition may be in combination with, or preceeded by, a course of one or more antibiotics.

Optionally, administration of the bacterial composition may be in combination with administration of at least one prebiotic substance that preferentially favors the growth of the species in the bacterial composition over the growth of other human commensal bacterial species. In one embodiment, the prebiotic substance(s) is, for example, a nondigestible oligosaccharide.

In a further embodiment, the bacterial composition can be used as an adjuvant to improve the efficacy of a mucosal vaccine formulation. For example, the bacterial composition can be used as an adjuvant to a vaccine for the prophylaxis or treatment of an infectious disease or cancer. In some embodiments, a method for prophylaxis or treatment is provided, the method comprising administering the bacterial composition or pharmaceutical composition as a vaccine adjuvant. The bacterial composition or pharmaceutical composition may be administered as an adjuvant with existing mucosal vaccines.

In a further embodiment, the bacterial composition comprises, as an active component, at least one organism selected from the group consisting of: *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum,* cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum,* and *Bifidobacterium breve* wherein the organism comprises an expression vector that contains a heterologous gene, also referred to as a vector expressing a heterologous protein or peptide, such as an antigen.

Assessment of the extent of induction of proliferation or accumulation of Th17 cells that results from administration of a composition described herein can be carried out by a variety of approaches such as by measurement of the number of Th17 cells prior and after administration, or by measurement of Th17 activity, such as expression of at least one of RORgt, IL-17A, IL-17F, IL-22, IL-23, IL-23R, CD161, and CCR6 after the administering relative to the expression of at least one of RORgt, IL-17A, IL-17F, IL-22, IL-23, IL-23R, CD161, and CCR6 determined prior to the administering colonization of an individual with the bacterial composition. The results of such assessments are used as an index of the induction of proliferation or accumulation of Th17 cells in the individual.

In one embodiment, administration of a composition described herein causes induction of the Th17 cells that are transcription factor RORgt-positive Th17 cells or IL-17-producing Th17 cells.

The composition described herein can be administered by a variety of routes and in one embodiment, is administered orally to an individual in need thereof, such as a patient in need thereof. The composition may be administered in a number of oral forms, such as in a dry powder, a lyophilisate, or dissolved in a liquid formulation, in enteric capsules, in sachets, or in a food matrix, such as yogurt, or a drink.

Also provided is a method of monitoring a subject's response to treatment with the bacterial compositions of the invention, comprising: (a) obtaining a (at least one; one or more) sample, such as a fecal sample or a colonic biopsy sample, from a patient before treatment with a bacterial composition described herein; (b) obtaining, a (at least one; one or more) corresponding sample from the patient after treatment with a bacterial composition described herein; and (c) determining and comparing the percentage or absolute counts of at least one bacterial species selected from the group consisting of: *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum,* cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum,* and *Bifidobacterium breve* in the sample obtained in (a) with the percentage or absolute counts of the same at least one bacterial species in the sample obtained in (b), wherein a higher value in the sample obtained in (b) (after treatment with the bacterial composition) than in the sample obtained in (a) (before treatment) indicates that the subject has responded favorably to treatment (e.g. is a positive indicator of enhanced immune response in the subject). In some embodiments, the method further comprises (d) further administering the bacterial composition to the patient or ceasing administration of the bacterial composition to the patient based on the comparison in (c).

Also provided is a method of obtaining Th17-inducing bacterial compositions, comprising (a) treating a subject with the antibiotic ampicillin, or an antibiotic with a similar spectrum, for example an aminopenicillin family member such as amoxicillin, penicillin, or benzylpenicillin; (b) obtaining (at least one) sample, such as a fecal sample or an intestinal biopsy sample from the subject (the "ampicillin-resistant bacterial fraction of a fecal sample"); (c) culturing the sample from (b) and isolating pure bacterial strains from the resulting colonies. In a preferred embodiment the subject in (a) is an ex-germ-free animal that has been colonized with a fecal sample obtained from a human donor. In a preferred embodiment, the isolation of pure bacterial strains of (c) is performed by serial dilutions of cecal content samples cultured by plating under a strictly anaerobic condition. In another embodiment, the method comprises (a) obtaining a (at least one; one or more) sample, such as a fecal sample or an intestinal biopsy from a subject; (b) treating the sample of (a) with ampicillin; (c) culturing the ampicillin-treated sample of (b) and isolating pure bacterial strains.

Also provided is a method of inhibiting Th17-inducing bacterial compositions to treat autoimmune and inflammatory diseases in an individual, the method comprising administering an antibiotic, such as vancomycin and/or metronidazole to the individual.

Effects of Invention

The compositions described herein are excellent at inducing the proliferation or accumulation of T helper 17 cells (Th17 cells). Immunity in an individual can be promoted through administration of the subject composition, such as through ingestion of the bacterial composition in a food or beverage or as a dietary supplement or through administration of a pharmaceutical composition comprising the bacterial composition. The subject composition can be used, for example, to prevent or treat infectious diseases, as well as in combination with mucosal vaccines to prevent diseases caused by microorganisms or the like. In addition, if a food or beverage, such as a health food, comprises the subject composition, healthy individuals can ingest the composition easily and routinely. As a result, it is possible to induce the proliferation and/or accumulation of Th17 cells and thereby improve immune functions.

The compositions described herein provide for a potent, long-lasting, patient-friendly, and benign treatment alternative for infectious diseases. For example, infectious disease is often managed with antibiotics that may lead to antibiotic-resistance and/or opportunistic infection; systemic vaccines require extensive purification due to their injectable nature, which risks spreading blood-borne infections and are not practical for mass vaccination; existing mucosal vaccines fail to achieve sufficiently strong immune responses and are often not as stable as a live attenuated formulation.

The compositions described herein, used in combination with a mucosal vaccine antigen, can also have an effect of increasing the immune response against the antigen, or extending the duration of the immune response against the antigen, or enabling a reduction of the dose and frequency of administration of the antigen (for example, reducing the number of booster injections of antigen-containing composition) required to achieve protection, or increasing the proportion of patients achieving seroconversion, or eliciting optimal immune responses in patients in which other vaccination strategies are not effective (for example, young or aging populations).

Figure 1A:
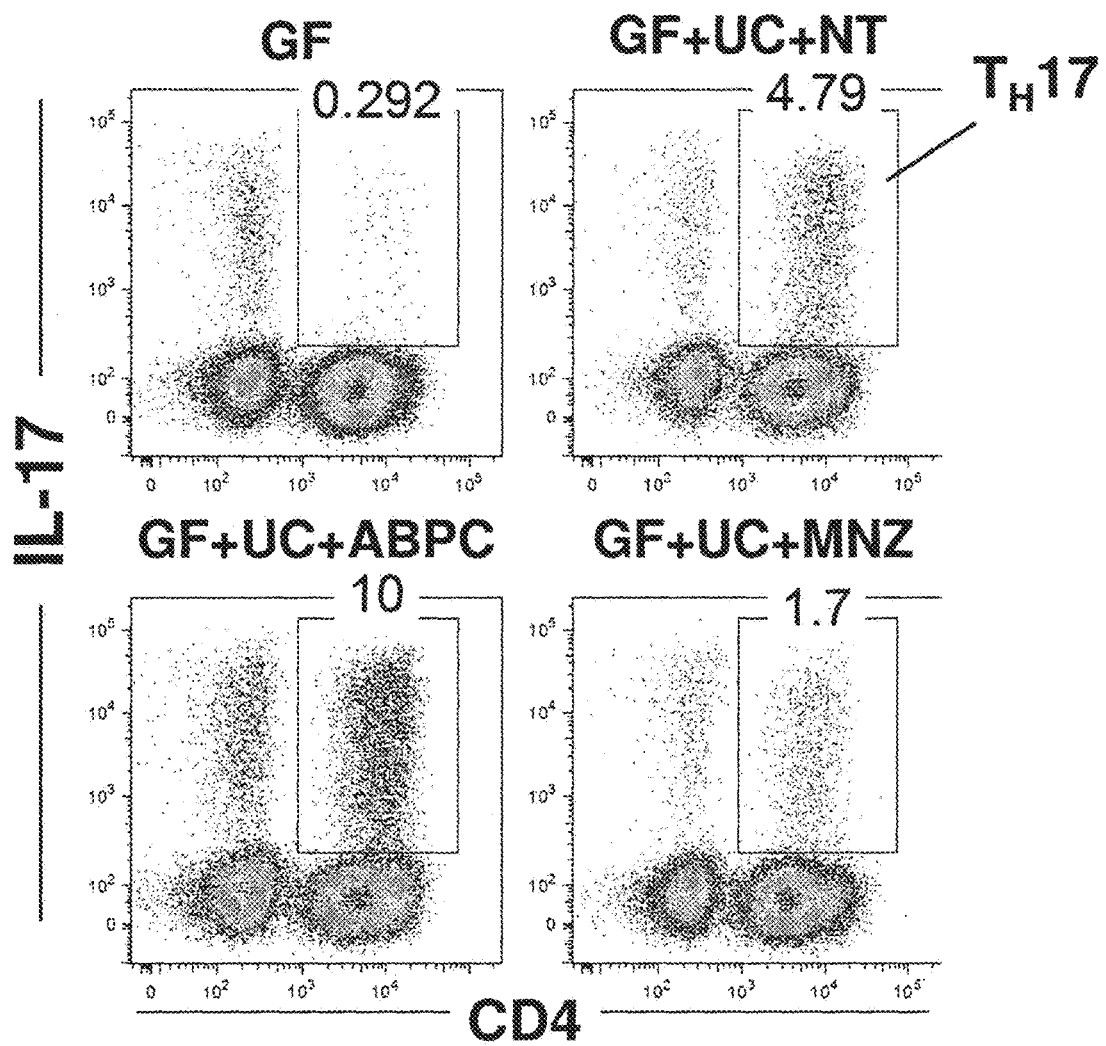
FIG. 1A is a FACS dot-plot diagram showing analysis of results of expression of IL-17 in CD4+ lymphocytes isolated from colonic lamina propia of germ-free (GF) mice (upper left panel) or GF mice colonized with stool from ulcerative colitis patients and untreated (GF+UC+NT, upper right panel), or GF mice colonized with stool from ulcerative colitis patients and treated with ampicillin in the drinking water (GF+UC+ABPC, lower left panel), or GF mice colonized with stool from ulcerative colitis patients and treated with metronidazole in the drinking water (GF+UC+MNZ, lower right panel).

Table 1 shows, for each of 20 bacterial strains isolated from the cecal contents of mice colonized with human patient stool and treated with ampicillin, the closest relative in known species from the RDP (Ribosomal Database Project) database, and the maximum similarity with the closest relative.

DESCRIPTION OF EMBODIMENTS

Recent studies have shown that individual commensal bacteria control differentiation of their specific immune cells in the mucosal immune system. For example, segmented filamentous bacteria, which are intestinal commensal bacteria in mice, induce mucosal Th17 cell response and enhance resistance against infection of gastrointestinal tracts of the host with a pathogen (NPL 11 to 13). Although specific species of murine bacterial commensals, such as segmented filamentous bacteria, that can strongly stimulate Th17 cells have been identified (NPL 11 to 13), it is still unknown whether species of human commensal bacteria exert an equivalent influence on the human immune system. Furthermore, the human intestinal tract harbors more than a thousand bacterial species, many of which have not yet been cultured (NPL 14). It is not feasible to guess a priori which ones, if any, might have an effect on Th17 cells.

In order to develop drugs, vaccines, dietary supplements, or foods with beneficial immune functions for human use, it is desirable to identify commensal microorganisms that naturally colonize humans and have immune-modulating properties. Furthermore, since many of the commensals in the human microbiome have yet to be cultured, it is necessary to develop methods to cultivate them so that they can be produced by industrial fermentation processes and subsequently incorporated in pharmaceutical or food formulations.

T helper 17 (Th17) cells are a subset of CD4+ T helper cells that provide anti-microbial immunity at mucosal surfaces, which can be critical for defense against microorganisms such as bacteria and fungi. Th17 cells depend on TGF-beta and IL-6 for differentiation and are defined by the lineage-specific transcription factor RORgt (NPL 11, 15, and 16). RORgt-expressing Th17 cells are present in large numbers in the gastrointestinal tract (NPL 6, 17). Memory CD4+ and CD8+ T cells can also be generated as a result of mucosal vaccination. In particular, memory Th17 cells with protective functions can be induced by mucosal vaccination (NPL 18).

Many infectious diseases are restricted to the mucosal membranes, or the infectious agent needs to cross the mucosal membrane during the early stages of infection. Therefore, it is desirable to obtain not only a systemic, but also a localized mucosal immune response as a result of vaccination, which can enhance protection against the infection. Vaccines administered by the mucosal route could thus be particularly effective in protecting against mucosal pathogens. However, existing mucosal vaccines are limited in their ability to promote robust immune responses at the mucosa, because exposure to antigens is not sufficiently prolonged, because the amount of antigens provided is insufficient to trigger a robust response, or because the antigens are not sufficiently immunogenic or stable. Partly because of these reasons, most vaccines used currently are still administered via the parenteral route. When host immune responses to an immunogenic antigen are too weak, it may be necessary to enhance them by co-administering an adjuvant.

Accordingly, human-derived commensal bacterial compositions with the ability to strongly induce Th17 cells are needed, as are methods to manufacture such compositions. Such compositions can be used to enable the host to mount robust immune responses against pathogenic microbes invading the body, and thus be applied as anti-infectives or as adjuvants of mucosal vaccines.

The term "T helper 17 cells (Th17 cells)" refers to T cells that promote an immune response and play a role in immune defense. Th17 cells are typically transcription factor RORgt-positive CD4-positive T cells. The Th17 cells of the present invention also include transcription factor RORgt-negative T cells that are IL-17-producing CD4-positive T cells.

The term "induces proliferation or accumulation of Th17 cells" refers to an effect of inducing the differentiation of immature T cells into Th17 cells, which differentiation leads to the proliferation and/or the accumulation of Th17 cells. Further, the meaning of "induces proliferation or accumulation of Th17 cells" includes in-vivo effects, in vitro effects, and ex vivo effects. All of the following effects are included: an effect of inducing in vivo proliferation or accumulation of Th17 cells through administration or ingestion of the aforementioned bacteria, or a culture supernatant of the bacteria or supernatant component(s); an effect of inducing proliferation or accumulation of cultured Th17 cells by causing the aforementioned bacteria or a culture supernatant of the bacteria or supernatant component(s) to act on the cultured Th17 cells; and an effect of inducing proliferation or accumulation of Th17 cells which are collected from a living organism and which are intended to be subsequently introduced into a living organism, such as the organism from which they were obtained or another organism, by causing the aforementioned bacteria, a culture supernatant of the bacteria or supernatant component(s), or a physiologically active substance derived from the bacteria to act on the Th17 cells. The effect of inducing proliferation or accumulation of Th17 cells can be evaluated, for example, as follows. Specifically, the aforementioned bacteria, a culture supernatant of the bacteria or supernatant component(s), or a physiologically active substance derived from the bacteria is orally administered to an experimental animal, such as a germ-free mouse, then CD4-positive cells in the gastrointestinal tract are isolated, and the ratio of Th17 cells contained in the CD4-positive cells is measured by flow cytometry.

The Th17 cells whose proliferation or accumulation is induced by the composition of the present invention are preferably transcription factor RORgt-positive Th17 cells or IL-17-producing Th17 cells.

In the present invention, "human-derived bacteria" means bacterial species that have been isolated from a fecal sample or from a gastrointestinal biopsy obtained from a human individual or whose ancestors were isolated from a fecal sample or from a gastrointestinal biopsy obtained from a human (e.g., are progeny of bacteria obtained from a fecal sample or a gastrointestinal biopsy). For example, the bacterial species may have been previously isolated from a fecal sample or from a gastrointestinal biopsy obtained from a human and cultured for a sufficient time to generate progeny. The progeny can then be further cultured or frozen.

In the present invention, the term "immune response" signifies any reaction produced by an antigen, such as a protein antigen, in a host having a functioning immune system. Immune responses may be humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines.

<Composition Having Effect of Inducing Proliferation or Accumulation of Th17 Cells>

Described herein is a composition that induces proliferation, accumulation of Th17 cells or both proliferation and accumulation of Th17 cells. The composition comprises, as an active ingredient, one or more of the following: an (at least one, one or more) organism (bacteria) selected from the group consisting of: *Clostridium symbiosum* (SEQ ID No 16), *Clostridium hathewayi* (SEQ ID No 12), *Clostridium citroniae* (SEQ ID No 20), *Clostridium bolteae* (SEQ ID No 19), *Ruminococcus* sp. M-1 (SEQ ID No 14), *Ruminococcus gnavus* (SEQ ID No 9), *Blautia* sp. canine oral taxon 143 (SEQ ID No 4), *Anaerostipes caccae* (SEQ ID No 18), *Clostridium lactatifermentans* (SEQ ID No 3), *Coprobacillus cateniformis* (SEQ ID No 15), *Clostridium ramosum* (SEQ ID No 1), cf. *Clostridium* sp. MLG055 (SEQ ID No 5), *Clostridium innocuum* (SEQ ID No 6), *Eubacterium desmolans* (SEQ ID No 11), *Clostridium orbiscindens* (SEQ ID No 7), *Ruminococcus* sp. 16442 (SEQ ID No 8), *Anaerotruncus colihominis* (SEQ ID No 10), *Bacteroides dorei* (SEQ ID No 17), *Bifidobacterium pseudolongum* subsp. *Pseudolongum* (SEQ ID No 2), and *Bifidobacterium breve* (SEQ ID No 13), a culture supernatant of one or more of the bacteria, a component of culture medium in which a (at least one, one or more) bacterium described herein has grown; and a (at least one; one or more) bacterium containing DNA comprising a nucleotide sequence having at least 97% homology to the nucleotide sequence of DNA of any of the bacterial species described herein, such as those listed above. Bacteria described herein were isolated from human fecal samples using the methods outlined in Examples 1 to 3.

The bacterial composition or pharmaceutical composition may include one strain alone (only one strain) of any of the bacterial species listed or described herein; two or more strains of the bacteria can be used together. For example, one, two, three, four, five, six, seven, eight, nine, ten, eleven, twelve, thirteen, fourteen, fifteen, sixteen, seventeen, eighteen, nineteen, or twenty of the strains listed in Table 1, in any combination, can be used together to affect Th17 cells.

If more than one strain of bacteria is used, the number and ratio of strains used can vary widely. The number and ratio to be used can be determined based on a variety of factors (e.g., the desired effect, such as induction or inhibition of proliferation or accumulation of Th17 cells; the disease or condition to be treated, prevented or reduced in severity; the age or gender of the recipient; the typical amounts of the strains in healthy humans). The strains can be present in a single composition, in which case they can be consumed or ingested together (in a single composition), or can be present in more than one composition (e.g., each can be in a separate composition), in which case they can be consumed individually or the compositions can be combined and the resulting combination (combined compositions) consumed or ingested. Any number or combination of the strains that proves effective (e.g., any number from one to 20, such as 1 to 20, 1 to 15, 1 to 10, 1 to 5, 1 to 3, 1 to 2, and any number therebetween can be administered. In certain embodiments of the present invention, a combination of some or all of the 20 (e.g., the 20 strains in Table 1) strains described in the present disclosure is used. For example, at least one, two or more, three, three or more, four, four or more, five, five or more, six, six or more or any other number of the 20 described strains, including 20 strains, can be used. They can be used in combination with one another and in combination with strains not described in the cited reference.

When the aforementioned bacterial compositions are cultured in a medium, substances contained in the bacteria, secretion products and metabolites produced by the bacteria are released from the bacteria. The meaning of active ingredient "culture supernatant of the bacteria" in the composition includes such substances, secretion products, and metabolites. The culture supernatant is not particularly limited, as long as the culture supernatant has the effect of inducing proliferation or accumulation of Th17 cells. Examples of the culture supernatant include a protein fraction of the culture supernatant, a polysaccharide fraction of the culture supernatant, a lipid fraction of the culture supernatant, and a low-molecular weight metabolite fraction of the culture supernatant.

The bacterial strains in the bacterial compositions may be administered in live form, or they may be administered in attenuated, inactivated, or killed form (for example, heat-killed).

The bacterial composition may be administered in the form of a pharmaceutical composition, a dietary supplement, or a food or beverage (which may also be an animal feed), or may be used as a reagent for an animal model experiment. The pharmaceutical composition, the dietary supplement, the food or beverage, and the reagent induce proliferation or accumulation of Th17 cells. Examples presented herein revealed that the bacterial composition induced Th17 cells when administered to animals. The composition of the present invention can be used suitably as a composition having an effect of promoting an immune response.

The bacterial composition of the present invention can be used, for example, as a pharmaceutical composition for preventing or treating (reducing, partially or completely the adverse effects of) an infectious disease, such as a bacterial infection, a viral infection, a parasitic infection, and a fungal infection. Oral administration of the newly identified compositions and their subsequent colonization of the gastrointestinal tract induces Th17 cells at the mucosal surface. These Th17 cells mediate protective immune responses at mucosal surfaces against a number of infectious agents, including bacteria, viruses, fungi, and parasites.

More specific examples of target infectious diseases for which the composition is useful for treatment (reducing adverse effects or prevention) include bacterial infections including but not limited to *P. aeruginosa, E. coli, C. tetani, N. gonorrhoeae, C. botulinum, Klebsiella* sp., *Serratia* sp., *Pseudomanas* sp., *P. cepacia, Acinetobacter* sp., *S. epidermis, E. faecalis, S. pneumonias, S. aureus; S. mutans, Haemophilus* sp., *Neisseria* Sp., *N. meningitides, Bacteroides* sp., *Citrobacter* sp., *Branhamella* sp., *Salmonella* sp., *Shigella* sp., *S. pyogenes, Proteus* sp., *Clostridium* sp., *Erysipelothrix* sp., *Listeria* sp., *Pasteurella multocida, Streptobacillus* sp., *Spirillum* sp., *Fusospirocheta* sp., *Treponema pallidum, Borrelia* sp., *Actinomycetes, Mycoplasma* sp., *Chlamydia* sp., *Rickettsia* sp., *Spirochaeta, Borellia burgdorferi, Legionella* sp., *Mycobacteria* sp, *Ureaplasma* sp, *Streptomyces* sp., *Trichomoras* sp., *P. mirabilis; Vibrio cholera*, enterotoxigenic *Escherichia coli, Clostridium difficile, Salmonella typhi, C. diphtheria, Mycobacterium leprae, Mycobacterium lepromatosi*; Viral infections including but not limited to picornaviridae, caliciviridae, togaviridae, flaviviridae, coronaviridae, rhabdoviridae, filoviridae, paramyxoviridae, orthomyxoviridae, bunyaviridae, arenaviridae, reoviridae, retroviridae, hepadnaviridae, parvoviridae, papovaviridae, adenoviridae, herpesviridae, poxviridae, rotavirus, parainfluenza virus, influenza virus A and B, syphilis, HIV, rabies virus, Epstein-Barr virus, and herpes simplex virus; Parasitic infections including but not limited to *Plasmodium falciparum, P. vivax, P. ovale, P. malaria, Toxoplasma gondii, Leishmania mexicana, L. tropica, L. major, L. aethiopica, L. donovani, Trypanosoma cruzi, T. brucei, Schistosoma mansoni, S. haematobium, S. japonium, Trichinella spiralis, Wuchereria bancrofti, Brugia malayli, Entamoeba histolytica, Enterobius vermiculoarus, Taenia solium, T. saginata, Trichomonas vaginatis, T. hominis, T. tenax; Giardia lamblia, Cryptosporidium parvum, Pneumocytis carinii, Babesia bovis, B. divergens, B. microti, Isospore belli,* L *hominis, Dientamoeba fragiles, Onchocerca volvulus, Ascaris lumbricoides, Necator americanis, Ancylostoma duodenale, Strongyloides stercoralis, Capillaria philippinensis, Angiostrongylus cantonensis, Hymenolepis nana, Diphyllobothrium latum, Echinococcus granulosus, E. multilocularis, Paragonimus westermani, P. caliensis, Chlonorchis sinensis, Opisthorchis felineas, G. viverini, Fasciola hepatica Sarcoptes scabiei, Pediculus humanus, Phthirius pubis,* and *Dermatobia hominis*; and Fungal infections including but not limited to *Cryptococcus neoformans, Blastomyces dermatitidis, Aiellomyces dermatitidis, Histoplasfria capsulatum, Coccidioides immitis, Candida* species, including *C. albicans, C. tropicalis, C. parapsilosis, C. guilliermondii* and *C. krusei, Aspergillus* species, including *A. fumigatus, A. flavus* and *A. niger, Rhizopus* species, *Rhizomucor* species, *Cunninghammella* species, *Apophysomyces* species, including *A. saksenaea, A. mucor* and *A. absidia, Sporothrix schenckii, Paracoccidioides brasiliensis, Pseudallescheria boydii, Torulopsis glabrata;* and *Dermatophyres* species.

The bacterial composition may be administered as an adjuvant in combination with antigenic material. The antigenic material can include one or more portions of the protein coat, protein core, or functional proteins and peptides of a pathogen, or a full pathogen (live, killed, inactivated, or attenuated), or may comprise one or a plurality of cancer epitopes or cancer antigens. The antigenic material can be co-administered, administered before, or after the bacterial composition. The bacterial composition may also be administered with existing mucosal vaccines such as influenza vaccines, (e.g. FluMist from MedImmune or NASOVAC from Serum Institute of India), rotavirus vaccines (e.g. RotaTeq from Merck or Rotarix from GlaxoSmithKline), typhoid vaccines (e.g. Vivotif from Crucell, Ty21A), cholera vaccines (e.g. Orochol from Crucell, Shanchol from Shantha Biotechnics), traveller's diarrhea vaccines (e.g. Dukoral from Crucell), and with antigens of live attenuated Influenza A virus H1 strain, live attenuated Influenza A virus H3 strain, Influenza B virus, live attenuated H1N1 influenza virus (swine flu), live attenuated rotavirus, mono- and multi-valent poliovirus, live attenuated *Salmonella typhi*, live recombinant *Vibrio cholerae* lacking cholera toxin subunit A, whole killed *Vibrio cholerae* O1 classical and El Tor biotypes with or without cholera toxin subunit B, cancer antigens, cancer epitopes, and combinations thereof.

The bacterial composition can be engineered to express specific antigens from selected pathogens or cancer antigens using genetic engineering methods well known to those skilled in the art and used, for example, as a pharmaceutical composition for prolonging exposure to said antigens and inducing stronger mucosal immune responses than oral administration of the soluble antigens alone. In one embodiment, an organism from Table 1 can be engineered by incorporation of an expression vector expressing a heterologous antigen. Said heterologous antigens may include, but are not limited to, influenza HA, NA, M2, HIV gp120, *Mycobacterium tuberculosis* Ag85B and ESAT6, *Streptococcus pneumonia* PspA, PsaA, and CbpA, respiratory syncytial virus (RSV) F and G protein, human papilloma virus protein, and cancer antigens. Furthermore, the Th-17 inducing strains can also be engineered to have a limited capacity for replication in the host, while delivering a sufficiently high antigen load at the site of immunization, so that long-term colonization by the strains is avoided.

The bacterial composition described herein and other Th17-inducing strains can be inhibited for use in preventing or treating (reducing, partially or completely, the adverse effects of) autoimmune and inflammatory diseases. Th17 cells can also have the deleterious effect of promoting chronic autoimmune and inflammatory responses in the host. Accordingly, methods of inhibiting the Th17-inducing strains via administration of molecules that impair their growth and/or function, or directly kill the Th17-inducing strains, can be used for treating autoimmune and inflammatory diseases mediated by Th17 responses. Antibiotics including, but not limited to, vancomycin and metronidazole, can be used to inhibit the Th17-inducing strains. Target diseases for which inhibition of the Th17-inducing strains is useful for treatment include: inflammatory bowel disease (IBD), ulcerative colitis, Crohn's disease, sprue, autoimmune arthritis, rheumatoid arthritis, Type I diabetes, multiple sclerosis, osteoarthritis, systemic lupus erythematosus, insulin dependent diabetes mellitus, asthma, psoriasis, atopic dermatitis, graft versus host disease, acute or chronic immune disease associated with organ transplantation, sarcoidosis, atherosclerosis, atopic allergy, food allergies such as peanut allergy, tree nut allergy, egg allergy, milk allergy, soy allergy, wheat allergy, seafood allergy, shellfish allergy, or sesame seed allergy, allergic rhinitis (pollen allergies), anaphylaxis, pet allergies, latex allergies, drug allergies, allergic rhinoconjuctivitis, eosinophilic esophagitis, and diarrhea, among others.

Pharmaceutical preparations can be formulated from the bacterial compositions described by drug formulation methods known to those of skill in the art. For example, the composition can be used orally in the form of capsules, tablets, pills, sachets, liquids, powders, granules, fine granules, film-coated preparations, pellets, troches, sublingual preparations, chewables, buccal preparations, pastes, syrups, suspensions, elixirs, and emulsions, or it can be used in a suppository or an enema.

Pharmaceutical preparations for use in mucosal vaccination can be formulated in oral form such as a solution, suspension, or emulsion in an aqueous or oil solvent, or dried as a powder. In addition, depending on the purpose, buffers, isotonizing agents, soothing agents, preservative agents, or anti-oxidants, may be added to the mucosal vaccine formulation.

For formulating these preparations, the bacterial compositions can be used in appropriate combination with carriers that are pharmacologically acceptable or acceptable for ingestion, such as in a food or beverage, including one or more of the following: sterile water, physiological saline, vegetable oil, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, a flavor corrigent, a solubilizer, and other additives.

A pharmaceutical preparation or formulation and particularly a pharmaceutical preparation for oral administration, can comprise an additional component that enables efficient delivery of the bacterial composition of the present invention to the colon, in order to more efficiently induce proliferation or accumulation of Th17 in the colon. A variety of pharmaceutical preparations that enable the delivery of the bacterial composition to the colon can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of decomposition is between about 6.8 and about 7.5. Such a numeric value range is a range in which the pH shifts toward the alkaline side at a distal portion of the stomach, and hence is a suitable range for use in the delivery to the colon.

Another embodiment of a pharmaceutical preparation useful for delivery of the bacterial composition to the colon is one that ensures the delivery to the colon by delaying the release of the contents (e.g., the bacterial composition) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Examples of the composition enabling the delivery to the colon further include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease.

The bacterial composition can be used as a food or beverage, such as a health food or beverage, a food or beverage for travelers, for infants, pregnant women, athletes, senior citizens or other specified group, a functional food, a food or beverage for specified health use, a dietary supplement, a food or beverage for patients, or an animal feed.

The addition of the bacterial composition to an antibiotic-free animal feed makes it possible to increase the body weight of an animal that ingests the animal feed to a level equal to or higher than that achieved by ingestion of antibiotic-containing animal feeds, and also makes it possible to reduce pathogenic bacteria in the gastrointestinal tract to a level equal to those in animals consuming typical antibiotic-containing animal feeds. The bacterial composition can be used as a component of an animal feed that does not need the addition of antibiotics. Animal feed comprising the bacterial composition can be fed to a wide variety of types of animals and animals of a varying ages and can be fed at regular intervals or for a certain period (for example, at birth, during weaning, or when the animal is relocated or shipped).

The bacterial active components of the bacterial composition can be manufactured using fermentation techniques. In one embodiment, the bacterial active components are manufactured using anaerobic fermentors, which can support the rapid growth of bacterial strains. The anaerobic fermentors may be, for example, stirred tank reactors or disposable wave bioreactors. Culture media such as BL agar, or similar versions of these media devoid of animal components can be used to support the growth of the bacterial species. The bacterial product can be purified and concentrated from the fermentation broth by techniques such as centrifugation and filtration, and can optionally be dried and lyophilized.

The amount of the bacterial composition to be administered or ingested can be determined empirically, taking into consideration such factors as the age, body weight, gender, symptoms, health conditions, of an individual who will receive it, as well as the kind of bacterial composition (a pharmaceutical product, a food or beverage) to be administered or ingested. For example, the amount per administration or ingestion is generally 0.01 mg/kg body weight to 100 mg/kg body weight, and, in specific embodiments, 1 mg/kg body weight to 10 mg/kg body weight. Also described herein is a method for promoting immunity (potentiating the immune response) of a subject, the method being characterized in that the bacterial compostions is administered to or ingested by the subject as described above.

The bacterial composition may be administered to an individual once, or it may be administered more than once. If the composition is administered more than once, it can be administered on a regular basis (for example, once a day, once every two days, once a week, once every two weeks, once a month, once every 6 months, or once a year) or on an as needed or irregular basis. The appropriate frequency of administration (which may depend on host genetics, age, gender, and health or disease status of the subject, among other factors) may be determined empirically. For example, a patient can be administered one dose of the composition, and the levels of the bacterial strains of the composition in fecal samples obtained from the patient can be measured at different times (for example, after 1 day, after 2 days, after 1 week, after 2 weeks, after 1 month). When the levels of the bacteria fall to, for example, one half of their maximum post-dose value, a second dose can be administered, and so on.

A product comprising the bacterial composition (a pharmaceutical product, a food or beverage, or a reagent) or a manual thereof may be accompanied by document or statement explaining that the product can be used to promote immunity (including a statement that the product has an effect of promoting immunity and a statement that the product has an effect of promoting the proliferation or function of Th17 cells). Here, the "provision to the product or the manual thereof with the note" means that the document or statement is provided to a main body, a container, a package, or the like of the product, or the note is provided to a manual, a package insert, a leaflet, or other printed matters, which disclose information on the product.

<Method for Inducing Proliferation or Accumulation of Th17 Cells>

As described above, and as shown in Examples 1 to 3, administration of the bacterial composition to an individual makes it possible to induce proliferation or accumulation of Th17 cells in the individual. This provides a method of inducing proliferation or accumulation of Th17 cells in an individual, the method comprising: administering, to the individual, at least one member selected from the group consisting of: (a) *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum*, cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum*, and *Bifidobacterium breve*; (b) a culture supernatant of at least one (a, one or more) of the bacteria described/listed herein; or a combination of (a) and (b). The bacterial composition is administered (provided) to the individual in sufficient quantity to produce the desired effect of inducing proliferation, accumulation or both proliferation and accumulation of Th17 cells. It may be administered to an individual in need of treatment or reduction in the severity of an infectious disease. It may also be administered to an individual in need of prevention of an infectious disease, as an adjuvant of a mucosal vaccine formulation.

Note that, the "individual" or "subject" (e.g., a human) may be in a healthy state or a diseased state. The method may further comprise the optional step of administering at least one (a, one or more) antibiotic preceding, or in combination with, the bacterial composition.

Moreover, a prebiotic composition can be used to favor the growth of the species in the bacterial composition over the growth of other human commensal bacterial species. In one embodiment, the prebiotic substance(s) is a nondigestible oligosaccharide. A method of inducing proliferation and/or accumulation of Th17 in an individual can comprise administering, to the individual, at least one prebiotic or at least one antibiotic in combination with the bacterial composition. Also contemplated herein is a composition comprising the bacterial composition and a prebiotic composition or an antibiotic composition.

There is no particular limitation imposed on the combined use of the therapeutic composition with at least one substance selected from the group consisting of the bacterial composition, the "mucosal vaccine formulation", the "mucosal vaccine antigen", the "antibiotic", and the "prebiotic composition". For example, the "one substance" and the therapeutic composition are administered orally or parenterally to an individual simultaneously or sequentially/individually at any appropriate time.

Whether administration of the bacterial composition induces the proliferation and/or accumulation of Th17 cells can be determined by using, as an index, increase or reinforcement of at least one of the following: the number of Th17 cells, the ratio of Th17 cells in the T cell group of the gastrointestinal tract, a function of Th17 cells, or expression of a marker of Th17 cells. A specific approach is measurement counts or percentage of RORgt-expressing Th17 cells in a patient sample, such as a biopsy or a blood sample, promotion (enhancement) of IL-17 expression, or colonization of an individual with the bacterial composition administered as the index of the induction of proliferation or accumulation of Th17 cells. Methods for detecting such expression include northern blotting, RT-PCR, and dot blotting for detection of gene expression at the transcription level; ELISA, radioimmunoassays, immunoblotting, immunoprecipitation, and flow cytometry for detection of gene expression at the translation level. Samples that may be used for measuring such an index include tissues and fluids obtained from an individual, such as blood, obtained in a biopsy, and a fecal sample.

<Method for Monitoring a Subject's Response to the Bacterial Composition>

Also provided is a method of monitoring a subject's (e.g., a human's) response to treatment with the bacterial compositions described herein, comprising: (a) obtaining a (one or more, at least one) sample, such as a fecal sample or a colonic biopsy from a patient before treatment with a bacterial composition described herein; (b) obtaining, a (one or more, at least one) corresponding sample from the patient after treatment with a bacterial composition described herein; and (c) comparing the percentage or absolute counts of at least one bacterial species selected from the group consisting of: *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum,* cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum,* and *Bifidobacterium breve* in the sample obtained in (a) with the percentage or absolute counts of the same at least one bacterial species in the sample obtained in (b), wherein a higher value in the sample obtained in (b) (after treatment with the bacterial composition) than in the sample obtained in (a) (before treatment) indicates that the subject has responded favorably to treatment (e.g., is a positive indicator of enhanced immune response in the subject). In some embodiments, the method further comprises (d) further administering the bacterial composition to the patient or ceasing administration of the bacterial composition to the patient based on the comparison in (c). In the monitoring method described herein, a variety of known methods can be used for determining the percentage or absolute counts of a bacterial species. For example, 16S rRNA sequencing can be used.

<Method to Obtain Th17-Inducing Bacterial Compositions>

Certain modifications applied to a fecal sample can result in the obtention of Th17-inducing bacterial compositions. Surprisingly, administration of ampicillin to animals enriches the representation of Th17-inducing strains in a sample. Culturing serially diluted samples from ampicillin-treated animals by plating under strictly anaerobic conditions in certain media described in Example 2 led to obtention of potent Th17-inducing bacterial compositions. Accordingly, provided is a method of obtaining Th17-inducing bacterial compositions, comprising (a) treating a subject with the antibiotic ampicillin, or an antibiotic with a similar spectrum, for example an aminopenicillin family member such as amoxicillin, penicillin, or benzylpenicillin; (b) obtaining (a, one or more, at least one) sample, such as a fecal sample or an intestinal biopsy from the subject; (c) culturing the sample from (b) and isolating pure bacterial strains from the resulting colonies. In a preferred embodiment the subject in (a) is an ex-germ-free animal that is first colonized with a fecal sample obtained from a human donor, and afterwards is treated with ampicillin, after which cecal samples are obtained from the animal and cultured as described in Example 2. In one embodiment, the isolation of pure bacterial strains of (c) is performed by serial dilutions of cecal content samples cultured by plating under a strictly anaerobic condition. In another embodiment, the method comprises (a) obtaining (at least one) sample, such as a fecal sample or an intestinal biopsy from a subject; (b) treating the sample of (a) with ampicillin; (c) culturing the ampicillin-treated sample of (b) and isolating pure bacterial strains.

<Method of Use of the Th17-Inducing Bacterial Compositions to Repopulate the Microbiota of Individuals Receiving Antibiotic Treatment>

The bacterial composition can be administered to an individual who is also receiving antibiotic treatment. The present inventors have demonstrated that antibiotics such as vancomycin or metronidazole can effectively eliminate or greatly reduce Th17-inducing bacterial species from the gastrointestinal tract of mammals and subsequently decrease the levels of Th17 cells (Example 1). Without wishing to be bound by theory, the key role of Th17-inducing bacteria promoting immune responses strongly indicates that their presence or high levels can play a key role in autoimmune diseases. Accordingly, individuals undergoing courses of antibiotics such as vancomycin or metronidazole, who are at a high risk of experiencing a loss of Th17-inducing bacteria and thus experience immune deficits, can be preventively "repopulated" through use of the bacterial compositions. The bacterial compositions can be administered before, simultaneously with, or after the antibiotic treatment, but preferably are administered simultaneously or after the antibiotic treatment.

Following are examples, which describe specific aspects. They are not intended to be limiting in any way.

EXAMPLES

Example 1

Human stool (2 g) from an ulcerative colitis (UC) Japanese patient in a clinically active state was suspended with 8 ml phosphate-buffered saline (PBS) containing 20% glycerol, snap-frozen in liquid nitrogen, and stored at −80° C. until use. The frozen stock was thawed, and orally inoculated into IQI germ-free (GF) mice (250 μl/mouse). The mice were given ampicillin (ABPC; 1 g/L), vancomycin (VCM; 500 mg/L), polymyxin B (PL-B; 200 mg/L), metronidazole (MNZ; 1 g/L), or water only (non-treated: NT) in their drinking water beginning 1 d after the inoculation with UC patient feces until the day of analysis. Each group of ex-GF mice (n=5 for each group) was separately kept in a vinyl isolator for 4 weeks.

The colons were collected and opened longitudinally, washed with PBS to remove all luminal contents and shaken in Hanks' balanced salt solution (HBSS) containing 5 mM EDTA for 20 min at 37° C. After removing epithelial cells, muscle layers and fat tissue using forceps, the lamina propria layers were cut into small pieces and incubated with RPMI1640 containing 4% fetal bovine serum (FBS), 0.5 mg/mL collagenase D, 0.5 mg/mL dispase and 40 mg/mL DNase I (all Roche Diagnostics) for 1 h at 37° C. in a shaking water bath. The digested tissues were washed with HBSS containing 5 mM EDTA, resuspended in 5 mL of 40% Percoll (GE Healthcare) and overlaid on 2.5 ml of 80% Percoll in a 15-ml Falcon tube. Percoll gradient separation was performed by centrifugation at 800 g for 20 min at 25° C. The lamina propria lymphocytes were collected from the interface of the Percoll gradient and suspended in RPMI1640 containing 10% FBS. For analysis of Th1 and Th17 cells, isolated lymphocytes were stimulated for 4 h with 50 ng/mL phorbol 12-myristate 13-acetate (PMA, Sigma) and 750 ng/mL ionomycin (Sigma) in the presence of GolgiStop (BD Biosciences). After incubation for 4 h, cells were washed in PBS, labelled with the LIVE/DEAD fixable dead cell stain kit (Invitrogen) and surface CD4 and CD3 were stained with PECy7-labelled anti-CD4 Ab (RM4-5, BD Biosciences) and BV605-labelled anti-CD3 Ab (17A2, BioLegend). Cells were washed, fixed and permeabilized with Foxp3 Staining Buffer set (eBioscience), and stained with the APC-labelled anti-IL-17 Ab (eBio17B7, eBioscience) and BV421-labelled anti-IFN-g Ab (XMG1.2, BioLegend). The Ab stained cells were analyzed with LSR Fortessa (BD Biosciences), and data were analyzed using FlowJo software (Treestar).

Figure 1B:
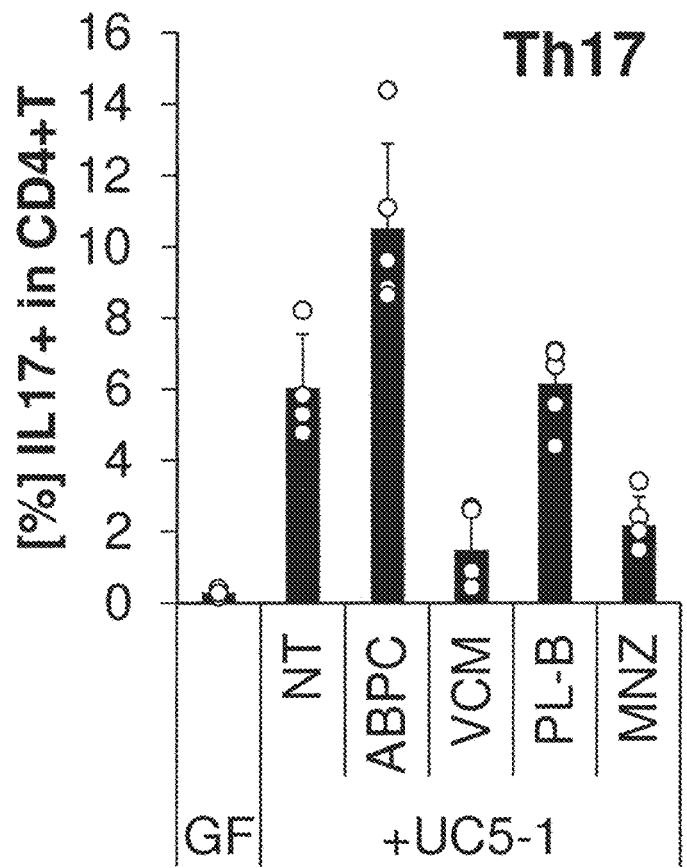
FIG. 1B is a graph showing analysis results of the ratios of IL-17+ cells in CD4+ lymphocytes of germ-free mice (GF), GF mice colonized with stool from ulcerative colitis patients and untreated (NT), and GF mice colonized with stool from ulcerative colitis patients and treated with ampicillin (ABPC) or vancomycin (VCM) or polymyxin-B (PL-B) or metronidazole (MNZ) in the drinking water.

In mice orally inoculated with UC patient feces, substantial induction of Th17 cells was observed. Surprisingly, the Th17 induction was enhanced in mice given ampicillin (ABPC) in the drinking water, compared with mice given water only (non-treated: NT). In contrast, Th17 induction was significantly impaired by the treatment with vancomycin (VCM) or metronidazole (MNZ). On the other hand, treatment with polymyxin B (PL-B) did not affect Th17 cell numbers (FIG. 1).

Therefore, Th17-inducing bacteria are present in the human feces, and the bacterial species are resistant to ampicillin and polymyxin B, but sensitive to vancomycin and metronidazole.

Example 2

The caecal contents from each exGF mice described in Example 1 were suspended in 10 mL of Tris-EDTA containing 10 mM Tris-HCl and 1 mM EDTA (pH 8), and incubated with Lysozyme (SIGMA, 15 mg/mL) at 37° C. for 1 h with gentle mixing. A purified achromopeptidase (Wako) was added (final concentration 2000 unit/mL) and incubated at 37° C. for another 30 min. Then, sodium dodecyl sulfate (final concentration 1%) was added to the cell suspension and mixed well. Subsequently, proteinase K (Merck) was added (final concentration 1 mg/mL) to the suspension and the mixture was incubated at 55° C. for 1 h. High-molecular-weight DNA was isolated and purified by phenol/chloroform extraction, ethanol, and finally polyethyleneglycol precipitation. PCR was performed using Ex Taq (TAKARA) and (i) modified primer 8F [5'-CCATCT-CATCCCTGCGTGTCTCCGACTCAG (454 adaptor sequence, SEQ ID NO.: 21)+Barcode (10 bases)+AGRGTTTGATYMTGGCTCAG (SEQ ID NO.: 22)-3'] and (ii) modified primer 338R [5'-CC-TATCCCTGTGTGCCTTGGCAGTCTCAG (454 adaptor sequence, SEQ ID NO.: 23)+TGCTGCCTCCCGTAG-GAGT (SEQ ID NO.: 24)-3'] to the V1-V2 region of the 16S rRNA gene. Amplicons generated from each sample (~330 bp) were subsequently purified using AMPure XP (BECKMAN COULTER). The amount of DNA was quantified using Quant-iT Picogreen dsDNA Assay Kit (Invitrogen) and TBS-380mini Fluorometer (Turner Biosystems). Then, the amplified DNA was used as template for IonPGM sequencer. Resulting sequences (3000 reads were produced for each sample) were classified into OTUs based on sequence similarity (≥96% identity). Representative sequences from each OTU were compared with sequences in nucleic acid databases (Ribosomal Database Project) or GenomeDB (NCBI+HMP+Hattori Lab data base) using BLAST to determine the closest strains.

Figure 2:
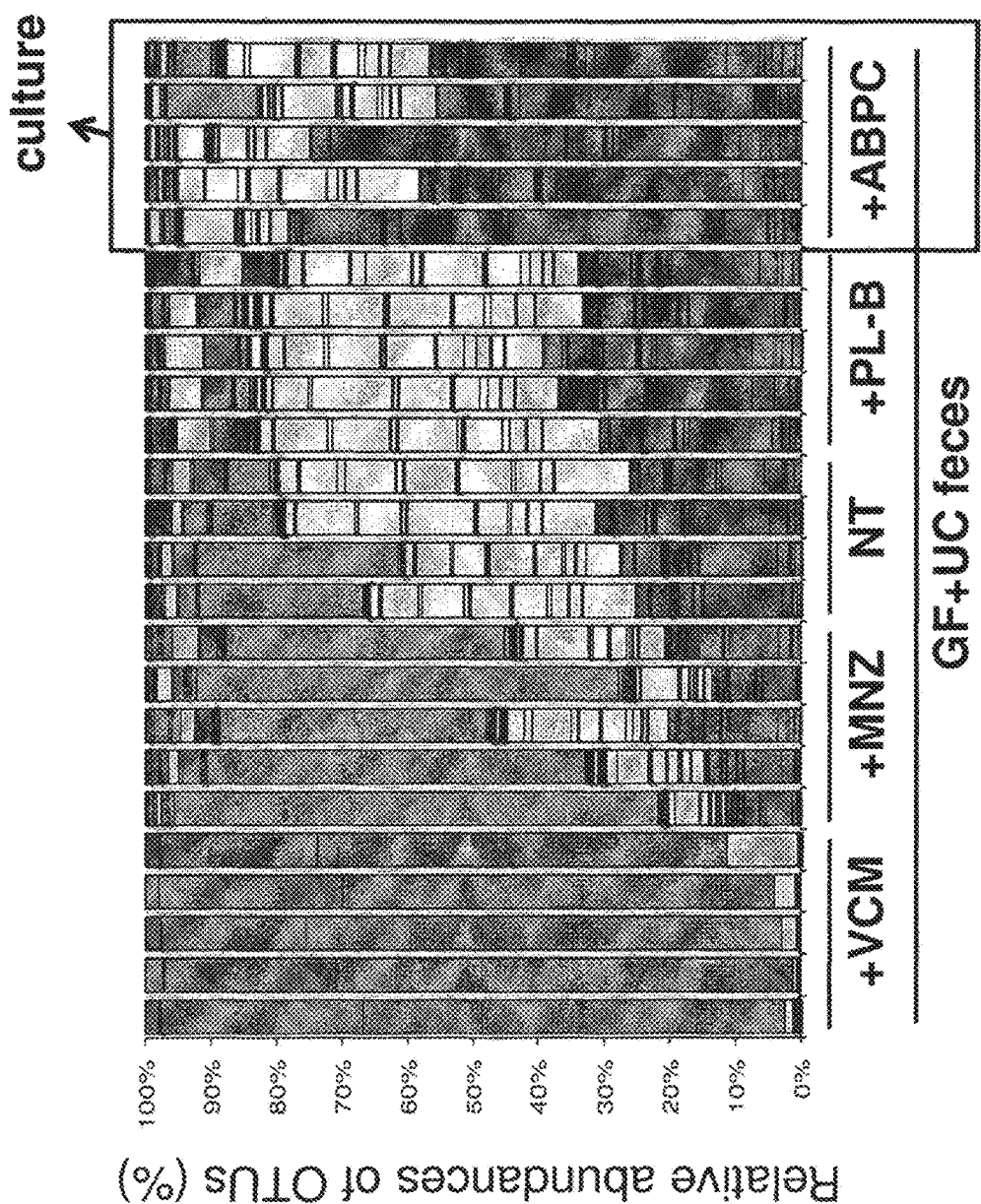
FIG. 2 shows the relative abundance of OTUs having the same closest relative in cecal samples from IQI Germ Free mice colonized with human stool from an ulcerative colitis patient and given water only (non-treated: NT) or given ampicillin (+ABPC; 1 g/L), or vancomycin (+VCM; 500 mg/L), or polymyxin B (+PL-B; 200 mg/L), or metronidazole (+MNZ; 1 g/L) in the drinking water; n=5 for each group. OTUs negatively correlated with Th17 cell number are depicted in blue or grey, and OTUs positively correlated with Th17 cell number are marked with red.

OTUs negatively correlated with Th17 cell number are depicted in FIG. 2 in blue or grey, and OTUs positively correlated with Th17 cell number are marked with red.

Serial dilutions of the cecal contents from mice colonized with UC patient feces and given ampicillin were cultured by plating under a strictly anaerobic condition (80% $N_2$ 10% $H_2$ 10% $CO_2$) on BL agar (Eiken Chemical) supplemented with 5% defibrinated horse blood (Nippon Bio-Supp. Center), GAM agar (Nissui) supplemented with 5% defibrinated horse blood, Tryptic soy agar (Becton Dickinson) supplemented with 5% defibrinated horse blood, Reinforced clostridial agar (Oxoid) supplemented with 5% defibrinated horse blood, Schaedler agar (Becton Dickinson) or Brain Heart Infusion agar (Becton Dickinson). After culture at 37° C. for 2 days, each single colony was picked up (250 colonies in total) and stocked in Schaedler Broth (Becton Dickinson) containing 10% glycerol at −80° C. To identify the isolated strains, the 16S rRNA genes were amplified by colony-PCR using KOD FX (TOYOBO) and 16S rRNA gene-specific primer pairs: 8F (5'-AGAGTTT-GATCMTGGCTCAG-3') (SEQ ID NO.: 25) and 1492R (5'-GGYTACCTTGTTACGACTT-3') (SEQ ID NO.: 26). The amplification program consisted of one cycle at 98° C. for 2 min, followed by 35 cycles at 98° C. for 10 s, 57° C. for 30 s and 68° C. for 90 s. Each amplified DNA was purified from the reaction mixture using AMPure XP. Sequence analysis was performed using BigDye Terminator V3.1 Cycle Sequencing Kit (Applied Biosystems) and Applied Biosystems 3730x1 DNA analyzer (Applied Biosystems). The resulting sequences were compared with sequences in the RDP database to determine the closest relatives. BLAST search of 16S rRNA gene sequences of these picked-up colonies revealed that we succeeded in isolating 20 strains (Table 1).

Example 3

Figure 3A:
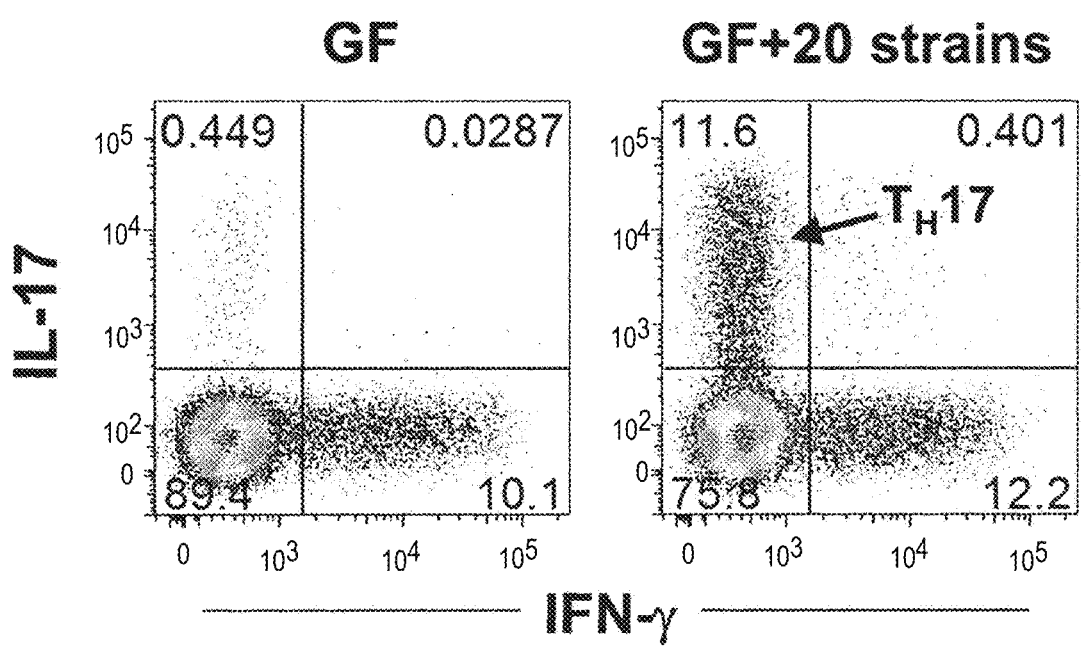
FIG. 3A shows the percentages of IL-17+ cells and IFN-g+ within the CD4+ T cell population in the colon lamina propria of germ-free mice and germ-free mice colonized with the 20 strains listed in Table 1.
Figure 3B:
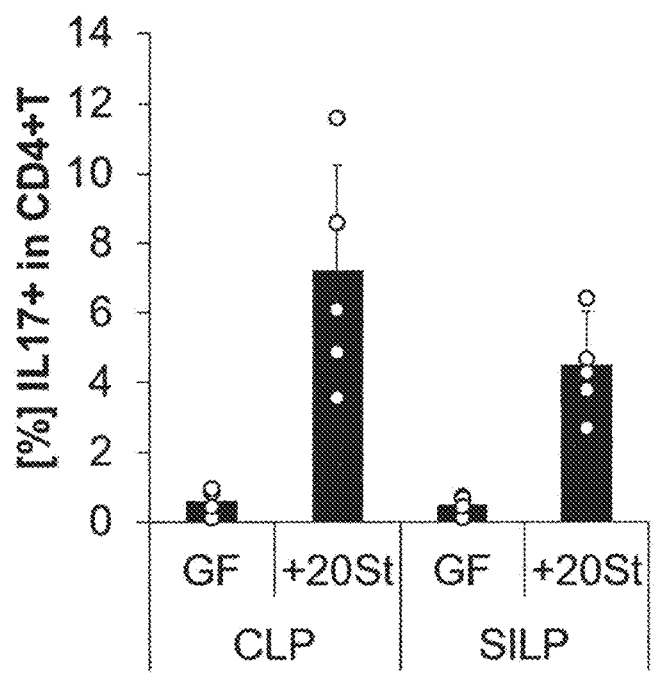
FIG. 3B is a graph showing analysis results of the ratios of IL-17+ cells in CD4+ lymphocytes in the Colon Lamina Propria (CLP) or Small Intestine Lamina Propria (SILP) of germ-free mice compared to germ-free mice colonized with the 20 strains listed in Table 1.

To investigate whether the isolated 20 strains (Table 1) have the ability to induce Th17 cells, all 20 strains were cultured and mixed to make a cocktail, and the cocktail was orally inoculated into GF mice. The isolated 20 strains were individually cultured in Schaedler or PYG broth under a strictly anaerobic condition (80% $N_2$, 10% $H_2$, 10% $CO_2$) at 37° C. in an anaerobic chamber (Coy Laboratory Products), and then mixed at equal amounts of media volume to prepare the bacterial mixture. The aliquot of bacterial mixture was orally inoculated into mice (0.5 ml/mouse). After 4 weeks, the colons and small intestines were collected and analyzed for Th17 and Th1 cells. The percentages of IL-17+ cells and IFN-g+ within the CD4+ T cell population in the colon lamina propria and small intestine lamina propria of the indicated mice are shown in FIG. 3. In mice colonized with the 20 strains, a strong induction of Th17 cells was observed. SEQ ID Nos.: 2H6, 1B11, 1D10, 2E3, 1C12, 2G4, 2H11, 1E11, 2D9, 2F7, 1D1, 1F8, 1C2, 1D4, 1E3, 1A9, 2G11, 2E1, 1F7, 1D2, are SEQ ID Nos. 1-20 respectively.

INDUSTRIAL APPLICABILITY

As has been described above, the compositions and methods described herein make it possible to provide an excellent and well-characterized composition for inducing proliferation or accumulation of Th17 by utilizing certain human-derived bacteria or supernatants or the like derived from the bacteria. Since the bacterial composition has the effects of promoting immune responses, the bacterial composition can be used, for example, to treat infections, as well as to prevent infections as a component of a mucosal vaccine. In addition, healthy individuals can easily and routinely ingest the bacterial composition, such as in food or beverage, (e.g., a health food), to improve their immune functions.

This application is based on U.S. provisional patent application No. 61/978,182 (filing date: Apr. 10, 2014), the contents of which are incorporated in full herein.

TABLE 1

| SEQ ID# | strain# | identity | species |
|---|---|---|---|
| 1 | 2H6 | 0.975 | Clostridium ramosum |
| 2 | 1B11 | 1.000 | Bifidobacterium pseudolongum subsp. pseudolongum |
| 3 | 1D10 | 0.962 | Clostridium lactatifermentans |
| 4 | 2E3 | 0.777 | Blautia sp. canine oral taxon 143 |
| 5 | 1C12 | 0.926 | cf. Clostridium sp. MLG055 |
| 6 | 2G4 | 0.995 | Clostridium innocuum |
| 7 | 2H11 | 0.999 | Clostridium orbiscindens |
| 8 | 1E11 | 0.941 | Ruminococcus sp. 16442 |
| 9 | 2D9 | 0.954 | Ruminococcus gnavus |
| 10 | 2F7 | 0.749 | Anaerotruncus colihominis |
| 11 | 1D1 | 0.857 | Eubacterium desmolans |
| 12 | 1F8 | 0.959 | Clostridium hathewayi |
| 13 | 1C2 | 0.993 | Bifidobacterium breve |
| 14 | 1D4 | 0.959 | Ruminococcus sp. M-1 |
| 15 | 1 E3 | 0.977 | Coprobacillus cateniformis |
| 16 | 1A9 | 0.967 | Clostridium symbiosum |
| 17 | 2G11 | 0.991 | Bacteroides dorei |
| 18 | 2E1 | 0.964 | Anaerostipes caccae |
| 19 | 1F7 | 0.958 | Clostridium bolteae |
| 20 | 1D2 | 0.783 | Clostridium citroniae |

TABLE 2

```
>2H6(SEQ ID NO.: 1)
GGGGCGGCTGCTATAATGCAGTCGACGCGAGCACTTGTGCTCGAGTGGC
GAACGGGTGAGTAATACATAAGTAACCTGCCCTAGACAGGGGATAACT
ATTGGAAACGATAGCTAAGACCGCATATGTACGGACACTGCATGGTGAC
CGTATTAAAAGTGCCTCAAAGCACTGGTAGAGGATGGACTTATGGCGCA
TTAGCTGGTTGGCGGGGTAACGGCCCACCAAGGCGACGATGCGTAGCCG
ACCTGAGAGGGTGACCGGCCACACTGGGACTGAGACACGGCCCAGACTC
CTACGGGAGGCAGCAGTAGGGAATTTTCGGCAATGGGGGAAACCCTGAC
```

TABLE 2-continued

```
CGAGCAACGCCGCGTGAAGGAAGAAGGTTTTCGGATTGTAAACTTCTGT
TATAAAGGAAGAACGGCGGCTACAGGAAATGGTAGCCGAGTGACGGTAC
TTTATTAGAAAGCCACGGCTAACTACGTGCCAGCAGCCGCGGTAATACG
TAGGTGGCAAGCGTTATCCGGAATTATTGGGCGTAAAGAGGGAGCAGGC
GGCAGCAAGGGTCTGTGGTGAAAGCCTGAAGCTTAACTTCAGTAAGCCA
TAGAAACCAGGCAGCTAGAGTGCAGGAGAGGATCGTGGAATTCCATGTG
TAGCGGTGAAATGCGTAGATATATGGAGGAACACCAGTGGCGAAGGCGA
CGATCTGGCCTGCAACTGACGCTCAGTCCCGAAAGCGTGGGGAGCAAAT
AGGATTAGATACCCTAGTAGTCCACGCCGTAAACGATGAGTACTAAGTG
TTGGATGTCAAAGTTCAGTGCTGCAGTTAACGCAATAAGTACTCCGCCT
GAGTAGTACGTTCGCAAGAATGAAACTCAAAGGAATTGACGGGGCCCG
CACAAGCGGTGGAGCATGTGGTTTAATTCGAAGCAACGCGAAGAACCTT
ACCAGGTCTTGACATACTCATAAAGGCTCCAGAGATGGAGAGATAGCTA
TATGAGATACAGGTGGTGCATGGTTGTCGTCAGCTCGTGTCGTGAGATG
TTGGGTTAAGTCCCGCAACGAGCGCAACCCTTATCGTTAGTTACCATCA
TTAAGTTGGGGACTCTAGCGAGACTGCCAGTGACAAGCTGGAGGAAGGC
GGGGATGACGTCAAATCATCATGCCCCTTATGACCTGGGCTACACACGT
GCTACAATGGATGGTGCAGAGGGAAGCGAAGCCGCGAGGTGAAGCAAAA
CCCATAAAACCATTCTCAGTTCGGATTGTAGTCTGCAACTCGACTACAT
GAAGTTGGAATCGCTAGTAATCGCGAATCAGCATGTCGCGGTGAATACG
TTCTCGGGCCTTGTACACACCGCCCGTCACACCACGAGAGTTGATAACA
CCCGAAGCCGGTGGCCTAACCGCAAGGAAGGAGCTTCTAAGGTGGAT
```

TABLE 3

```
>1B11(SEQ ID NO.: 2)
CTGCGGCGTCTACCATGCAGTCGAACGGGATCCCTGGCAGCTTGCTGCC
GGGGTGAGAGTGGCGAACGGGTGAGTAATGCGTGACCGACCTGCCCCAT
GCACCGGAATAGCTCCTGGAAACGGGTGGTAATGCCGGATGTTCCACAT
GAGCGCATGCGAGTGTGGGAAAGGCTTTTTGCGGCATGGGATGGGGTCG
CGTCCTATCAGCTTGTTGGTGGGGTAACGGCCTACCAAGGCGTTGACGG
GTAGCCGGCCTGAGAGGGCGACCGGCCACATTGGGACTGAGATACGGCC
CAGACTCCTACGGGAGGCAGCAGTGGGGAATATTGCACAATGGGCGAA
GCCTGATGCAGCGACGCCGCGTGCGGGATGGAGGCCTTCGGGTTGTAAA
CCGCTTTTGTTCAAGGGCAAGGCACGGTCTTTGGCCGTGTTGAGTGGAT
TGTTCGAATAAGCACCGGCTAACTACGTGCCAGCAGCCGCGGTAATACG
TAGGGTGCAAGCGTTATCCGGATTTATTGGGCGTAAAGGGCTCGTAGGC
GGTTCGTCGCGTCCGGTGTGAAAGTCCATCGCTTAACGGTGGATCCGCG
CCGGGTACGGCGGGCTTGAGTGCGGTAGGGGAGACTGGAATTCCCGGT
GTAACGGTGGAATGTGTAGATATCGGGAAGAACACCAATGGCGAAGGCA
GGTCTCTGGGCCGTTACTGACGCTGAGGAGCGAAAGCGTGGGGAGCGAA
CAGGATTAGATACCCTGGTAGTCCACGCCGTAAACGGTGGATGCTGGAT
GTGGGGCCCTTTTTCCGGGTCCTGTGTCGGAGCTAACGCGTTAAGCATC
CCGCCTGGGGAGTACGGCCGCAAGGCTAAAACTCAAAGAAATTGACGGG
GGCCCGCACAAGCGGCGGAGCATGCGGATTAATTCGATGCAACGCGAAG
AACCTTACCTGGGCTTGACATGTGCCGGACGCCCGCGGAGACGCGGGTT
CCCTTCGGGGCCGGTTCACAGGTGGTGCATGGTCGTCGTCAGCTCGTGT
CGTGAGATGTTGGGTTAAGTCCCGCAACGAGCGCAACCCTCGCCGCGTG
TTGCCAGCGGGTCATGCCGGGAACTCACGTGGGACCGCCGGGGTTAACT
CGGAGGAAGGTGGGGATGACGTCAGATCATCATGCCCCTTACGTCCAGG
GCTTCACGCATGCTACAATGGCCGGTACAACGGGGTGCGACACGGTGAC
GTGGGGCGGATCCCTGAAAACCGGTCTCAGTTCGGATCGCAGTCTGCAA
CTCGACTGCGTGAAGGTGGAGTCGCTAGTAATCGCGGATCAGCAACGCC
GCGGTGAATGCGTTCCCGGGCCTTGTACACACCGCCCGTCAAGTCATGA
AAGTGGGCAGCACCCGAAGACGGTGGCCTAACCCTTGTGGGGGAGCCG
TCTAAGGTAGTG
```

TABLE 4

```
>1D10(SEQ ID NO.: 3)
CTGCCGGCTCTACCATGCAGTCGAACGAAGATAGTTAGAATGAGAGCTT
CGGCAGGATTTTTTTCTATCTTAGTGGCGGACGGGTGAGTAACGTGTGG
GCAACCTGCCCTGTACTGGGGAATAATCATTGGAAACGATGACTAATAC
CGCATGTGGTCCTCGGAAGGCATCTTCTGAGGAAGAAAGGATTTATTCG
GTACAGGATGGGCCCGCATCTGATTAGCTAGTTGGTGAGATAACAGCCC
ACCAAGGCGACGATCAGTAGCCGACCTGAGAGGGTGATCGGCCACATTG
GGACTGAGACACGGCCCAAACTCCTACGGGAGGCAGCAGTGGGGAATAT
TGCACAATGGGCGAAAGCCTGATGCAGCAACGCCGCGTGAAGGATGAAG
GTTTCGGCTCGTAAACTTCTATCAATAGGGAAGAAACAAATGACGGTA
CCTAAATAAGAAGCCCCGGCTAACTACGTGCCAGCAGCCGCGGTAATAC
GTAGGGGGCAAGCGTTATCCGGAATTACTGGGTGTAAAGGGAGCGTAGG
CGGCATGGTAAGCCAGATGTGAAAGCCTTGGGCTTAACCGAGGATTGC
ATTTGGAACTATCAAGCTAGAGTACAGGAGAGGAAAGCGGAATTCCTAG
TGTAGCGGTGAAATGCGTAGATATTAGGAAGAACACCAGTGGCGAAGGC
GGCTTTCTGGACTGAAACTGACGCTGAGGCTCGAAAGCGTGGGGAGCAA
```

TABLE 4-continued

```
ACAGGATTAGATACCCTGGTAGTCCACGCCGTAAACGATGAGTGCTAGG
TGTCGGGGAGGAATCCTCGGTGCCGCAGCTAACGCAATAAGCACTCCAC
CTGGGGAGTACGACCGCAAGGTTGAAACTCAAAGGAATTGACGGGGGCC
CGCACAAGCGGTGGAGCATGTGGTTTAATTCGAAGCAACGCGAAGAACC
TTACCAAGGCTTGACATCCCGATGACCGTCCTAGAGATAGGACTTCTCT
TCGGAGCATCGGTGACAGGTGGTGCATGGTTGTCGTCAGCTCGTGTCGT
GAGATGTTGGGTTAAGTCCCGCAACGAGCGCAACCCTTATCTTCAGTAG
CCATCATTCAGTTGGGCACTCTGGAGAGACTGCCGTGGATAACACGGAG
GAAGGTGGGGATGACGTCAAATCATCATGCCCCTTATGTCTTGGGCTAC
ACACGTGCTACAATGGCTGGTAACAAAGTGACGCGAGACGGCGACGTTA
AGCAAATCACAAAAACCCAGTCCCAGTTCGGATTGTAGTCTGCAACTCG
ACTACATGAAGCTGGAATCGCTAGTAATCGCGAATCAGCATGTCGCGGT
GAATACGTTCCCGGGCCTTGTACACACCGCCCGTCACACCATGGGAGTT
GGAAGCACCCGAAGTCGGTGACCTAACCGTAAGGAAGAGCCGCCGAAGT
AGGGGAT
```

TABLE 5

>2E3(SEQ ID NO.: 4)
```
CGGCGCTCTACCATGCAGTCGACGAAGCGATTTGAATGAAGTTTTCGGA
TGGATTTTAAATTGACTGAGTGGCGGACGGGTGAGTAACGCGTGGGTAA
CCTGCCCCATACAGGGGGATAACAGTTAGAAATGACTGCTAATACCGCA
TAAGACCACAGCGCCGCATGGTGCAGGGGTAAAAACTCCGGTGGTATGG
GATGGACCCGCGTCTGATTAGCTTGTTGGCGGGTAACGGCCCACCAAG
GCGACGATCAGTAGCCGACCTGAGAGGGTGACCGGCCACATTGGGACTG
AGACACGGCCCAAACTCCTACGGGAGGCAGCAGTGGGGAATATTGCACA
ATGGGGGAAACCCTGATGCAGCGACGCCGCGTGAGTGATGAAGTATTTC
GGTATGTAAAGCTCTATCAGCAGGGAAGAAAATGACGGTACCTGACTAA
GAAGCCCCGGCTAACTACGTGCCAGCAGCCGCGGTAATACGTAGGGGGC
AAGCGTTATCGGATTTACTGGGTGTAAAGGGAGCGTAGACGGCTGTGC
AAGTCTGGAGTGAAAGCCCGGGGCTCAACCCCGGGACTGCTTTGGAAAC
TGTACGGCTGGAGTGCTGGAGAGGCAAGCGGAATTCCTAGTGTAGCGGT
GAAATGCGTAGATATTAGGAGGAACACCAGTGGCGAAGGCGGCTTGCTG
GACAGTAACTGACGTTGAGGCTCGAAAGCGTGGGGAGCAAACAGGATTA
GATACCCTGGTAGTCCACGCCGTAAACGATGAATGCTAGGTGTCGGGGA
GCAAAGCTCTTCGGTGCCGCCGCAAACGCAATAAGCATTCCACCTGGGG
AGTACGTTCGCAAGAATGAAACTCAAAGGAATTGACGGGGACCCGCACA
AGCGGTGGAGCATGTGGTTTAATTCGAAGCAACGCGAAGAACCTTACCA
AGTCTTGACATCCCCCTGACCGGCAAGTAATGTCGCCTTTCCTTCGGGA
CAGGGGAGACAGGTGGTGCATGGTTGTCGTCAGCTCGTGTCGTGAGATG
TTGGGTTAAGTCCCGCAACGAGCGCAACCCTTATCCTCAGTAGCCAGCA
GGTGACTGGGCACTCTGTGGAGACTGCCAGGGATAACCTGGAGGAAG
GTGGGGACGACGTCAAATCATCATGCCCCTTATGACTTGGGCTACACAC
GTGCTACAATGGCGTAAACAAAGGGAAGCGAGAGGGTGACCTGGAGCAA
ATCCCAAAAATAACGTCTCAGTTCGGATTGTAGTCTGCAACTCGACTAC
ATGAAGCTGGAATCGCTAGTAATCGCGAATCAGCATGTCGCGGTGAATA
CGTTCCCGGGTCTTGTACACACCGCCCGTCACACCATGGGAGTCAGCAA
CGCCCGAAGCCGGTGACCTAACCGCAAGGAAGGAGCCGTCGAAGTCGTC
G
```

TABLE 6

>1C12(SEQ ID NO.: 5)
```
CGGCGCTGCTATACTGCAGTCGAACGAAGCGAAGGTAGCTTGCTATCGG
AGCTTAGTGGCGAACGGGTGAGTAACACGTAGATAACCTGCCTGTATGA
CCGGGATAACAGTTGGAAACGACTGCTAATACCGGATAGGCAGAGAGGA
GGCATCTCTTCTCTGTTAAAGTTGGGATACAACGCAAACAGATGGATCT
GCGGTGCATTAGCTAGTTGGTGGGTAACGGCCCACCAAGGCGATGATG
CATAGCCGGCCTGAGAGGGTGAACGGCCACATTGGGACTGAGACACGGC
CCAAACTCCTACGGGAGGCAGCAGTAGGGAATTTTCGGCAATGGGGGAA
ACCCTGACCGAGCAATGCCGCGTGAGTGAAGACGGCCTTCGGGTTGTAA
AGCTCTGTTGTAAGGGAAGAACGGCATAGAGAGGGAATGCTCTATGAGT
GACGGTACCTTACCAGAAAGCCACGGCTAACTACGTGCCAGCAGCCGCG
GTAATACGTAGGTGGCAAGCGTTATCCGGAATTATTGGGCGTAAAGGGT
GCGTAGGCGGCTGGATAAGTCTGAGGTAAAAGCCCGTGGCTCAACCACG
GTAAGCTTGGAAACTGTCTGGCTGGAGTGCAGGAGAGGACAATGGAAT
TCCATGTGTAGCGGTAAAATGCGTAGATATATGGAGGAACACCAGTGGC
GAAGGCGGTTGTCTGGCCTGTAACTGACGCTGAAGCACGAAAGCGTGGG
GAGCAAATAGGATTAGATACCCTAGTAGTCCACGCCGTAAACGATGAGA
ACTAAGTGTTGGGGAAACTCAGTGCTGCAGTTAACGCAATAAGTTCTCC
GCCTGGGGAGTATGCACGCAAGTGTGAAACTCAAAGGAATTGACGGGGG
CCCGCACAAGCGGTGGAGTATGTGGTTTAATTCGACGCAACGCGAAGAA
CCTTACCAGGCCTTGACATGGTATCAAAGGCCCTAGAGATAGGGAGATA
GGTATGACACAGGTGGTGCATGGTTGTCGTCAGCTCGTGTCGTGA
GATGTTGGGTTAAGTCCCGCAACGAGCGCAACCCTTGTTTCTAGTTACC
```

TABLE 6-continued

```
AACAGTAAGATGGGGACTCTAGAGAGACTGCCGGTGACAAACCGGAGGA
AGGTGGGGATGACGTCAAATCATCATGCCCCTTATGGCCTGGGCTACAC
ACGTACTACAATGGCGTCTACAAAGAGCAGCGAGCAGGTGACTGTAAGC
GAATCTCATAAAGGACGTCTCAGTTCGGATTGAAGTCTGCAACTCGACT
TCATGAAGTCGGAATCGCTAGTAATCGCGGATCACATGCCGCGGTGAA
TACGTTCTCGGGCCTTGTACACACCGCCCGTCAAACCATGGGAGTTGAT
AATACCCGAAGCCGGTGGCCTAACCGAAAGGAGGGAGCCGTCGAAGTAG
ATTG
```

TABLE 7

>2G4 (SEQ ID NO.: 6)
```
CGGCGCTGCTATAATGCAGTCGAACGAAGTTTCGAGGAAGCTTGCTTCCA
AAGAGACTTAGTGGCGAACGGGTGAGTAACACGTAGGTAACCTGCCCATG
TGTCCGGGATAACTGCTGGAAACGGTAGCTAAAACCGGATAGGTATACAG
GAGCGCATGCTCATATATTAAAGCGCCCATCAAGGCGTGAACATGGATGG
ACCTGCGGCGCATTAGCTAGTTGGTGAGGTAACGGCCCACCAAGGCGATG
ATGCGTAGCCGGCCTGAGAGGGTAAACGGCCACATTGGGACTGAGACACG
GCCCAAACTCCTACGGGAGGCAGCAGTAGGGAATTTTCGTCAATGGGGGA
AACCCTGAACGAGCAATGCCGCGTGAGTGAAGAAGGTCTTCGGATCGTAA
AGCTCTGTTGTAAGTGAAGAACGGCTCATAGAGGAAATGCTATGGGAGTG
ACGGTAGCTTACCAGAAAGCCACGGCTAACTACGTGCCAGCAGCCGCGGT
AATACGTAGGTGGCAAGCGTTATCCGGAATCATTGGGCGTAAAGGGTGCG
TAGGTGGCGTACTAAGTCTGTAGTAAAAGGCAATGGCTCAACCATTGTAA
GCTATGAAACTGGTATGCTGGAGTGCAGAAGAGGGCGATGAATTCCAT
GTGTAGCGGTAAAATGCGTAGATATATGGAGGAACACCAGTGGCGAAGGC
GGTCGCCTGGTCTGTAACTGACACTGAGGCACGAAAGCGTGGGGAGCAAA
TAGGATTAGATACCCTAGTAGTCCACGCCGTAAACGATGAGAACTAAGTG
TTGGAGGAATTCAGTGCTGCAGTTAACGCAATAAGTTCTCCGCCTGGGGA
GTATGCACGCAAGTGTGAAACTCAAAGGAATTGACGGGGCCCGCACAAG
CGGTGGAGTATGTGGTTTAATTCGAAGCAACGCGAAGAACCTTACCAGGC
CTTGACATGGATGCAAATGCCCTAGAGATAGAGAGATAATTATGGATCAC
ACAGGTGGTGCATGGTTGTCGTCAGCTCGTGTCGTGAGATGTTGGGTTAA
GTCCCGCAACGAGCGCAACCCTTGTCGCATGTTACCAGCATCAAGTTGGG
GACTCATGCGAGACTGCCGGTGACAAACCGGAGGAAGGTGGGGATGACGT
CAAATCATCATGCCCCTTATGGCCTGGGCTACACACGTACTACAATGGCG
ACCACAAAGAGCAGCGACACAGTGATGTGAAGCAATCTCATAAAGGTCG
TCTCAGTTCGGATTGAAGTCTGCAACTCGACTTCATGAAGTCGGAATCGC
TAGTAATCGCAGATCAGCATGCTGCGGTGAATACGTTCTCGGGCCTTGTA
CACACCGCCCGTCAAACCATGGGAGTCAGTAATACCCGAAGCCGGTGGCA
TAACCGTAAGGAGGAGCCGTCGAAGTGACTG
```

TABLE 8

>2H11 (SEQ ID NO.: 7)
```
AGGGCGGCTCTTAAATGCAGTCGAACGGGGTGCTCATGACGGAGGATTCG
```

TABLE 8-continued

```
TCCAACGGATTGAGTTACCTAGTGGCGGACGGGTGAGTAACGCGTGAGGA
ACCTGCCTTGGAGAGGGGAATAACACTCCGAAAGGAGTGCTAATACCGCA
TGATGCAGTTGGGTCGCATGGCTCTGACTGCCAAAGATTTATCGCTCTGA
GATGGCCTCGCGTCTGATTAGCTAGTAGGCGGGGTAACGGCCCACCTAGG
CGACGATCAGTAGCCGGACTGAGAGGTTGACCGGCCACATTGGGACTGAG
ACACGGCCCAGACTCCTACGGGAGGCAGCAGTGGGGAATATTGGGCAATG
GGCGCAAGCCTGACCCAGCAACGCCGCGTGAAGGAAGAAGGCTTTCGGGT
TGTAAACTTCTTTTGTCGGGGACGAAACAAATGACGGTACCCGACGAATA
AGCCACGGCTAACTACGTGCCAGCAGCCGCGGTAATACGTAGGTGGCAAG
CGTTATCCGGATTTACTGGGTGTAAAGGGCGTGTAGGCGGGATTGCAAGT
CAGATGTGAAAACTGGGGGCTCAACCTCCAGCCTGCATTTGAAACTGTAG
TTCTTGAGTGCTGGAGAGGCAATCGGAATTCCGTGTGTAGCGGTGAAATG
CGTAGATATACGGAGGAACACCAGTGGCGAAGGCGGATTGCTGGACAGTA
ACTGACGCTGAGGCGCGAAAGCGTGGGGAGCAAACAGGATTAGATACCCT
GGTAGTCCACGCCGTAAACGATGGATACTAGGTGTGGGGGGTCTGACCCC
CTCCGTGCCGCAGTTAACACAATAAGTATCCCACCTGGGGAGTACGATCG
CAAGGTTGAAACTCAAAGGAATTGACGGGGGCCCGCACAAGCGGTGGAGT
ATGTGGTTTAATTCGAAGCAACGCGAAGAACCTTACCAGGGCTTGACATC
CCACTAACGAGGCAGAGATGCGTTAGGTGCCCTTCGGGGAAAGTGGAGAC
AGGTGGTGCATGGTTGTCGTCAGCTCGTGTCGTGAGATGTTGGGTTAAGT
CCCGCAACGAGCGCAACCCTTATTGTTAGTTGCTACGCAAGAGCACTCTA
GCGAGACTGCCGTTGACAAAACGGAGGAAGGTGGGGACGACGTCAAATCA
TCATGCCCCTTATGTCCTGGGCCACACACGTACTACAATGGTGGTTAACA
GAGGGAGGCAATACCGCGAGGTGGAGCAAATCCCTAAAAGCCATCCCAGT
TCGGATTGCAGGCTGAAACCCGCCTGTATGAAGTTGGAATCGCTAGTAAT
CGCGGATCAGCATGCCGCGGTGAATACGTTCCCGGGCCTTGTACACACCG
CCCGTCACACCATGAGAGTCGGGAACACCCGAAGTCCGTAGCCTAACCGC
AAGGAGGGCGCGGCCGAAAGTTGTTCAT
```

TABLE 9

```
>1E11 (SEQ ID NO.: 8)
CGGGGGCTGCTACCATGCAGTCGAACGGAGTTAAGAGAGCTTGCTCTTTT
AACTTAGTGGCGGACGGGTGAGTAACGCGTGAGTAACCTGCCTTTCAGAG
GGGAATAACATTCTGAAAAGAATGCTAATACCGCATGAGATCGTAGTATC
GCATGGTACAGCGACCAAAGGAGCAATCCGCTGAAAGATGGACTCGCGTC
CGATTAGCTAGTTGGTGAGATAAAGGCCCACCAAGGCGACGATCGGTAGC
CGGACTGAGAGGTTGAACGGCCACATTGGGACTGAGACACGGCCCAGACT
CCTACGGGAGGCAGCAGTGGGGATATTGCACAATGGGGGAAACCCTGAT
GCAGCAACGCCGCGTGAAGGAAGAAGGTCTTCGGATTGTAAACTTCTGTC
CTCAGGGAAGATAATGACGGTACCTGAGGAGGAAGCTCCGGCTAACTACG
TGCCAGCAGCCGCGGTAATACGTAGGGAGCAAGCGTTGTCCGGATTTACT
GGGTGTAAAGGGTGCGTAGGCGGATCTGCAAGTCAGTAGTGAAATCCCAG
GGCTTAACCCTGGAACTGCTATTGAAACTGTGGGTCTTGAGTGAGGTAGA
GGCAGGCGGAATTCCCGGTGTAGCGGTGAAATGCGTAGAGATCGGGAGGA
ACACCAGTGGCGAAGGCGGCCTGCTGGGCCTTAACTGACGCTGAGGCACG
AAAGCATGGGTAGCAAACAGGATTAGATACCCTGGTAGTCCATGCCGTAA
ACGATGATTACTAGGTGTGGGTGGTCTGACCCCATCCGTGCCGGAGTTAA
CACAATAAGTAATCCACCTGGGGAGTACGGCCGCAAGGTTGAAACTCAAA
GGAATTGACGGGGCCCGCACAAGCAGTGGAGTATGTGGTTTAATTCGAA
GCAACGCGAAGAACCTTACCAGGTCTTGACATCCTGCTAACGAGGTAGAG
ATACGTTAGGTGCCCTTCGGGGAAAGCAGAGACAGGTGGTGCATGGTTGT
CGTCAGCTCGTGTCGTGAGATGTTGGGTTAAGTCCCGCAACGAGCGCAAC
CCCTGCTATTAGTTGCTACGCAAGAGCACTCTAATAGGACTGCCGTTGAC
AAAACGGAGGAAGGTGGGGACGACGTCAAATCATCATGCCCCTTATGACC
TGGGCTACACACGTACTACAATGGCCGTCAACAGAGAGAAGCAAAGCCGC
GAGGTGGAGCAAAACTCTAAAAACGGTCCCAGTTCGGATCGTAGGCTGCA
ACCCGCCTACGTGAAGTTGGAATTGCTAGTAATCGCGGATCATCATGCCG
CGGTGAATACGTTCCCGGGCCTTGTACACACCGCCCGTCACACCATGGGA
GCCGGTAATACCCGAAGTCAGTAGTCTAACCGCAAGGGGACGCGCCGAAA
GGTGGAGTG
```

TABLE 10

```
>2D9 (SEQ ID NO.: 9)
CTGGCGGGTGCTACCATGCAGTCGAGCGAAGCACTTTTGCGGATTTCTTC
GGATTGAAGCAATTGTGACTGAGCGGCGGACGGGTGAGTAACGCGTGGGT
AACCTGCCTCATACAGGGGGATAACAGTTGGAAACGGCTGCTAATACCGC
ATAAGCGCACAGTACCGCATGGTACCGTGTGAAAAACTCCGGTGGTATGA
GATGGACCCGCGTCTGATTAGCTAGTTGGTGGGGTAACGGCCTACCAAGG
CGACGATCAGTAGCCGACCTGAGAGGGTGACCGGCCACATTGGGACTGAG
ACACGGCCCAAACTCCTACGGGAGGCAGCAGTGGGGAATATTGCACAATG
GGGGAAACCCTGATGCAGCGACGCCGCGTGAGCGATGAAGTATTTCGGTA
TGTAAAGCTCTATCAGCAGGGAAGAAAATGACGGTACCTGACTAAGAAGC
CCCGGCTAACTACGTGCCAGCAGCCGCGGTAATACGTAGGGGGCAAGCGT
TATCCGGATTTACTGGGTGTAAAGGGAGCGTAGACGGCATGGCAAGCCAG
ATGTGAAAGCCCGGGGCTCAACCCCGGGACTGCATTTGGAACTGTCAGGC
TAGAGTGTCGGAGAGGAAAGCGGAATTCCTAGTGTAGCGGTGAAATGCGT
AGATATTAGGAGGAACACCAGTGGCGAAGGCGGCTTTCTGGACGATGACT
GACGTTGAGGCTCGAAAGCGTGGGGAGCAAACAGGATTAGATACCCTGGT
AGTCCACGCCGTAAACGATGAATACTAGGTGTCGGGTGGCAAAGCCATTC
GGTGCCGCAGCAAACGCAATAAGTATTCCACCTGGGGAGTACGTTCGCAA
```

TABLE 10-continued

```
GAATGAAACTCAAAGGAATTGACGGGGACCCGCACAAGCGGTGGAGCATG
TGGTTTAATTGGAAGCAACGCGAAGAACCTTACCTGGTCTTGACATCCCT
CTGACCGCTCTTTAATCGGAGTTTTCTTTCGGGACAGAGGAGACAGGTGG
TGCATGGTTGTCGTCAGCTCGTGTCGTGAGATGTTGGGTTAAGTCCCGCA
ACGAGCGCAACCCCTATCTTTAGTAGCCAGCATTTAGGGTGGGCACTCTA
GAGAGACTGCCAGGGATAACCTGGAGGAAGGTGGGGATGACGTCAAATCA
TCATGCCCCTTATGACCAGGGCTACACACGTGCTACAATGGCGTAAACAA
AGGGAAGCGAGCCCGCGAGGGGGAGCAAATCCCAAAAATAACGTCTCAGT
TCGGATTGTAGTCTGCAACTCGACTACATGAAGCTGGAATCGCTAGTAAT
CGCGAATCAGAATGTCGCGGTGAATACGTTCCCGGGTCTTGTACACACCG
CCCGTCACACCATGGGAGTCAGTAACGCCCGAAGTCAGTGACCCAACCGT
AAGGAGGAGCTGCCGAAGTGTACTAT
```

TABLE 11

>2F7 (SEQ ID NO.: 10)
```
GAGTGGGCCGCTACCATGCAGTCGACGAGCCGAGGGGAGCTTGCTCCCCA
GAGCTAGTGGCGGACGGGTGAGTAACACGTGAGCAACCTGCCTTTCAGAG
GGGGATAACGTTTGGAAACGAACGCTAATACCGCATAACATACCGGGACC
GCATGATTCTGGTATCAAAGGAGCAATCCGCTGAAAGATGGGCTCGCGTC
CGATTAGCTAGTTGGCGGGGTAACGGCCCACCAAGGCGACGATCGGTAGC
CGGACTGAGAGGTTGATCGGCCACATTGGGACTGAGACACGGCCCAGACT
CCTACGGGAGGCAGCAGTGGGGATATTGCACAATGGAGGAAACTCTGAT
GCAGCGACGCCGCGTGAGGGAAGACGGTCTTCGGATTGTAAACCTCTGTC
TTTGGGGACGATAATGACGGTACCCAAGGAGGAAGCTCCGGCTAACTACG
TGCCAGCAGCCGCGGTAATACGTAGGGAGCGAGCGTTGTCCGGAATTACT
GGGTGTAAAGGGAGCGTAGGCGGGTCTCAAGTCGAATGTTAAATCTACC
GGCTCAACTGGTAGCTGCGTTCGAAACTGGGGCTCTTGAGTGAAGTAGAG
GCAGGCGGAATTCCTAGTGTAGCGGTGAAATGCGTAGATATTAGGAGGAA
CACCAGTGGCGAAGGCGGCCTGCTGGGCTTTTACTGACGCTGAGGCTCGA
AAGCGTGGGGAGCAAACAGGATTAGATACCCTGGTAGTCCACGCCGTAAA
CGATGATTACTAGGTGTGGGGGACTGACCCCTTCCGTGCCGGAGTTAAC
ACAATAAGTAATCCACCTGGGGAGTACGACCGCAAGGTTGAAACTCAAAG
GAATTGACGGGGCCCGCACAAGCAGTGGATTATGTGGTTTAATTCGAAG
CAACGCGAAGAACCTTACCAGGTCTTGACATCGAGTGACGGCTCTAGAGA
TAGAGCTTTCCTTCGGGACACAAAGACAGGTGGTGCATGGTTGTCGTCAG
CTCGTGTCGTGAGATGTTGGGTTAAGTCCCGCAACGAGCGCAACCCTTAT
TATTAGTTGCTACATTCAGTTGAGCACTCTAATGAGACTGCCGTTGACAA
AACGGAGGAAGGTGGGGATGACGTCAAATCATCATGCCCCTTATGACCTG
GGCTACACACGTAATACAATGGCGATCAACAGAGGGAAGCAAGACCGCGA
GGTGGAGCAAACCCCTAAAAGTCGTCTCAGTTCGGATTGCAGGCTGCAAC
```

TABLE 11-continued

```
TCGCCTGCATGAAGTCGGAATTGCTAGTAATCGCGGATCAGCATGCCGCG
GTGAATACGTTCCCGGGCCTTGTACACACCGCCCGTCACACCATGGGAGT
CGGTAACACCCGAAGTCAGTAGCCTAACCGCAAAGAGGGCGCTGCCGAAG
ATGGATT
```

TABLE 12

>1D1 (SEQ ID NO.: 11)
```
ATGGCGGCTGCTACCTGCAGTCGAACGGGGTTATTTTGGAAATCTCTTCG
GAGATGGAATTCTTAACCTAGTGGCGGACGGGTGAGTAACGCGTGAGCAA
TCTGCCTTTAGGAGGGGATAACAGTCGGAAACGGCTGCTAATACCGCAT
AATACGTTTGGGAGGCATCTCTTGAACGTCAAAGATTTTATCGCCTTTAG
ATGAGCTCGCGTCTGATTAGCTGGTTGGCGGGGTAACGGCCCACCAAGGC
GACGATCAGTAGCCGGACTGAGAGGTTGAACGGCCACATTGGGACTGAGA
CACGGCCCAGACTCCTACGGGAGGCAGCAGTGGGGAATATTGCGCAATGG
GGGAAACCCTGACGCAGCAACGCCGCGTGATTGAAGAAGGCCTTCGGGTT
GTAAAGATCTTTAATCAGGGACGAAAATGACGGTACCTGAAGAATAAGC
TCCGGCTAACTACGTGCCAGCAGCCGCGGTAATACGTAGGGAGCAAGCGT
TATCCGGATTTACTGGGTGTAAAGGGCGCGCAGGCGGGCCGGCAAGTTGG
GAGTGAAATCCCGGGGCTTAACCCCGGAACTGCTTTCAAAACTGCTGGTC
TTGAGTGATGGAGAGGCAGGCGGAATTCCGTGTGTAGCGGTGAAATGCGT
AGATATACGGAGGAACACCAGTGGCGAAGGCGGCCTGCTGGACATTAACT
GACGCTGAGGCGCGAAAGCGTGGGGAGCAAACAGGATTAGATACCCTGGT
AGTCCACGCCGTAAACGATGGATACTAGGTGTGGGAGGTATTGACCCCTT
CCGTGCCGCAGTTAACACAATAAGTATCCCACCTGGGGAGTACGGCCGCA
AGGTTGAAACTCAAAGGAATTGACGGGGGCCCGCACAAGCAGTGGAGTAT
GTGGTTTAATTCGAAGCAACGCGAAGAACCTTACCAGGTCTTGACATCCC
GATGACCGGCGTAGAGATACGCCCTCTCTTCGGAGCATCGGTGACAGGTG
GTGCATGGTTGTCGTCAGCTCGTGTCGTGAGATGTTGGGTTAAGTCCCGC
AACGAGCGCAACCCTTACGGTTAGTTGATACGCAAGATCACTCTAGCCGG
ACTGCCGTTGACAAAACGGAGGAAGGTGGGGACGACGTCAAATCATCATG
CCCCTTATGACCTGGGCTACACACGTACTACAATGGCAGTCATACAGAGG
GAAGCAATACCGCGAGGTGGAGCAAATCCCTAAAAGCTGTCCCAGTTCAG
ATTGCAGGCTGCAACCCGCCTGCATGAAGTCGGAATTGCTAGTAATCGCG
GATCAGCATGCCGCGGTGAATACGTTCCCGGGCCTTGTACACACCGCCCG
TCACACCATGAGACCGTCAATACCCGAAGTCCGTAGCCTAACCGCAAGG
GGGCGCGCCGAAGTTACGT
```

TABLE 13

>1F8 (SEQ ID NO.: 12)
```
ATCGGGTGCTACCTGCAAGTCGAGCGAAGCGGTTTCGATGAAGTTTTCGG
ATGGAATTGAAATTGACTTAGCGGCGGACGGGTGAGTAACGCGTGGGTAA
```

TABLE 13-continued

```
CCTGCCTTACACTGGGGGATAACAGTTAGAAATGACTGCTAATACCGCAT
AAGCGCACAGGGCCGCATGGTCTGGTGCGAAAAACTCCGGTGGTGTAAGA
TGGACCCGCGTCTGATTAGGTAGTTGGTGGGGTAACGGCCCACCAAGCCG
ACGATCAGTAGCCGACCTGAGAGGGTGACCGGCCACATTGGGACTGAGAC
ACGGCCCAAACTCCTACGGGAGGCAGCAGTGGGGAATATTGGACAATGGG
CGAAAGCCTGATCCAGCGACGCCGCGTGAGTGAAGAAGTATTTCGGTATG
TAAAGCTCTATCAGCAGGGAAGAAAATGACGGTACCTGACTAAGAAGCCC
CGGCTAACTACGTGCCAGCAGCCGCGGTAATACGTAGGGGGCAAGCGTTA
TCCGGATTTACTGGGTGTAAAGGGAGCGTAGACGGTTAAGCAAGTCTGAA
GTGAAAGCCCGGGGCTCAACCCCGGTACTGCTTTGGAAACTGTTTGACTT
GAGTGCAGGAGAGGTAAGTGGAATTCCTAGTGTAGCGGTGAAATGCGTAG
ATATTAGGAGGAACACCAGTGGCGAAGGCGGCTTACTGGACTGTAACTGA
CGTTGAGGCTCGAAAGCGTGGGGAGCAAACAGGATTAGATACCCTGGTAG
TCCACGCCGTAAACGATGAATACTAGGTGTCGGGGGACAACGTCCTTCGG
TGCCGCCGCTAACGCAATAAGTATTCCACCTGGGGAGTACGTTCGCAAGA
ATGAAACTCAAAGGAATTGACGGGACCCGCACAAGCGGTGGAGCATGTG
GTTTAATTCGAAGCAACGCGAAGAACCTTACCAAGTCTTGACATCCCATT
GAAAATCCTTTAACCGTGGTCCCTCTTCGGAGCAATGAGACAGGTGGTG
CATGGTTGTCGTCAGCTCGTGTCGTGAGATGTTGGGTTAAGTCCCGCAAC
GAGCGCAACCCTTATCCTTAGTAGCCAGCACATGATGGTGGGCACTCTGG
GGAGACTGCCAGGGATAACCTGGAGGAAGGTGGGGATGACGTCAAATCAT
CATGCCCCTTATGATTTGGGCTACACACGTGCTACAATGGCGTAAACAAA
GGGAAGCAAAGGAGCGATCTGGAGCAAACCCCAAAAATAACGTCTCAGTT
CGGATTGCAGGCTGCAACTCGCCTGCATGAAGCTGGAATCGCTAGTAATC
GCGAATCAGAATGTCGCGGTGAATACGTTCCCGGGTCTTGTACACACCGC
CCGTCACACCATGGGAGTTGGTAACGCCCGAAGTCAGTGACCCAACCGTA
AGGAGGAGCGCCGAAGGCGAGGT
```

TABLE 14

>1C2 (SEQ ID NO.: 13)
```
CGGGGCTGCTTAAATGCAGTCGAACGGGATCCATCAAGCTTGCTTGGTGG
TGAGAGTGGCGAACGGGTGAGTAATGCGTGACCGACCTGCCCCATGCACC
GGAATAGCTCCTGGAAACGGGTGGTAATGCCGGATGCTCCATCACACTGC
ATGGTGTGTTGGGAAAGCCTTTGCGGCATGGGATGGGTCGCGTCCTATC
AGCTTGATGGCGGGGTAACGGCCCACCATGGCTTCGACGGGTAGCCGGCC
TGAGAGGGCGACCGGCCACATTGGGACTGAGATACGGCCCAGACTCCTAC
GGGAGGCAGCAGTGGGGAATATTGCACAATGGGCGCAAGCCTGATGCAGC
GACGCCGCGTGAGGGATGAGGCCTTCGGGTTGTAAACCTCTTTTGTTAG
GGAGCAAGGCATTTTGTGTTGAGTGTACCTTTCGAATAAGCACCGGCTAA
CTACGTGCCAGCAGCCGCGGTAATACGTAGGGTGCAAGCGTTATCCGGAA
TTATTGGGCGTAAAGGGCTCGTAGGCGGTTCGTCGCGTCCGGTGTGAAAG
TCCATCGCTTAACGGTGGATCCGCGCCGGGTACGGGCGGGCTTGAGTGCG
GTAGGGGAGACTGGAATTCCCGGTGTAACGGTGGAATGTGTAGATATCGG
GAAGAACACCAATGGCGAAGGCAGGTCTCTGGGCCGTTACTGACGCTGAG
GAGCGAAAGCGTGGGGAGCGAACAGGATTAGATACCCTGGTAGTCCACGC
CGTAAACGGTGGATGCTGGATGTGGGGCCCGTTCCACGGGTTCCGTGTCG
GAGCTAACGCGTTAAGCATCCCGCCTGGGGAGTACGGCCGCAAGGCTAAA
ACTCAAAGAAATTGACGGGGGCCCGCACAAGCGGCGGAGCATGCGGATTA
ATTCGATGCAACGCGAAGAACCTTACCTGGGCTTGACATGTTCCCGACGA
TCCCAGAGATGGGGTTTCCCTTCGGGGCGGGTTCACAGGTGGTGCATGGT
CGTCGTCAGCTCGTGTCGTGAGATGTTGGGTTAAGTCCCGCAACGAGCGC
AACCCTCGCCCCGTGTTGCCAGCGGATTGTGCCGGGAACTCACGGGGGAC
CGCCGGGGTTAACTCGGAGGAAGGTGGGGATGACGTCAGATCATCATGCC
CCTTACGTCCAGGGCTTCACGCATGCTACAATGGCCGGTACAACGGGATG
CGACAGCGCGAGCTGGAGCGGATCCCTGAAAACCGGTCTCAGTTCGGATC
GCAGTCTGCAACTCGACTGCGTGAAGGCGGAGTCGCTAGTAATCGCGAAT
CAGCAACGTCGCGGTGAATGCGTTCCCGGGCCTTGTACACACCGCCCGTC
AAGTCATGAAAGTGGGCAGCACCCGAAGCCGGTGGCCTAACCCCTTGCGG
GAGGGAGCCGTCTAAGGTAGGTT
```

TABLE 15

>1D4 (SEQ ID NO.: 14)
```
CGGGCGCTGCTTACCTGCAGTCGAGCGAAGCACTTGAGCGGATTTCTTCG
GATTGAAGTTTTTTTGACTGAGCGGCGGACGGGTGAGTAACGCGTGGGTA
ACCTGCCTCATACAGGGGGATAACAGTTAGAAATGGCTGCTAATACCGCA
TAAGCGCACAGGACCGCATGGTCTGGTGTGAAAAACTCCGGTGGTATGAG
ATGGACCCGCGTCTGATTAGCTAGTTGGAGGGGTAACGGCCCACCAAGGC
GACGATCAGTAGCCGGCCTGAGAGGGTGAACGGCCACATTGGGACTGAGA
CACGGCCCAGACTCCTACGGGAGGCAGCAGTGGGGAATATTGCACAATGG
GGGAAACCCTGATGCAGCGACGCCGCGTGAAGGAAGAAGTATCTCGGTAT
GTAAACTTCTATCAGCAGGGAAGAAAATGACGGTACCTGACTAAGAAGCC
CCGGCTAACTACGTGCCAGCAGCCGCGGTAATACGTAGGGGGCAAGCGTT
ATCCGGATTTACTGGGTGTAAAGGGAGCGTAGACGGAAGAGCAAGTCTGA
TGTGAAAGGCTGGGCTTAACCCCAGGACTGCATTGGAAACTGTTTTTCT
AGAGTGCCGGAGAGGTAAGCGGAATTCCTAGTGTAGCGGTGAAATGCGTA
GATATTAGGAGGAACACCAGTGGCGAAGGCGGCTTACTGGACGGTAACTG
ACGTTGAGGCTCGAAAGCGTGGGGAGCAAACAGGATTAGATACCCTGGTA
GTCCACGCCGTAAACGATGAATACTAGGTGTCGGGTGGCAAAGCCATTCG
GTGCCGCAGCAAACGCAATAAGTATTCCACCTGGGGAGTACGTTCGCAAG
AATGAAACTCAAAGGAATTGACGGGACCCGCACAAGCGGTGGAGCATGT
```

TABLE 15-continued

GGTTTAATTCGAAGCAACGCGAAGAACCTTACCAAGTCTTGACATCCCTC
TGACCGGCCCGTAACGGGGCCTTCCCTTCGGGGCAGAGGAGACAGGTGGT
GCATGGTTGTCGTCAGCTCGTGTCGTGAGATGTTGGGTTAAGTCCCGCAA
CGAGCGCAACCCCTATCCTTAGTAGCCAGCAGGTGAAGCTGGGCACTCTA
GGGAGACTGCCGGGGATAACCCGGAGGAAGGCGGGGACGACGTCAAATCA
TCATGCCCCTTATGATTTGGGCTACACACGTGCTACAATGGCGTAAACAA
AGGGAAGCGAGACAGCGATGTTGAGCAAATCCCAAAAATAACGTCCCAGT
TCGGACTGCAGTCTGCAACTCGACTGCACGAAGCTGGAATCGCTAGTAAT
CGCGAATCAGAATGTCGCGGTGAATACGTTCCCGGGTCTTGTACACACCG
CCCGTCACACCATGGGAGTCAGTAACGCCCGAAGTCAGTGACCCAACCTT
ATAGGAGGAGCGCCGAAGTCGACCT

TABLE 16

>1E3 (SEQ ID NO.: 15)
CGCGGGTGCTATACTGCAGTCGAACGCACTGATTTTATCAGTGAGTGGCG
AACGGGTGAGTAATACATAAGTAACCTGCCCTCATGAGGGGGATAACTAT
TAGAAATGATAGCTAAGACCGCATAGGTGAAGGGGTCGCATGACCGCTTC
ATTAAATATCCGTATGGATAGCAGGAGGATGGACTTATGGCGCATTAGCT
GGTTGGTGAGGTAACGGCTCACCAAGGCGACGATGCGTAGCCGACCTGAG
AGGGTGGACGGCCACACTGGGACTGAGACACGGCCCAGACTCCTACGGGA
GGCAGCAGTAGGGAATTTTCGGCAATGGGGGAAACCCTGACCGAGCAACG
CCGCGTGAGGGAAGAAGTATTTCGGTATGTAAACCTCTGTTATAAAGGAA
GAACGGTATGAATAGGAAATGATTCATAAGTGACGGTACTTTATGAGAAA
GCCACGGCTAACTACGTGCCAGCAGCCGCGGTAATACGTAGGTGGCGAGC
GTTATCCGGAATCATTGGGCGTAAAGAGGGAGCAGGCGGCAATAGAGGTC
TGCGGTGAAAGCCTGAAGCTAAACTTCAGTAAGCCGTGGAAACCAAATAG
CTAGAGTGCAGTAGAGGATCGTGGAATTCCATGTGTAGCGGTGAAATGCG
TAGATATATGGAGGAACACCAGTGGCGAAGGCGACGATCTGGGCTGCAAC
TGACGCTCAGTCCCGAAAGCGTGGGGAGCAAATAGGATTAGATACCCTAG
TAGTCCACGCCGTAAACGATGAGTACTAAGTGTTGGGGGTCAAACCTCAG
TGCTGCAGTTAACGCAATAAGTACTCCGCCTGAGTAGTACGTTCGCAAGA
ATGAAACTCAAAGGAATTGACGGGGCCCGCACAAGCGGTGGAGCATGTG
GTTTAATTCGAAGCAACGCGAAGAACCTTACCAGGTCTTGACATACCTCT
AAAGGCTCTAGAGATAGAGAGATAGCTATAGGGGATACAGGTGGTGCATG
GTTGTCGTCAGCTCGTGTCGTGAGATGTTGGGTTAAGTCCCGCAACGAGC
GCAACCCTTGTCGCTAGTTACCATCATTAAGTTGGGGACTCTAGCGAGAC
TGCCTCTGCAAGGAGGAGGAAGGCGGGGATGACGTCAAATCATCATGCCC
CTTATGACCTGGGCTACACACGTGCTACAATGGACGGATCAAAGGGAAGC
GAAGCCGCGAGGTGGAGCGAAACCCAAAAACCCGTTCTCAGTTCGGACTG
CAGTCTGCAACTCGACTGCACGAAGTTGGAATCGCTAGTAATCGCGAATC

TABLE 16-continued

AGAATGTCGCGGTGAATACGTTCTCGGGCCTTGTACACACCGCCCGTCAC
ACCATGAGAGTTGGTAACACCCGAAGCCGGTGGCTTAACCGCAAGGAGAG
AGCTTCTAAGGTGAAT

TABLE 17

>1A9 (SEQ ID NO.: 16)
AGGCGCGTGCTACCATGCAGTCGAACGAAGCAATTTAACGGAAGTTTTCG
GATGGAAGTTGAATTGACTGAGTGGCGGACGGGTGAGTAACGCGTGGGTA
ACCTGCCTTGTACTGGGGGACAACAGTTAGAAATGACTGCTAATACCGCA
TAAGCGCACAGTATCGCATGATACAGTGTGAAAAACTCCGGTGGTACAAG
ATGGACCCGCGTCTGATTAGCTAGTTGGTAAGGTAACGGCTTACCAAGGC
GACGATCAGTAGCCGACCTGAGAGGGTGACCGGCCACATTGGGACTGAGA
CACGGCCCAAACTCCTACGGGAGGCAGCAGTGGGGAATATTGCACAATGG
GCGAAAGCCTGATGCAGCGACGCCGCGTGAGTGAAGAAGTATTTCGGTAT
GTAAAGCTCTATCAGCAGGGAAGAAAATGACGGTACCTGACTAAGAAGCC
CCGGCTAACTACGTGCCAGCAGCCGCGGTAATACGTAGGGGGCAAGCGTT
ATCCGGATTTACTGGGTGTAAAGGGAGCGTAGACGGTAAAGCAAGTCTGA
AGTGAAAGCCCGCGGCTCAACTGCGGGACTGCTTTGGAAACTGTTTAACT
GGAGTGTCGGAGAGGTAAGTGGAATTCCTAGTGTAGCGGTGAAATGCGTA
GATATTAGGAGGAACACCAGTGGCGAAGGCGACTTACTGGACGATAACTG
ACGTTGAGGCTCGAAAGCGTGGGGAGCAAACAGGATTAGATACCCTGGTA
GTCCACGCCGTAAACGATGAATACTAGGTGTTGGGGAGCAAAGCTCTTCG
GTGCCGTCGCAAACGCAGTAAGTATTCCACCTGGGGAGTACGTTCGCAAG
AATGAAACTCAAAGGAATTGACGGGACCCGCACAAGCGGTGGAGCATGT
GGTTTAATTCGAAGCAACGCGAAGAACCTTACCAGGTCTTGACATCGATC
CGACGGGGAGTAACGTCCCCTTCCCTTCGGGCGGAGAAGACAGGTGGT
GCATGGTTGTCGTCAGCTCGTGTCGTGAGATGTTGGGTTAAGTCCCGCAA
CGAGCGCAACCCTTATTCTAAGTAGCCAGCGGTTCGGCCGGGAACTCTTG
GGAGACTGCCAGGGATAACCTGGAGGAAGGTGGGGATGACGTCAAATCAT
CATGCCCCTTATGATCTGGGCTACACACGTGCTACAATGGCGTAAACAAA
GAGAAGCAAGACCGCGAGGTGGAGCAAATCTCAAAAATAACGTCTCAGTT
CGGACTGCAGGCTGCAACTCGCCTGCACGAAGCTGGAATCGCTAGTAATC
GCGAATCAGAATGTCGCGGTGAATACGTTCCCGGGTCTTGTACACACCGC
CCGTCACACCATGGGAGTCAGTAACGCCCGAAGTCAGTGACCCAACCGCA
AGGAGGAGCGCCGAAGGCGACCGT

TABLE 18

>2G11 (SEQ ID NO.: 17)
CGGTCTCGGCTTACCATGCAGTCGAGGGGCAGCATGGTCTTAGCTTGCTA
AGGCTGATGGCGACCGGCGCACGGGTGAGTAACACGTATCCAACCTGCCG

TABLE 18-continued

TCTACTCTTGGCCAGCCTTCTGAAAGGAAGATTAATCCAGGATGGCATCA
TGAGTTCACATGTCCGCATGATTAAAGGTATTTTCCGGTAGACGATGGGG
ATGCGTTCCATTAGATAGTAGGCGGGGTAACGGCCCACCTAGTCAACGAT
GGATAGGGGTTCTGAGAGGAAGGTCCCCCACATTGGAACTGAGACACGGT
CCAAACTCCTACGGGAGGCAGCAGTGAGGAATATTGGTCAATGGGCGATG
GCCTGAACCAGCCAAGTAGCGTGAAGGATGACTGCCCTATGGGTTGTAAA
CTTCTTTTATAAAGGAATAAAGTCGGGTATGCATACCCGTTTGCATGTAC
TTTATGAATAAGGATCGGCTAACTCCGTGCCAGCAGCCGCGGTAATACGG
AGGATCCGAGCGTTATCCGGATTTATTGGGTTTAAAGGGAGCGTAGATGG
ATGTTTAAGTCAGTTGTGAAAGTTTGCGGCTCAACCGTAAAATTGCAGTT
GATACTGGATGTCTTGAGTGCAGTTGAGGCAGGCGGAATTCGTGGTGTAG
CGGTGAAATGCTTAGATATCACGAAGAACTCCGATTGCGAAGGCAGCCTG
CTAAGCTGCAACTGACATTGAGGCTCGAAAGTGTGGGTATCAAACAGGAT
TAGATACCCTGGTAGTCCACACGGTAAACGATGAATACTCGCTGTTTGCG
ATATACGGCAAGCGGCCAAGCGAAAGCGTTAAGTATTCCACCTGGGGAGT
ACGCCGGCAACGGTGAAACTCAAAGGAATTGACGGGGGCCCGCACAAGCG
GAGGAACATGTGGTTTAATTCGATGATACGCGAGGAACCTTACCCGGGCT
TAAATTGCACTCGAATGATCCGGAAACGGTTCAGCTAGCAATAGCGAGTG
TGAAGGTGCTGCATGGTTGTCGTCAGCTCGTGCCGTGAGGTGTCGGCTTA
AGTGCCATAACGAGCGCAACCCTTGTTGTCAGTTACTAACAGGTGATGCT
GAGGACTCTGACAAGACTGCCATCGTAAGATGTGAGGAAGGTGGGGATGA
CGTCAAATCAGCACGGCCCTTACGTCCGGGCTACACACGTGTTACAATG
GGGGGTACAGAGGGCCGCTACCACGCGAGTGGATGCCAATCCCTAAAACC
CCTCTCAGTTCGGACTGGAGTCTGCAACCCGACTCCACGAAGCTGGATTC
GCTAGTAATCGCGCATCAGCCACGGCGCGGTAATACGTTCCCGGGCCTT
GTACACACCGCCCGTCAAGCCATGGGAGCCGGGGGTACCTGAAGTGCGTA
ACCGCGAGGATCGCCCTAGGTAATGA

TABLE 19

>2E1 (SEQ ID NO.: 18)
CGGCGGCTGCTTACCATGCAGTCGAACGAAGCATTTAGGATTGAAGTTTT
CGGATGGATTTCCTATATGACTGAGTGGCGGACGGGTGAGTAACGCGTGG
GAACCTGCCCTATACAGGGGGATAACAGCTGGAAACGGCTGCTAATACC
GCATAAGCGCACAGAATCGCATGATTCAGTGTGAAAAGCCCTGGCAGTAT
AGGATGGTCCCGCGTCGATTAGCTGGTTGGTGAGGTAACGGCTCACCAA
GGCGACGATCAGTAGCCGGCTTGAGAGAGTGAACGGCCACATTGGGACTG
AGACACGGCCCAAACTCCTACGGGAGGCAGCAGTGGGGAATATTGCACAA
TGGGGGAAACCCTGATGCAGCGACGCCGCGTGAGTGAAGAAGTATTTCGG
TATGTAAAGCTCTATCAGCAGGGAAGAAAACAGACGGTACCTGACTAAGA
AGCCCCGGCTAACTACGTGCCAGCAGCCGCGGTAATACGTAGGGGGCAAG

TABLE 19-continued

CGTTATCCGGAATTACTGGGTGTAAAGGGTGCGTAGGTGGCATGGTAAGT
CAGAAGTGAAAGCCCGGGGCTTAACCCCGGGACTGCTTTTGAAACTGTCA
TGCTGGAGTGCAGGAGAGGTAAGCGGAATTCCTAGTGTAGCGGTGAAATG
CGTAGATATTAGGAGGAACACCAGTGGCGAAGGCGGCTTACTGGACTGTC
ACTGACACTGATGCACGAAAGCGTGGGGAGCAAACAGGATTAGATACCCT
GGTAGTCCACGCCGTAAACGATGAATACTAGGTGTCGGGGCCGTAGAGGC
TTCGGTGCCGCAGCAAACGCAGTAAGTATTCCACCTGGGGAGTACGTTCG
CAAGAATGAAACTCAAAGGAATTGACGGGACCCGCACAAGCGGTGGAGC
ATGTGGTTTAATTCGAAGCAACGCGAAGAACCTTACCTGGTCTTGACATC
CCAATGACCGAACCTTAACCGGTTTTTTCTTCGAGACATTGGAGACAGG
TGGTGCATGGTTGTCGTCAGCTCGTGTCGTGAGATGTTGGGTTAAGTCCC
GCAACGAGCGCAACCCCTATCTTTAGTAGCCAGCATTTAAGGTGGGCACT
CTAGAGAGACTGCCAGGGATAACCTGGAGGAAGGTGGGGACGACGTCAAA
TCATCATGCCCCTTATGGCCAGGGCTACACACGTGCTACAATGGCGTAAA
CAAAGGGAAGCGAAGTCGTGAGGCGAAGCAAATCCCAGAAATAACGTCTC
AGTTCGGATTGTAGTCTGCAACTCGACTACATGAAGCTGGAATCGCTAGT
AATCGTGAATCAGAATGTCACGGTGAATACGTTCCCGGGTCTTGTACACA
CCGCCCGTCACACCATGGGAGTCAGTAACGCCCGAAGTCAGTGACCCAAC
CGCAAGGAGGGAGCTGCCGAAGTACGAG

TABLE 20

>1F7 (SEQ ID NO.: 19)
TTTGTGGCGAAGCCTGATGCAGCGACGCCGCGTGAGTGAAGAAGTATTTC
GGTATGTAAAGCTCTATCAGCAGGGAAGAAAATGACGGTACCTGACTAAG
AAGCCCCGGCTAACTACGTGCCAGCAGCCGCGGTAATACGTAGGGGGCAA
GCGTTATCCGGATTTACTGGGTGTAAAGGGAGCGTAGACGGCGAAGCAAG
TCTGAAGTGAAAACCCAGGGCTCAACCCTGGGACTGCTTTGGAAACTGTT
TTGCTAGAGTGTCGGAGAGGTAAGTGGAATTCCTAGTGTAGCGGTGAAAT
GCGTAGATATTAGGAGGAACACCAGTGGCGAAGGCGGCTTACTGGACGAT
AACTGACGTTGAGGCTCGAAAGCGTGGGGAGCAAACAGGATTAGATACCC
TGGTAGTCCACGCCGTAAACGATGAATGCTAGGTGTTGGGGGGCAAAGCC
CTTCGGTGCCGTCGCAAACGCAGTAAGCATTCCACCTGGGGAGTACGTTC
GCAAGAATGAAACTCAAAGGAATTGACGGGACCCGCACAAGCGGTGGAG
CATGTGGTTTAATTCGAAGCAACGCGAAGAACCTTACCAAGTCTTGACAT
CCTCTTGACCGGCGTGTAACGGCGCCTTCCCTTCGGGGCAAGAGAGACAG
GTGGTGCATGGTTGTCGTCAGCTCGTGTCGTGAGATGTTGGGTTAAGTCC
CGCAACGAGCGCAACCCTTATCCTTAGTAGCCAGCAGGTAAAGCTGGGCA
CTCTAGGGAGACTGCCAGGGATAACCTGGAGGAAGGTGGGGATGACGTCA
AATCATCATGCCCCTTATGATTTGGGCTACACACGTGCTACAATGGCGTA
AACAAAGGGAAGCAAGACAGTGATGTGGAGCAAATCCCAAAAATAACGTC

TABLE 20-continued

CCAGTTCGGACTGTAGTCTGCAACCCGACTACACGAAGCTGGAATCGCTA
GTAATCGCGAATCAGAATGTCGCGGTGAATACGTTCCCGGGTCTTGTACA
CACCGCCCGTCACACCATGGGAGTCAGCAACGCCCGAAGTCAGTGACCCA
ACTCGCAAGAGAGGGAGCGCCGAAGTCGTCAT

TABLE 21

>1D2 (SEQ ID NO.: 20)
CTGGCGCGGCTACCATGCAGTCGAGCGAAGCATTACAGCGGAAGTTTTC
GGATGGAAGCTTTAATGACTGAGCGGCGGACGGGTGAGTAACGCGTGGA
TAACCTGCCTCATACAGGGGGATAACAGTTAGAAATGACTGCTAATACC
GCATAAGCGCACAGTATCGCATGATACGGTGTGAAAAACTCCGGTGGTA
TGAGATGGATCCGCGTCTGATTAGTTAGTTGGCGGGGTAAAGGCCCACC
AAGACGACGATCAGTAGCCGGCCTGAGAGGGTGAACGGCCACATTGGGA
CTGAGACACGGCCCAAACTCCTACGGGAGGCAGCAGTGGGGAATATTGC
ACAATGGGGGAAACCCTGATGCAGCGACGCCGCGTGAGTGAAGAAGTAT
TTCGGTATGTAAAGCTCTATCAGCAGGGAAGAAAATGACGGTACCTGAC
TAAGAAGCCCCGGCTAACTACGTGCCAGCAGCCGCGGTAATACGTAGGG
GGCAAGCGTTATCCGGATTTACTGGGTGTAAAGGGAGCGTAGACGGCAA
TGCAAGTCTGGAGTGAAAACCCAGGGCTCAACCCTGGGAGTGCTTTGGA

TABLE 21-continued

AACTGTATAGCTAGAGTGCTGGAGAGGTAAGTGGAATTCCTAGTGTAGC
GGTGAAATGCGTAGATATTAGGAGGAACACCAGTGGCGAAGGCGGCTTA
CTGGACAGTAACTGACGTTGAGGCTCGAAAGCGTGGGGAGCAAACAGGA
TTAGATACCCTGGTAGTCCACGCCGTAAACGATGAATGCTAGGTGTTGG
GGGGCAAAGCCCTTCGGTGCCGTCGCAAACGCAATAAGCATTCCACCTG
GGGAGTACGTTCGCAAGAATGAAACTCAAAGGAATTGACGGGGACCCGC
ACAAGCGGTGGAGCATGTGGTTTAATTCGAAGCAACGCGAAGAACCTTA
CCAAGTCTTGACATCCTCCTGACCGGTCCGTAACGGGGCCTTTCCTTCG
GGACAAGAGACAGGTGGTGCATGGTTGTCGTCAGCTCGTGTCGTGAG
ATGTTGGGTTAAGTCCCGCAACGAGCGCAACCCTTATCCTTAGTAGCCA
GCAGGTAGAGCTGGGCACTCTAGGGAGACTGCCAGGGATAACCTGGAGG
AAGGTGGGGATGACGTCAAATCATCATGCCCCTTATGATTTGGGCTACA
CACGTGCTACAATGGCGTAAACAAAGGGAGGCGACCCTGCGAAGGCAAG
CAAATCCCAAAAATAACGTCCCAGTTCGGACTGTAGTCTGCAACCCGAC
TACACGAAGCTGGAATCGCTAGTAATCGCGAATCAGAATGTCGCGGTGA
ATACGTTCCCGGGTCTTGTACACCGCCCGTCACACCATGGGAGTCAG
CAACGCCCGAAGTCAGTGACCCAACTGCAGGAGAGGGAGCGCCGAAGTC
GGGCT

The invention claimed is:

1. A composition that induces proliferation and/or accumulation of Th17 cells, wherein the composition comprises an active component comprising four or more bacterial strains selected from the group consisting of: *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum,* cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum,* and *Bifidobacterium breve*; and one or more enteric polymers.

2. The composition of claim 1, wherein the active component comprises, five, six, seven, eight, nine, ten, eleven, twelve, thirteen, fourteen, fifteen, sixteen, seventeen, eighteen, nineteen, or twenty bacterial strains.

3. The composition of claim 1, wherein the active component consists of bacterial strains *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum,* cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum,* and *Bifidobacterium breve*; and one or more enteric polymers.

4. The composition according to claim 1, wherein the Th17 cells are transcription factor RORgammat-positive Th17 cells or IL-17 producing Th17 cells.

5. The composition according to claim 1, wherein the composition promotes a protective immune response.

6. The composition according to claim 1, wherein the bacteria are human-derived bacteria.

7. A pharmaceutical composition comprising the composition according to claim 1 and a pharmaceutically acceptable component.

8. The pharmaceutical composition according to claim 7, wherein the pharmaceutical composition is formulated for delivery to the colon.

9. A vaccine composition comprising the composition according to claim 1 and at least one antigen, and a pharmaceutically acceptable component.

10. A composition that induces proliferation and/or accumulation of Th17 cells, wherein the composition comprises (a) four or more bacterial strains that contain DNA comprising a nucleotide sequence that has at least 97% homology with a DNA sequence designated herein as SEQ ID Nos. 1-20, or (b) four or more bacterial strains that contain DNA comprising a nucleotide sequence that has at least 97% homology with DNA of the following bacteria: *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum,* cf. *Clostridium* sp. MLG055, *Clostridium innocuum, Eubacterium desmolans,*

*Clostridium orbiscindens, Ruminococcus* sp. 16442, *Anaerotruncus colihominis, Bacteroides dorei, Bifidobacterium pseudolongum* subsp. *Pseudolongum*, or *Bifidobacterium breve*; and one or more enteric polymers.

11. The composition of claim 10, wherein the composition comprises, five, six, seven, eight, nine, ten, eleven, twelve, thirteen, fourteen, fifteen, sixteen, seventeen, eighteen, nineteen, or twenty bacterial strains.

12. The composition according to claim 10, wherein the active component consists of (a) bacterial strains that contain DNA comprising a nucleotide sequence that has at least 97% homology with a DNA sequence designated herein as SEQ ID Nos. 1-20, or (b) bacterial strains that contain DNA comprising a nucleotide sequence that has at least 97% homology with DNA of the following bacteria: *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum*, cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum*, and *Bifidobacterium breve*; and one or more enteric polymers.

13. The composition according to claim 10, wherein the Th17 cells are transcription factor RORgammat-positive Th17 cells or IL-17 producing Th17 cells.

14. The composition according to claim 10, wherein the composition promotes a protective immune response.

15. The composition according to claim 10, wherein the bacteria are human-derived bacteria.

16. A pharmaceutical composition comprising the composition according to claim 10 and a pharmaceutically acceptable component.

17. The pharmaceutical composition according to claim 16, wherein the pharmaceutical composition is formulated for delivery to the colon.

18. A vaccine composition comprising the composition according to claim 10, at least one antigen, and a pharmaceutically acceptable component.

* * * * *

SEQUENCE LISTING

<160> NUMBER OF SEQ ID NOS: 26

<210> SEQ ID NO 1
<211> LENGTH: 1419
<212> TYPE: DNA
<213> ORGANISM: Clostridium ramosum

<400> SEQUENCE: 1

```
ggggcggctg ctataatgca gtcgacgcga gcacttgtgc tcgagtggcg aacgggtgag      60
taatacataa gtaacctgcc ctagacaggg ggataactat tggaaacgat agctaagacc     120
gcatatgtac ggcacactgca tggtgaccgt attaaaagtg cctcaaagca ctggtagagg     180
atggacttat ggcgcattag ctggttggcg gggtaacggc ccaccaaggc gacgatgcgt     240
agccgacctg agagggtgac cggccacact gggactgaga cacggcccag actcctacgg     300
gaggcagcag tagggaattt tcggcaatgg gggaaaccct gaccgagcaa cgccgcgtga     360
aggaagaagg ttttcggatt gtaaacttct gttataaagg aagaacggcg gctacaggaa     420
atggtagccg agtgacggta ctttattaga agccacggc taactacgtg ccagcagccg     480
cggtaatacg taggtggcaa gcgttatccg gaattattgg gcgtaaagag ggagcaggcg     540
gcagcaaggg tctgtggtga aagcctgaag cttaacttca gtaagccata gaaaccaggc     600
agctagagtg caggagagga tcgtggaatt ccatgtgtag cggtgaaatg cgtagatata     660
tggaggaaca ccagtggcga aggcgacgat ctggcctgca actgacgctc agtcccgaaa     720
gcgtggggag caaataggat tagataccct agtagtccac gccgtaaacg atgagtacta     780
agtgttggat gtcaaagttc agtgctgcag ttaacgcaat aagtactccg cctgagtagt     840
```

```
acgttcgcaa gaatgaaact caaaggaatt gacgggggcc cgcacaagcg gtggagcatg      900
tggtttaatt cgaagcaacg cgaagaacct taccaggtct tgacatactc ataaaggctc      960
cagagatgga gagatagcta tatgagatac aggtggtgca tggttgtcgt cagctcgtgt     1020
cgtgagatgt tgggttaagt cccgcaacga gcgcaaccct tatcgttagt taccatcatt     1080
aagttgggga ctctagcgag actgccagtg acaagctgga ggaaggcggg gatgacgtca     1140
aatcatcatg cccccttatga cctgggctac acacgtgcta caatgatggt gcagaggga     1200 agcgaagccg cgaggtgaag caaaacccat aaaaccattc tcagttcgga ttgtagtctg     1260
caactcgact acatgaagtt ggaatcgcta gtaatcgcga atcagcatgt cgcggtgaat     1320
acgttctcgg gccttgtaca caccgcccgt cacaccacga gagttgataa cacccgaagc     1380
cggtggccta accgcaagga aggagcttct aagtgggat                             1419

<210> SEQ ID NO 2
<211> LENGTH: 1433
<212> TYPE: DNA
<213> ORGANISM: Bifidobacterium pseudolongum subsp. Pseudolongum

<400> SEQUENCE: 2
ctgcggcgtc taccatgcag tcgaacggga tccctggcag cttgctgccg gggtgagagt       60
ggcgaacggg tgagtaatgc gtgaccgacc tgccccatgc accggaatag ctcctggaaa      120
cgggtggtaa tgccggatgt tccacatgag cgcatgcgag tgtgggaaag gcttttttgcg     180 gcatgggatg gggtcgcgtc ctatcagctt gttggtgggg taacggccta ccaaggcgtt     240
gacgggtagc cggcctgaga gggcgaccgg ccacattggg actgagatac ggcccagact     300
cctacgggag gcagcagtgg ggaatattgc acaatgggcg caagcctgat gcagcgacgc     360
cgcgtgcggg atggaggcct cgggttgta accgctttt gttcaagggc aaggcacggt      420
ctttggccgt gttgagtgga ttgttcgaat aagcaccggc taactacgtg ccagcagccg     480
cggtaatacg tagggtgcaa gcgttatccg gatttattgg gcgtaagggg ctcgtaggcg     540
gttcgtcgcg tccggtgtga aagtccatcg cttaacggtg gatccgcgcc gggtacgggc     600
gggcttgagt gcgtaggggg agactggaat tcccggtgta acggtggaat gtgtagatat     660
cgggaagaac accaatggcg aaggcaggtc tctgggccgt tactgacgct gaggagcgaa     720
agcgtgggga gcgaacagga ttagataccc tggtagtcca cgccgtaaac ggtggatgct     780
ggatgtgggg ccttttttcc gggtcctgtg tcggagctaa cgcgttaagc atcccgcctg     840
gggagtacgg ccgcaaggct aaaactcaaa gaaattgacg ggggcccgca caagcggcgg     900
agcatgcgga ttaattcgat gcaacgcgaa gaaccttacc tgggcttgac atgtgccgga     960
cgcccgcgga gacgcgggtt cccttcgggg ccggttcaca ggtggtgcat ggtcgtcgtc    1020
agctcgtgtc gtgagatgtt gggttaagtc ccgcaacgag cgcaaccctc gccgcgtgtt    1080
gccagcgggt catgccggga actcacgtgg gaccgccggg gttaactcgg aggaaggtgg    1140
ggatgacgtc agatcatcat gccccttacg tccagggctt cacgcatgct acaatggccg    1200
gtacaacggg gtgcgacacg tgacgtgggg gcggatccct gaaaaccggt ctcagttcgg    1260
atcgcagtct gcaactcgac tgcgtgaagg tggagtcgct agtaatcgcg gatcagcaac    1320
gccgcggtga atgcgttccc gggccttgta cacaccgccc gtcaagtcat gaaagtgggc    1380
agcacccgaa gacggtggcc taacccttgt gggggagcc gtctaaggta gtg            1433

<210> SEQ ID NO 3
```

```
<211> LENGTH: 1428
<212> TYPE: DNA
<213> ORGANISM: Clostridium lactatifermentans

<400> SEQUENCE: 3
ctgccggctc taccatgcag tcgaacgaag atagttagaa tgagagcttc ggcaggattt      60
ttttctatct tagtggcgga cgggtgagta acgtgtgggc aacctgccct gtactgggga     120
ataatcattg gaaacgatga ctaataccgc atgtggtcct cggaaggcat cttctgagga     180
agaaaggatt tattcggtac aggatgggcc cgcatctgat tagctagttg gtgagataac     240
agcccaccaa ggcgacgatc agtagccgac ctgagagggt gatcggccac attgggactg     300
agacacggcc caaactccta cgggaggcag cagtgggaa tattgcacaa tgggcgaaag     360
cctgatgcag caacgccgcg tgaaggatga agggtttcgg ctcgtaaact tctatcaata     420
gggaagaaac aaatgacggt acctaaataa gaagccccgg ctaactacgt gccagcagcc     480
gcggtaatac gtaggggca agcgttatcc ggaattactg ggtgtaaagg agcgtaggc     540
ggcatggtaa gccagatgtg aaagccttgg gcttaacccg aggattgcat ttggaactat     600
caagctagag tacaggagag gaaagcggaa ttcctagtgt agcggtgaaa tgcgtagata     660
ttaggaagaa caccagtggc gaaggcggct ttctggactg aaactgacgc tgaggctcga     720
aagcgtgggg agcaaacagg attagatacc ctggtagtcc acgccgtaaa cgatgagtgc     780
taggtgtcgg ggaggaatcc tcggtgccgc agctaacgca ataagcactc cacctgggga     840
gtacgaccgc aaggttgaaa ctcaaaggaa ttgacggggg cccgcacaag cggtggagca     900
tgtggtttaa ttcgaagcaa cgcgaagaac cttaccaagg cttgacatcc cgatgaccgt     960
cctagagata ggacttctct tcggagcatc ggtgacaggt ggtgcatggt tgtcgtcagc    1020
tcgtgtcgtg agatgttggg ttaagtcccg caacgagcgc aaccctattc ttcagtagcc    1080
atcattcagt tgggcactct ggagagactg ccgtggataa cacggaggaa ggtggggatg    1140
acgtcaaatc atcatgcccc ttatgtcttg ggctacacac gtgctacaat ggctggtaac    1200
aaagtgacgc gagacggcga cgttaagcaa atcacaaaaa cccagtccca gttcggattg    1260
tagtctgcaa ctcgactaca tgaagctgga atcgctagta atcgcgaatc agcatgtcgc    1320
ggtgaatacg ttcccgggcc ttgtacacac cgcccgtcac accatgggag ttggaagcac    1380
ccgaagtcgg tgacctaacc gtaaggaaga gccgccgaag tagggat                  1428

<210> SEQ ID NO 4
<211> LENGTH: 1422
<212> TYPE: DNA
<213> ORGANISM: Blautia sp. canine oral taxon 143

<400> SEQUENCE: 4
cggcgctcta ccatgcagtc gacgaagcga tttgaatgaa gttttcggat ggattttaaa      60
ttgactgagt ggcggacggg tgagtaacgc gtgggtaacc tgccccatac agggggataa     120
cagttagaaa tgactgctaa taccgcataa gaccacagcg ccgcatggtg caggggtaaa     180
aactccggtg gtatgggatg gacccgcgtc tgattagctt gttggcgggg taacggccca     240
ccaaggcgac gatcagtagc cgacctgaga gggtgaccgg ccacattggg actgagacac     300
ggcccaaact cctacgggag gcagcagtgg ggaatattgc acaatggggg aaaccctgat     360
gcagcgacgc cgcgtgagtg atgaagtatt tcggtatgta agctctatc agcagggaag     420
aaaatgacgg tacctgacta agaagccccg gctaactacg tgccagcagc cgcggtaata     480
cgtaggggc aagcgttatc cggatttact gggtgtaaag ggagcgtaga cggctgtgca     540
```

```
agtctggagt gaaagcccgg ggctcaaccc cgggactgct ttggaaactg tacggctgga      600
gtgctggaga ggcaagcgga attcctagtg tagcggtgaa atgcgtagat attaggagga      660
acaccagtgg cgaaggcggc ttgctggaca gtaactgacg ttgaggctcg aaagcgtggg      720
gagcaaacag gattagatac cctggtagtc cacgccgtaa acgatgaatg ctaggtgtcg      780
gggagcaaag ctcttcggtg ccgccgcaaa cgcaataagc attccacctg gggagtacgt      840
tcgcaagaat gaaactcaaa ggaattgacg ggacccgca caagcggtgg agcatgtggt      900
ttaattcgaa gcaacgcgaa gaaccttacc aagtcttgac atcccctga ccggcaagta      960 atgtcgcctt tccttcggga caggggagac aggtggtgca tggttgtcgt cagctcgtgt     1020
cgtgagatgt tgggttaagt cccgcaacga gcgcaaccct tatcctcagt agccagcagg     1080
tgaagctggg cactctgtgg agactgccag ggataacctg gaggaaggtg gggacgacgt     1140
caaatcatca tgcccttat gacttgggct acacacgtgc tacaatggcg taaacaaagg     1200
gaagcgagag ggtgacctgg agcaaatccc aaaaataacg tctcagttcg gattgtagtc     1260
tgcaactcga ctacatgaag ctggaatcgc tagtaatcgc gaatcagcat gtcgcggtga     1320
atacgttccc gggtcttgta cacaccgccc gtcacaccat gggagtcagc aacgcccgaa     1380
gccggtgacc taaccgcaag gaaggagccg tcgaagtcgt cg                        1422

<210> SEQ ID NO 5
<211> LENGTH: 1425
<212> TYPE: DNA
<213> ORGANISM: cf. Clostridium sp. MLG055

<400> SEQUENCE: 5
cggcgctgct atactgcagt cgaacgaagc gaaggtagct tgctatcgga gcttagtggc       60
gaacgggtga gtaacacgta gataacctgc ctgtatgacc gggataacag ttggaaacga      120
ctgctaatac cggataggca gagaggaggc atctcttctc tgttaaagtt gggatacaac      180
gcaaacagat ggatctgcgg tgcattagct agttggtgag gtaacggccc accaaggcga      240
tgatgcatag ccggcctgag agggcgaacg gccacattgg gactgagaca cggcccaaac      300
tcctacggga ggcagcagta gggaattttc ggcaatgggg gaaaccctga ccgagcaatg      360
ccgcgtgagt gaagacggcc ttcgggttgt aaagctctgt tgtaagggaa gaacggcata      420
gagagggaat gctctatgag tgacggtacc ttaccagaaa gccacggcta actacgtgcc      480
agcagccgcg gtaatacgta ggtggcaagc gttatccgga attattgggc gtaagggtg      540 cgtaggcggc tggataagtc tgaggtaaaa gcccgtggct caaccacggt aagcttggaa      600
aactgtctgg ctggagtgca ggagaggaca atggaattcc atgtgtagcg gtaaaatgcg      660
tagatatatg gaggaacacc agtggcgaag gcggttgtct ggcctgtaac tgacgctgaa      720
gcacgaaagc gtgggagca ataggatta gataccctag tagtccacgc cgtaaacgat      780
gagaactaag tgttgggaa actcagtgct gcagttaacg caataagttc tccgcctggg      840
gagtatgcac gcaagtgtga aactcaaagg aattgacggg ggcccgcaca gcggtggag      900 tatgtggttt aattcgacgc aacgcgaaga accttaccag gccttgacat ggtatcaaag      960
gccctagaga tagggagata ggtatgatac acacaggtgg tgcatggttg tcgtcagctc     1020
gtgtcgtgag atgttgggtt aagtcccgca acgagcgcaa cccttgtttc tagttaccaa     1080
cagtaagatg gggactctag agagactgcc ggtgacaaac cggaggaagg tgggatgac      1140 gtcaaatcat catgccccttt atggcctggg ctacacacgt actacaatgg cgtctacaaa     1200
```

| | |
|---|---|
| gagcagcgag caggtgactg taagcgaatc tcataaagga cgtctcagtt cggattgaag | 1260 |
| tctgcaactc gacttcatga agtcggaatc gctagtaatc gcggatcagc atgccgcggt | 1320 |
| gaatacgttc tcgggccttg tacacaccgc ccgtcaaacc atgggagttg ataatacccg | 1380 |
| aagccggtgg cctaaccgaa aggagggagc cgtcgaagta gattg | 1425 |

<210> SEQ ID NO 6
<211> LENGTH: 1431
<212> TYPE: DNA
<213> ORGANISM: Clostridium innocuum

<400> SEQUENCE: 6

| | |
|---|---|
| cggcgctgct ataatgcagt cgaacgaagt ttcgaggaag cttgcttcca aagagactta | 60 |
| gtggcgaacg ggtgagtaac acgtaggtaa cctgcccatg tgtccggat aactgctgga | 120 |
| aacggtagct aaaaccggat aggtatacag agcgcatgct cagtatatta aagcgcccat | 180 |
| caaggcgtga acatggatgg acctgcggcg cattagctag ttggtgaggt aacggcccac | 240 |
| caaggcgatg atgcgtagcc ggcctgagag ggtaaacggc cacattggga ctgagacacg | 300 |
| gcccaaactc ctacgggagg cagcagtagg gaattttcgt caatggggga aaccctgaac | 360 |
| gagcaatgcc gcgtgagtga agaaggtctt cggatcgtaa agctctgttg taagtgaaga | 420 |
| acggctcata aggaaatgc tatgggagtg acggtagctt accagaaagc cacggctaac | 480 |
| tacgtgccag cagccgcggt aatacgtagg tggcaagcgt tatccggaat cattgggcgt | 540 |
| aaagggtgcg taggtggcgt actaagtctg tagtaaaagg caatggctca accattgtaa | 600 |
| gctatggaaa ctggtatgct ggagtgcaga agagggcgat ggaattccat gtgtagcggt | 660 |
| aaaatgcgta gatatatgga ggaacaccag tggcgaaggc ggtcgcctgg tctgtaactg | 720 |
| acactgaggc acgaaagcgt ggggagcaaa taggattaga taccctagta gtccacgccg | 780 |
| taaacgatga gaactaagtg ttggaggaat tcagtgctgc agttaacgca ataagttctc | 840 |
| cgcctgggga gtatgcacgc aagtgtgaaa ctcaaaggaa ttgacggggg cccgcacaag | 900 |
| cggtggagta tgtggtttaa ttcgaagcaa cgcgaagaac cttaccaggc cttgacatgg | 960 |
| atgcaaatgc cctagagata gagagataat tatggatcac acaggtggtg catggttgtc | 1020 |
| gtcagctcgt gtcgtgagat gttgggttaa gtcccgcaac gagcgcaacc cttgtcgcat | 1080 |
| gttaccagca tcaagttggg gactcatgcg agactgccgg tgacaaaccg gaggaaggtg | 1140 |
| gggatgacgt caaatcatca tgccccttat ggcctgggct acacacgtac tacaatggcg | 1200 |
| accacaaaga gcagcgacac agtgatgtga agcgaatctc ataaaggtcg tctcagttcg | 1260 |
| gattgaagtc tgcaactcga cttcatgaag tcggaatcgc tagtaatcgc agatcagcat | 1320 |
| gctgcggtga atacgttctc gggccttgta cacaccgccc gtcaaaccat gggagtcagt | 1380 |
| aatacccgaa gccggtggca taaccgtaag gaggagccgt cgaagtgact g | 1431 |

<210> SEQ ID NO 7
<211> LENGTH: 1428
<212> TYPE: DNA
<213> ORGANISM: Clostridium orbiscindens

<400> SEQUENCE: 7

| | |
|---|---|
| agggcggctc ttaaatgcag tcgaacgggg tgctcatgac ggaggattcg tccaacggat | 60 |
| tgagttacct agtggcggac gggtgagtaa cgcgtgagga acctgccttg gagagggaa | 120 |
| taacactccg aaaggagtgc taataccgca tgatgcagtt gggtcgcatg gctctgactg | 180 |
| ccaaagattt atcgctctga gatggcctcg cgtctgatta gctagtaggc ggggtaacgg | 240 |

```
cccacctagg cgacgatcag tagccggact gagaggttga ccggccacat tgggactgag      300
acacggccca gactcctacg ggaggcagca gtggggaata ttgggcaatg ggcgcaagcc      360
tgacccagca acgccgcgtg aaggaagaag ctttcgggt tgtaaacttc ttttgtcggg      420
gacgaaacaa atgacggtac ccgacgaata agccacggct aactacgtgc cagcagccgc      480
ggtaatacgt aggtggcaag cgttatccgg atttactggg tgtaaagggc gtgtaggcgg      540
gattgcaagt cagatgtgaa aactgggggc tcaacctcca gcctgcattt gaaactgtag      600
ttcttgagtg ctggagaggc aatcggaatt ccgtgtgtag cggtgaaatg cgtagatata      660
cggaggaaca ccagtggcga aggcggattg ctggacagta actgacgctg aggcgcgaaa      720
gcgtggggag caaacaggat tagataccct ggtagtccac gccgtaaacg atggatacta      780
ggtgtggggg gtctgacccc ctccgtgccg cagttaacac aataagtatc ccacctgggg      840
agtacgatcg caaggttgaa actcaaagga attgacgggg cccgcacaa gcggtggagt      900 atgtggttta attcgaagca acgcgaagaa ccttaccagg gcttgacatc ccactaacga      960
ggcagagatg cgttaggtgc ccttcgggga aagtggagac aggtggtgca tggttgtcgt     1020
cagctcgtgt cgtgagatgt tgggttaagt cccgcaacga gcgcaaccct tattgttagt     1080
tgctacgcaa gagcactcta gcgagactgc cgttgacaaa acggaggaag gtgggacga     1140 cgtcaaatca tcatgcccct tatgtcctgg gccacacacg tactacaatg gtggttaaca     1200
gagggaggca ataccgcgag gtggagcaaa tccctaaaag ccatcccagt tcggattgca     1260
ggctgaaacc cgcctgtatg aagttggaat cgctagtaat cgcggatcag catgccgcgg     1320
tgaatacgtt cccgggcctt gtacacaccg cccgtcacac catgagagtc gggaacaccc     1380
gaagtccgta gcctaaccgc aaggagggcg cggccgaaag ttgttcat                 1428
```

<210> SEQ ID NO 8
<211> LENGTH: 1409
<212> TYPE: DNA
<213> ORGANISM: Ruminococcus sp. 16442

<400> SEQUENCE: 8

```
cgggggctgc taccatgcag tcgaacggag ttaagagagc ttgctctttt aacttagtgg       60
cggacgggtg agtaacgcgt gagtaacctg cctttcagag gggaataaca ttctgaaaag      120
aatgctaata ccgcatgaga tcgtagtatc gcatggtaca cgaccaaag gagcaatccg      180 ctgaaagatg gactcgcgtc cgattagcta gttggtgaga taaaggccca ccaaggcgac      240
gatcggtagc cggactgaga ggttgaacgg ccacattggg actgagacac ggcccagact      300
cctacgggag gcagcagtgg gggatattgc acaatggggg aaaccctgat gcagcaacgc      360
cgcgtgaagg aagaaggtct tcggattgta aacttctgtc ctcagggaag ataatgacgg      420
tacctgagga ggaagctccg gctaactacg tgccagcagc cgcggtaata cgtagggagc      480
aagcgttgtc cggatttact gggtgtaaag ggtgcgtagg cggatctgca agtcagtagt      540
gaaatcccag ggcttaaccc tggaactgct attgaaactg tgggtcttga gtgaggtaga      600
ggcaggcgga attcccggtg tagcggtgaa atgcgtagag atcgggagga acaccagtgg      660
cgaaggcggc ctgctgggcc ttaactgacg ctgaggcacg aaagcatggg tagcaaacag      720
gattagatac cctggtagtc catgccgtaa acgatgatta ctaggtgtgg gtggtctgac      780
cccatccgtg ccggagttaa cacaataagt aatccacctg gggagtacgg ccgcaaggtt      840
gaaactcaaa ggaattgacg ggggcccgca caagcagtgg agtatgtggt ttaattcgaa      900
```

| | |
|---|---|
| gcaacgcgaa gaaccttacc aggtcttgac atcctgctaa cgaggtagag atacgttagg | 960 |
| tgcccttcgg ggaaagcaga gacaggtggt gcatggttgt cgtcagctcg tgtcgtgaga | 1020 |
| tgttgggtta agtcccgcaa cgagcgcaac ccctgctatt agttgctacg caagagcact | 1080 |
| ctaataggac tgccgttgac aaaacggagg aaggtgggga cgacgtcaaa tcatcatgcc | 1140 |
| ccttatgacc tgggctacac acgtactaca atggccgtca acagagagaa gcaaagccgc | 1200 |
| gaggtggagc aaaactctaa aaacggtccc agttcggatc gtaggctgca acccgcctac | 1260 |
| gtgaagttgg aattgctagt aatcgcggat catcatgccg cggtgaatac gttcccgggc | 1320 |
| cttgtacaca ccgcccgtca caccatggga gccggtaata cccgaagtca gtagtctaac | 1380 |
| cgcaagggga cgcgccgaaa ggtggagtg | 1409 |

<210> SEQ ID NO 9
<211> LENGTH: 1426
<212> TYPE: DNA
<213> ORGANISM: Ruminococcus gnavus

<400> SEQUENCE: 9

| | |
|---|---|
| ctggcgggtg ctaccatgca gtcgagcgaa gcacttttgc ggatttcttc ggattgaagc | 60 |
| aattgtgact gagcggcgga cgggtgagta acgcgtgggg aacctgcctc atacaggggg | 120 |
| ataacagttg gaaacggctg ctaataccgc ataagcgcac agtaccgcat ggtaccgtgt | 180 |
| gaaaaactcc ggtggtatga gatggacccg cgtctgatta gctagttggt ggggtaacgg | 240 |
| cctaccaagg cgacgatcag tagccgacct gagagggtga ccggccacat tgggactgag | 300 |
| acacggccca aactcctacg ggaggcagca gtggggaata ttgcacaatg ggggaaaccc | 360 |
| tgatgcagcg acgccgcgtg agcgatgaag tatttcggta tgtaaagctc tatcagcagg | 420 |
| gaagaaaatg acggtacctg actaagaagc cccggctaac tacgtgccag cagccgcggt | 480 |
| aatacgtagg gggcaagcgt tatccggatt tactgggtgt aaagggagcg tagacggcat | 540 |
| ggcaagccag atgtgaaagc ccggggctca accccgggac tgcatttgga actgtcaggc | 600 |
| tagagtgtcg gagaggaaag cggaattcct agtgtagcgg tgaaatgcgt agatattagg | 660 |
| aggaacacca gtggcgaagg cggctttctg gacgatgact gacgttgagg ctcgaaagcg | 720 |
| tggggagcaa acaggattag ataccctggt agtccacgcc gtaaacgatg aatactaggt | 780 |
| gtcgggtggc aaagccattc ggtgccgcag caaacgcaat aagtattcca cctggggagt | 840 |
| acgttcgcaa gaatgaaact caaaggaatt gacggggacc cgcacaagcg gtggagcatg | 900 |
| tggtttaatt cgaagcaacg cgaagaacct tacctggtct tgacatccct ctgaccgctc | 960 |
| tttaatcgga gttttctttc gggacagagg agacaggtgg tgcatggttg tcgtcagctc | 1020 |
| gtgtcgtgag atgttgggtt aagtcccgca acgagcgcaa ccctatctt agtagccag | 1080 |
| catttagggt gggcactcta gagagactgc caggataac ctggaggaag gtggggatga | 1140 |
| cgtcaaatca tcatgcccct tatgaccagg gctacacacg tgctacaatg gcgtaaacaa | 1200 |
| agggaagcga gcccgcgagg gggagcaaat cccaaaaata acgtctcagt tcggattgta | 1260 |
| gtctgcaact cgactacatg aagctggaat cgctagtaat cgcgaatcag aatgtcgcgg | 1320 |
| tgaatacgtt cccgggtctt gtacacaccg cccgtcacac catgggagtc agtaacgccc | 1380 |
| gaagtcagtg acccaaccgt aaggaggagc tgccgaagtg tactat | 1426 |

<210> SEQ ID NO 10
<211> LENGTH: 1407
<212> TYPE: DNA
<213> ORGANISM: Anaerotruncus colihominis

<400> SEQUENCE: 10

```
gagtgggccg ctaccatgca gtcgacgagc cgaggggagc ttgctcccca gagctagtgg        60
cggacgggtg agtaacacgt gagcaacctg cctttcagag ggggataacg tttggaaacg       120
aacgctaata ccgcataaca taccgggacc gcatgattct ggtatcaaag gagcaatccg       180
ctgaaagatg ggctcgcgtc cgattagcta gttggcgggg taacggccca ccaaggcgac       240
gatcggtagc cggactgaga ggttgatcgg ccacattggg actgagacac ggcccagact       300
cctacgggag gcagcagtgg gggatattgc acaatggagg aaactctgat gcagcgacgc       360
cgcgtgaggg aagacggtct tcggattgta aacctctgtc tttggggacg ataatgacgg       420
tacccaagga ggaagctccg gctaactacg tgccagcagc cgcggtaata cgtagggagc       480
gagcgttgtc cggaattact gggtgtaaag ggagcgtagg cggggtctca agtcgaatgt       540
taaatctacc ggctcaactg gtagctgcgt tcgaaactgg ggctcttgag tgaagtagag       600
gcaggcggaa ttcctagtgt agcggtgaaa tgcgtagata ttaggaggaa caccagtggc       660
gaaggcggcc tgctgggctt ttactgacgc tgaggctcga aagcgtgggg agcaaacagg       720
attagatacc ctggtagtcc acgccgtaaa cgatgattac taggtgtggg gggactgacc       780
ccttccgtgc cggagttaac acaataagta atccacctgg ggagtacgac cgcaaggttg       840
aaactcaaag gaattgacgg gggcccgcac aagcagtgga ttatgtggtt taattcgaag       900
caacgcgaag aaccttacca ggtcttgaca tcgagtgacg gctctagaga tagagctttc       960
cttcgggaca caaagacagg tggtgcatgg ttgtcgtcag ctcgtgtcgt gagatgttgg      1020
gttaagtccc gcaacgagcg caacccttat tattagttgc tacattcagt tgagcactct      1080
aatgagactg ccgttgacaa aacggaggaa ggtggggatg acgtcaaatc atcatgcccc      1140
ttatgacctg ggctacacac gtaatacaat ggcgatcaac agagggaagc aagaccgcga      1200
ggtggagcaa accctaaaaa gtcgtctcag ttcggattgc aggctgcaac tcgcctgcat      1260
gaagtcggaa ttgctagtaa tcgcggatca gcatgccgcg gtgaatacgt tcccgggcct      1320
tgtacacacc gcccgtcaca ccatgggagt cggtaacacc cgaagtcagt agcctaaccg      1380
caaagagggc gctgccgaag atggatt                                          1407
```

<210> SEQ ID NO 11
<211> LENGTH: 1419
<212> TYPE: DNA
<213> ORGANISM: Eubacterium desmolans

<400> SEQUENCE: 11

```
atggcggctg ctacctgcag tcgaacgggg ttattttgga atctcttcg gagatggaat        60
tcttaaccta gtggcggacg ggtgagtaac gcgtgagcaa tctgccttta ggaggggat       120
aacagtcgga aacggctgct aataccgcat aatacgtttg ggaggcatct cttgaacgtc       180
aaagatttta tcgcctttag atgagctcgc gtctgattag ctggttggcg gggtaacggc       240
ccaccaaggc gacgatcagt agccggactg agaggttgaa cggccacatt gggactgaga       300
cacggcccag actcctacgg gaggcagcag tggggaatat tgcgcaatgg ggaaaccct       360
gacgcagcaa cgccgcgtga ttgaagaagg ccttcgggtt gtaaagatct ttaatcaggg       420
acgaaaaatg acggtacctg aagaataagc tccggctaac tacgtgccag cagccgcggt       480
aatacgtagg gagcaagcgt tatccggatt tactgggtgt aaagggcgcg caggcgggcc       540
ggcaagttgg gagtgaaatc ccggggctta acccccggaac tgctttcaaa actgctggtc       600
```

```
ttgagtgatg gagaggcagg cggaattccg tgtgtagcgg tgaaatgcgt agatatacgg      660
aggaacacca gtggcgaagg cggcctgctg gacattaact gacgctgagg cgcgaaagcg      720
tggggagcaa acaggattag ataccctggt agtccacgcc gtaaacgatg gatactaggt      780
gtgggaggta ttgaccccct ccgtgccgca gttaacacaa taagtatccc acctggggag      840
tacggccgca aggttgaaac tcaaaggaat tgacggggc ccgcacaagc agtggagtat       900
gtggtttaat tcgaagcaac gcgaagaacc ttaccaggtc ttgacatccc gatgaccggc      960
gtagagatac gccctctctt cggagcatcg gtgacaggtg gtgcatggtt gtcgtcagct     1020
cgtgtcgtga gatgttgggt taagtcccgc aacgagcgca acccttacgg ttagttgata     1080
cgcaagatca ctctagccgg actgccgttg acaaaacgga ggaaggtggg gacgacgtca     1140
aatcatcatg ccccttatga cctgggctac acacgtacta caatggcagt catacagagg     1200
gaagcaatac cgcgaggtgg agcaaatccc taaaagctgt cccagttcag attgcaggct     1260
gcaacccgcc tgcatgaagt cggaattgct agtaatcgcg gatcagcatg ccgcggtgaa     1320
tacgttcccg ggccttgtac acaccgcccg tcacaccatg agagccgtca atacccgaag     1380
tccgtagcct aaccgcaagg gggcgcgccg aagttacgt                            1419
```

<210> SEQ ID NO 12
<211> LENGTH: 1423
<212> TYPE: DNA
<213> ORGANISM: Clostridium hathewayi

<400> SEQUENCE: 12

```
atcgggtgct acctgcaagt cgagcgaagc ggtttcgatg aagttttcgg atggaattga       60
aattgactta gcggcggacg ggtgagtaac gcgtgggtaa cctgccttac actgggggat      120
aacagttaga aatgactgct aataccgcat aagcgcacag ggccgcatgg tctggtgcga      180
aaaactccgg tggtgtaaga tggacccgcg tctgattagg tagttggtgg ggtaacggcc      240
caccaagccg acgatcagta gccgacctga gagggtgacc ggccacattg gactgagaca      300
acggcccaaa ctcctacggg aggcagcagt ggggaatatt ggacaatggg cgaaagcctg      360
atccagcgac gccgcgtgag tgaagaagta tttcggtatg taaagctcta tcagcaggga      420
agaaaatgac ggtacctgac taagaagccc cggctaacta cgtgccagca gccgcggtaa      480
tacgtagggg gcaagcgtta tccggattta ctgggtgtaa agggagcgta gacggttaag      540
caagtctgaa gtgaaagccc ggggctcaac cccggtactg ctttggaaac tgtttgactt      600
gagtgcagga gaggtaagtg gaattcctag tgtagcggtg aaatgcgtag atattaggag      660
gaacaccagt ggcgaaggcg gcttactgga ctgtaactga cgttgaggct cgaaagcgtg      720
gggagcaaac aggattagat accctggtag tccacgccgt aaacgatgaa tactaggtgt      780
cggggacaa cgtccttcgg tgccgccgct aacgcaataa gtattccacc tggggagtac      840
gttcgcaaga atgaaactca aaggaattga cggggacccg cacaagcggt ggagcatgtg      900
gtttaattcg aagcaacgcg aagaacctta ccaagtcttg acatcccatt gaaaatcctt      960
taaccgtggt ccctcttcgg agcaatggag acaggtggtg catggttgtc gtcagctcgt     1020
gtcgtgagat gttgggttaa gtcccgcaac gagcgcaacc cttatcctta gtagccagca     1080
catgatggtg ggcactctgg ggagactgcc agggataacc tggaggaagg tggggatgac     1140
gtcaaatcat catgccccct tatgatttggg ctacacacgt gctacaatgg cgtaaacaaa    1200
gggaagcaaa ggagcgatct ggagcaaacc ccaaaaataa cgtctcagtt cggattgcag     1260
gctgcaactc gcctgcatga agctggaatc gctagtaatc gcgaatcaga atgtcgcggt     1320
```

```
gaatacgttc ccgggtcttg tacacaccgc ccgtcacacc atgggagttg gtaacgcccg    1380
aagtcagtga cccaaccgta aggaggagcg ccgaaggcga ggt                      1423

<210> SEQ ID NO 13
<211> LENGTH: 1423
<212> TYPE: DNA
<213> ORGANISM: Bifidobacterium breve

<400> SEQUENCE: 13
cggggctgct taaatgcagt cgaacgggat ccatcaagct tgcttggtgg tgagagtggc      60
gaacgggtga gtaatgcgtg accgacctgc cccatgcacc ggaatagctc ctggaaacgg    120
gtggtaatgc cggatgctcc atcacactgc atggtgtgtt gggaaagcct ttgcggcatg    180
ggatggggtc gcgtcctatc agcttgatgg cggggtaacg gcccaccatg gcttcgacgg    240
gtagccggcc tgagagggcg accggccaca ttgggactga gatacggccc agactcctac    300
gggaggcagc agtggggaat attgcacaat gggcgcaagc ctgatgcagc gacgccgcgt    360
gagggatgga ggccttcggg ttgtaaacct ctttttgttag ggagcaaggc attttgtgtt    420
gagtgtacct ttcgaataag caccggctaa ctacgtgcca gcagccgcgg taatacgtag    480
ggtgcaagcg ttatccggaa ttattgggcg taaagggctc gtaggcggtt cgtcgcgtcc    540
ggtgtgaaag tccatcgctt aacggtggat ccgcgccggg tacgggcggg cttgagtgcg    600
gtaggggaga ctggaattcc cggtgtaacg gtggaatgtg tagatatcgg aagaacacc    660 aatggcgaag gcaggtctct gggccgttac tgacgctgag gagcgaaagc gtggggagcg    720
aacaggatta gataccctgg tagtccacgc cgtaaacggt ggatgctgga tgtggggccc    780
gttccacggg ttccgtgtcg gagctaacgc gttaagcatc ccgcctgggg agtacggccg    840
caaggctaaa actcaaagaa attgacgggg gcccgcacaa gcggcggagc atgcggatta    900
attcgatgca acgcgaagaa ccttacctgg gcttgacatg ttcccgacga tcccagagat    960
ggggtttccc ttcgggcgg gttcacaggt ggtgcatggt cgtcgtcagc tcgtgtcgtg   1020
agatgttggg ttaagtcccg caacgagcgc aaccctcgcc ccgtgttgcc agcggattgt   1080
gccgggaact cacgggggac cgccggggtt aactcggagg aaggtgggga tgacgtcaga   1140
tcatcatgcc ccttacgtcc agggcttcac gcatgctaca atggccggta caacgggatg   1200
cgacagcgcg agctggagcg atccctgaa accggtctc agttcggatc gcagtctgca   1260
actcgactgc gtgaaggcgg agtcgctagt aatcgcgaat cagcaacgtc gcggtgaatg   1320
cgttcccggg ccttgtacac accgcccgtc aagtcatgaa agtgggcagc acccgaagcc   1380
ggtggcctaa ccccttgcgg gagggagccg tctaaggtag gtt                   1423

<210> SEQ ID NO 14
<211> LENGTH: 1425
<212> TYPE: DNA
<213> ORGANISM: Ruminococcus sp. M-1

<400> SEQUENCE: 14
cgggcgctgc ttacctgcag tcgagcgaag cacttgagcg gatttcttcg gattgaagtt      60
tttttgactg agcggcggac gggtgagtaa cgcgtgggta acctgcctca tacaggggga    120
taacagttag aaatggctgc taataccgca taagcgcaca ggaccgcatg gtctggtgtg    180
aaaaactccg gtggtatgag atggacccgc gtctgattag ctagttggag ggtaacggc    240 ccaccaaggc gacgatcagt agccggcctg agagggtgaa cggccacatt gggactgaga    300
```

```
cacggcccag actcctacgg gaggcagcag tggggaatat tgcacaatgg gggaaaccct    360
gatgcagcga cgccgcgtga aggaagaagt atctcggtat gtaaacttct atcagcaggg    420
aagaaaatga cggtacctga ctaagaagcc ccggctaact acgtgccagc agccgcggta    480
atacgtaggg ggcaagcgtt atccggattt actgggtgta aagggagcgt agacggaaga    540
gcaagtctga tgtgaaaggc tggggcttaa ccccaggact gcattggaaa ctgttttttct   600 agagtgccgg agaggtaagc ggaattccta gtgtagcgt gaaatgcgta gatattagga     660
ggaacaccag tggcgaaggc ggcttactgg acggtaactg acgttgaggc tcgaaagcgt    720
ggggagcaaa caggattaga taccctggta gtccacgccg taaacgatga atactaggtg    780
tcgggtggca aagccattcg gtgccgcagc aaacgcaata agtattccac ctggggagta    840
cgttcgcaag aatgaaactc aaaggaattg acggggaccc gcacaagcgg tggagcatgt    900
ggtttaattc gaagcaacgc gaagaacctt accaagtctt gacatccctc tgaccggccc    960 gtaacgggc cttcccttcg ggcagagga gacaggtggt gcatggttgt cgtcagctcg     1020
tgtcgtgaga tgttgggtta agtcccgcaa cgagcgcaac ccctatcctt agtagccagc    1080
aggtgaagct gggcactcta gggagactgc cggggataac ccggaggaag gcgggacga    1140 cgtcaaatca tcatgcccct tatgatttgg gctacacacg tgctacaatg gcgtaaacaa    1200
agggaagcga cacagcgatg ttgagcaaat cccaaaaata acgtcccagt tcggactgca    1260
gtctgcaact cgactgcacg aagctggaat cgctagtaat cgcgaatcag aatgtcgcgg    1320
tgaatacgtt cccgggtctt gtacacaccg cccgtcacac catgggagtc agtaacgccc    1380
gaagtcagtg acccaacctt ataggaggag cgccgaagtc gacct                   1425

<210> SEQ ID NO 15
<211> LENGTH: 1416
<212> TYPE: DNA
<213> ORGANISM: Coprobacillus cateniformis

<400> SEQUENCE: 15
cgcgggtgct atactgcagt cgaacgcact gattttatca gtgagtggcg aacgggtgag     60
taatacataa gtaacctgcc ctcatgaggg ggataactat tagaaatgat agctaagacc    120
gcataggtga aggggtcgca tgaccgcttc attaaatatc cgtatggata gcaggaggat    180
ggacttatgg cgcattagct ggttggtgag gtaacggctc accaaggcga cgatgcgtag    240
ccgacctgag agggtggacg gccacactgg gactgagaca cggcccagac tcctacggga    300
ggcagcagta gggaattttc ggcaatgggg gaaaccctga ccgagcaacg ccgcgtgagg    360
gaagaagtat ttcggtatgt aaacctctgt tataaggaa gaacggtatg aataggaaat    420
gattcataag tgacggtact ttatgagaaa gccacggcta actacgtgcc agcagccgcg    480
gtaatacgta ggtggcgagc gttatccgga atcattgggc gtaaagaggg agcaggcggc    540
aatagaggtc tgcggtgaaa gcctgaagct aaacttcagt aagccgtgga aaccaaatag    600
ctagagtgca gtagaggatc gtggaattcc atgtgtagcg gtgaaatgcg tagatatatg    660
gaggaacacc agtggcgaag gcgacgatct gggctgcaac tgacgctcag tcccgaaagc    720
gtggggagca aataggatta gatacccctag tagtccacgc cgtaaacgat gagtactaag    780
tgttgggggt caaacctcag tgctgcagtt aacgcaataa gtactccgcc tgagtagtac    840
gttcgcaaga atgaaactca aaggaattga cggggcccg cacaagcggt ggagcatgtg    900
gtttaattcg aagcaacgcg aagaacctta ccaggtcttg acatacctct aaaggctcta    960
gagatagaga gatagctata ggggatacag gtggtgcatg gttgtcgtca gctcgtgtcg    1020
```

-continued

```
tgagatgttg ggttaagtcc cgcaacgagc gcaacccttg tcgctagtta ccatcattaa   1080
gttggggact ctagcgagac tgcctctgca aggaggagga aggcggggat gacgtcaaat   1140
catcatgccc cttatgacct gggctacaca cgtgctacaa tggacggatc aaagggaagc   1200
gaagccgcga ggtggagcga aacccaaaaa cccgttctca gttcggactg cagtctgcaa   1260
ctcgactgca cgaagttgga atcgctagta atcgcgaatc agaatgtcgc ggtgaatacg   1320
ttctcgggcc ttgtacacac cgcccgtcac accatgagag ttggtaacac ccgaagccgg   1380
tggcttaacc gcaaggagag agcttctaag gtgaat                              1416
```

<210> SEQ ID NO 16
<211> LENGTH: 1424
<212> TYPE: DNA
<213> ORGANISM: Clostridium symbiosum

<400> SEQUENCE: 16

```
aggcgcgtgc taccatgcag tcgaacgaag caatttaacg gaagttttcg gatggaagtt    60
gaattgactg agtggcggac gggtgagtaa cgcgtgggta acctgccttg tactggggga   120
caacagttag aaatgactgc taataccgca taagcgcaca gtatcgcatg atacagtgtg   180
aaaaactccg gtggtacaag atggacccgc gtctgattag ctagttggta aggtaacggc   240
ttaccaaggc gacgatcagt agccgacctg agagggtgac cggccacatt gggactgaga   300
cacggcccaa actcctacgg gaggcagcag tggggaatat tgcacaatgg gcgaaagcct   360
gatgcagcga cgccgcgtga gtgaagaagt atttcggtat gtaaagctct atcagcaggg   420
aagaaaatga cggtacctga ctaagaagcc ccggctaact acgtgccagc agccgcggta   480
atacgtaggg ggcaagcgtt atccggattt actgggtgta aagggagcgt agacggtaaa   540
gcaagtctga agtgaaagcc gcggctcaa ctgcgggact gctttggaaa ctgtttaact   600
ggagtgtcgg agaggtaagt ggaattccta gtgtagcggt gaaatgcgta gatattagga   660
ggaacaccag tggcgaaggc gacttactgg acgataactg acgttgaggc tcgaaagcgt   720
ggggagcaaa caggattaga taccctggta gtccacgccg taaacgatga atactaggtg   780
ttggggagca aagctcttcg gtgccgtcgc aaacgcagta agtattccac ctggggagta   840
cgttcgcaag aatgaaactc aaaggaattg acggggaccc gcacaagcgg tggagcatgt   900
ggtttaattc gaagcaacgc gaagaacctt accaggtctt gacatcgatc gacggggga   960 gtaacgtccc cttcccttcg gggcggagaa gacaggtggt gcatggttgt cgtcagctcg  1020
tgtcgtgaga tgttgggtta agtcccgcaa cgagcgcaac ccttattcta gtagccagc   1080 ggttcggccg ggaactcttg ggagactgcc agggataacc tggaggaagg tggggatgac  1140
gtcaaatcat catgcccctt atgatctggg ctacacacgt gctacaatgg cgtaaacaaa  1200
gagaagcaag accgcgaggt ggagcaaatc tcaaaaataa cgtctcagtt cggactgcag  1260
gctgcaactc gcctgcacga agctggaatc gctagtaatc gcgaatcaga atgtcgcggt  1320
gaatacgttc ccgggtcttg tacacaccgc ccgtcacacc atgggagtca gtaacgcccg  1380
aagtcagtga cccaaccgca aggaggagcg ccgaaggcga ccgt                    1424
```

<210> SEQ ID NO 17
<211> LENGTH: 1426
<212> TYPE: DNA
<213> ORGANISM: Bacteroides dorei

<400> SEQUENCE: 17

```
cggtctcggc ttaccatgca gtcgaggggc agcatggtct tagcttgcta aggctgatgg      60
cgaccggcgc acgggtgagt aacacgtatc caacctgccg tctactcttg gccagccttc     120
tgaaaggaag attaatccag gatggcatca tgagttcaca tgtccgcatg attaaaggta     180
ttttccggta gacgatgggg atgcgttcca ttagatagta ggcggggtaa cggcccacct     240
agtcaacgat ggataggggt tctgagagga aggtccccca cattggaact gagacacggt     300
ccaaactcct acgggaggca gcagtgagga atattggtca atgggcgatg cctgaaccag     360
gccaagtagc gtgaaggatg actgccctat gggttgtaaa cttcttttat aaaggaataa     420
agtcgggtat gcatacccgt ttgcatgtac tttatgaata aggatcggct aactccgtgc     480
cagcagccgc ggtaatacgg aggatccgag cgttatccgg atttattggg tttaagggga     540
gcgtagatgg atgtttaagt cagttgtgaa agtttgcggc tcaaccgtaa aattgcagtt     600
gatactggat gtcttgagtg cagttgaggc aggcggaatt cgtggtgtag cggtgaaatg     660
cttagatatc acgaagaact ccgattgcga aggcagcctg ctaagctgca actgacattg     720
aggctcgaaa gtgtgggtat caaacaggat tagatacccct ggtagtccac acggtaaacg     780
atgaatactc gctgtttgcg atatacggca gcggccaagc gaaagcgtt aagtattcca     840 cctggggagt acgccggcaa cggtgaaact caaaggaatt gacgggggcc cgcacaagcg     900
gaggaacatg tggtttaatt cgatgatacg cgaggaacct tacccgggct taaattgcac     960
tcgaatgatc cggaaacggt tcagctagca atagcgagtg tgaaggtgct gcatggttgt    1020
cgtcagctcg tgccgtgagg tgtcggctta agtgccataa cgagcgcaac ccttgttgtc    1080
agttactaac aggtgatgct gaggactctg acaagactgc catcgtaaga tgtgaggaag    1140
gtgggatgac gtcaaatca gcacggccct acgtccggg gctacacacg tgttacaatg    1200 ggggggtacaa agggccgcta ccacgcgagt ggatgccaat ccctaaaacc cctctcagtt    1260
cggactggag tctgcaaccc gactccacga agctggattc gctagtaatc gcgcatcagc    1320
cacggcgcgt gaatacgttc ccgggccttt gtacacaccg cccgtcaagc catgggagcc    1380
gggggtacct gaagtgcgta accgcgagga tcgccctagg taatga                   1426
```

<210> SEQ ID NO 18
<211> LENGTH: 1428
<212> TYPE: DNA
<213> ORGANISM: Anaerostipes caccae

<400> SEQUENCE: 18

```
cggcggctgc ttaccatgca gtcgaacgaa gcatttagga ttgaagtttt cggatggatt      60
tcctatatga ctgagtggcg gacgggtgag taacgcgtgg ggaacctgcc ctatacaggg     120
ggataacagc tggaaacggc tgctaatacc gcataagcgc acagaatcgc atgattcagt     180
gtgaaaagcc ctggcagtat aggatggtcc cgcgtctgat tagctggttg gtgaggtaac     240
ggctcaccaa ggcgacgatc agtagccggc ttgagagagt gaacggccac attgggactg     300
agacacggcc caaactccta cgggaggcag cagtggggaa tattgcacaa tgggggaaac     360
cctgatgcag cgacgccgcg tgagtgaaga agtatttcgg tatgtaaagc tctatcagca     420
gggaagaaaa cagacggtac ctgactaaga agccccggct aactacgtgc cagcagccgc     480
ggtaatacgt agggggcaag cgttatccgg aattactggg tgtaagggt gcgtaggtgg     540 catggtaagt cagaagtgaa agcccggggc ttaaccccgg gactgctttt gaaactgtca     600
tgctggagtg caggagaggt aagcggaatt cctagtgtag cggtgaaatg cgtagatatt     660
aggaggaaca ccagtggcga aggcggctta ctggactgtc actgacactg atgcacgaaa     720
```

```
gcgtggggag caaacaggat tagataccct ggtagtccac gccgtaaacg atgaatacta    780
ggtgtcgggg ccgtagaggc ttcggtgccg cagcaaacgc agtaagtatt ccacctgggg    840
agtacgttcg caagaatgaa actcaaagga attgacgggg acccgcacaa gcggtggagc    900
atgtggttta attcgaagca acgcgaagaa ccttacctgg tcttgacatc ccaatgaccg    960
aaccttaacc ggttttttct ttcgagacat ggagacagg tggtgcatgg ttgtcgtcag    1020
ctcgtgtcgt gagatgttgg gttaagtccc gcaacgagcg caaccccctat ctttagtagc    1080 cagcatttaa ggtgggcact ctagagagac tgccagggat aacctggagg aaggtgggga    1140
cgacgtcaaa tcatcatgcc ccttatgcc agggctacac acgtgctaca atggcgtaaa    1200
caaagggaag cgaagtcgtg aggcgaagca atcccagaa ataacgtctc agttcggatt    1260
gtagtctgca actcgactac atgaagctgg aatcgctagt aatcgtgaat cagaatgtca    1320
cggtgaatac gttcccgggt cttgtacaca ccgcccgtca caccatggga gtcagtaacg    1380
cccgaagtca gtgacccaac cgcaaggagg gagctgccga agtacgag              1428
```

`<210>` SEQ ID NO 19
`<211>` LENGTH: 1082
`<212>` TYPE: DNA
`<213>` ORGANISM: Clostridium bolteae

`<400>` SEQUENCE: 19

```
tttgtggcga agcctgatgc agcgacgccg cgtgagtgaa gaagtatttc ggtatgtaaa     60
gctctatcag cagggaagaa aatgacggta cctgactaag aagccccggc taactacgtg    120
ccagcagccg cggtaatacg taggggggcaa gcgttatccg gatttactgg gtgtaaaggg    180
agcgtagacg gcgaagcaag tctgaagtga aaacccaggg ctcaaccctg ggactgcttt    240
ggaaactgtt ttgctagagt gtcggagagg taagtggaat tcctagtgta gcggtgaaat    300
gcgtagatat taggaggaac accagtggcg aaggcggctt actggacgat aactgacgtt    360
gaggctcgaa agcgtgggga gcaaacagga ttagataccc tggtagtcca cgccgtaaac    420
gatgaatgct aggtgttggg gggcaaagcc cttcggtgcc gtcgcaaacg cagtaagcat    480
tccacctggg gagtacgttc gcaagaatga aactcaaagg aattgacggg gacccgcaca    540
agcggtggag catgtggttt aattcgaagc aacgcgaaga accttaccaa gtcttgacat    600
cctcttgacc ggcgtgtaac ggcgccttcc cttcggggca agagagacag gtggtgcatg    660
gttgtcgtca gctcgtgtcg tgagatgttg ggttaagtcc cgcaacgagc gcaaccctta    720
tccttagtag ccagcaggta aagctgggca ctctaggggag actgccaggg ataacctgga    780
ggaaggtggg gatgacgtca aatcatcatg ccccttatga tttgggctac acacgtgcta    840
caatggcgta aacaaaggga agcaagacag tgatgtggag caaatcccaa aaataacgtc    900
ccagttcgga ctgtagtctg caacccgact acacgaagct ggaatcgcta gtaatcgcga    960
atcagaatgt cgcggtgaat acgttcccgg gtcttgtaca caccgcccgt cacaccatgg   1020
gagtcagcaa cgcccgaagt cagtgaccca actcgcaaga gagggagcgc cgaagtcgtc   1080
at                                                                1082
```

`<210>` SEQ ID NO 20
`<211>` LENGTH: 1426
`<212>` TYPE: DNA
`<213>` ORGANISM: Clostridium citroniae

`<400>` SEQUENCE: 20

| | |
|---|---|
| ctggcgcggc taccatgcag tcgagcgaag cattacagcg aagttttcg gatggaagct | 60 |
| ttaatgactg agcggcggac gggtgagtaa cgcgtggata acctgcctca tacagggga | 120 |
| taacagttag aaatgactgc taataccgca taagcgcaca gtatcgcatg atacggtgtg | 180 |
| aaaaactccg gtggtatgag atggatccgc gtctgattag ttagttggcg ggtaaaggc | 240 |
| ccaccaagac gacgatcagt agccggcctg agagggtgaa cggccacatt gggactgaga | 300 |
| cacggcccaa actcctacgg gaggcagcag tggggaatat tgcacaatgg gggaaaccct | 360 |
| gatgcagcga cgccgcgtga gtgaagaagt atttcggtat gtaaagctct atcagcaggg | 420 |
| aagaaaatga cggtacctga ctaagaagcc ccggctaact acgtgccagc agccgcggta | 480 |
| atacgtaggg ggcaagcgtt atccggattt actgggtgta agggagcgt agacggcaat | 540 |
| gcaagtctgg agtgaaaacc cagggctcaa ccctgggagt gctttggaaa ctgtatagct | 600 |
| agagtgctgg agaggtaagt ggaattccta gtgtagcggt gaaatgcgta gatattagga | 660 |
| ggaacaccag tggcgaaggc ggcttactgg acagtaactg acgttgaggc tcgaaagcgt | 720 |
| ggggagcaaa caggattaga taccctggta gtccacgccg taaacgatga atgctaggtg | 780 |
| ttgggggca aagcccttcg gtgccgtcgc aaacgcaata agcattccac tggggagta | 840 |
| cgttcgcaag aatgaaactc aaaggaattg acggggaccc gcacaagcgg tggagcatgt | 900 |
| ggtttaattc gaagcaacgc gaagaacctt accaagtctt gacatcctcc tgaccggtcc | 960 |
| gtaacggggc ctttccttcg gacaagaga acaggtggg catggttgt cgtcagctcg | 1020 |
| tgtcgtgaga tgttgggtta agtcccgcaa cgagcgcaac ccttatcctt agtagccagc | 1080 |
| aggtagagct gggcactcta gggagactgc caggataac ctggaggaag gtggggatga | 1140 |
| cgtcaaatca tcatgcccct tatgatttgg gctacacacg tgctacaatg gcgtaaacaa | 1200 |
| agggaggcga ccctgcgaag gcaagcaaat cccaaaaata acgtcccagt tcggactgta | 1260 |
| gtctgcaacc cgactacacg aagctggaat cgctagtaat cgcgaatcag aatgtcgcgg | 1320 |
| tgaatacgtt cccgggtctt gtacacaccg cccgtcacac catgggagtc agcaacgccc | 1380 |
| gaagtcagtg acccaactgc aggagaggga gcgccgaagt cgggct | 1426 |

<210> SEQ ID NO 21
<211> LENGTH: 30
<212> TYPE: DNA
<213> ORGANISM: Artificial Sequence
<220> FEATURE:
<223> OTHER INFORMATION: 454 adaptor sequence

<400> SEQUENCE: 21
ccatctcatc cctgcgtgtc tccgactcag            30

<210> SEQ ID NO 22
<211> LENGTH: 20
<212> TYPE: DNA
<213> ORGANISM: Artificial Sequence
<220> FEATURE:
<223> OTHER INFORMATION: partial sequence of modified primer 8F

<400> SEQUENCE: 22
agrgtttgat ymtggctcag            20

<210> SEQ ID NO 23
<211> LENGTH: 30
<212> TYPE: DNA
<213> ORGANISM: Artificial Sequence
<220> FEATURE:
<223> OTHER INFORMATION: 454 adaptor sequence

```
<400> SEQUENCE: 23
cctatcccct gtgtgccttg gcagtctcag                                          30

<210> SEQ ID NO 24
<211> LENGTH: 19
<212> TYPE: DNA
<213> ORGANISM: Artificial Sequence
<220> FEATURE:
<223> OTHER INFORMATION: partial sequence of modified primer 338R

<400> SEQUENCE: 24
tgctgcctcc cgtaggagt                                                      19

<210> SEQ ID NO 25
<211> LENGTH: 20
<212> TYPE: DNA
<213> ORGANISM: Artificial Sequence
<220> FEATURE:
<223> OTHER INFORMATION: primer 8F

<400> SEQUENCE: 25
agagtttgat cmtggctcag                                                     20

<210> SEQ ID NO 26
<211> LENGTH: 19
<212> TYPE: DNA
<213> ORGANISM: Artificial Sequence
<220> FEATURE:
<223> OTHER INFORMATION: primer 1492R

<400> SEQUENCE: 26
ggytaccttg ttacgactt                                                      19
```